United States Patent
Shelton, IV et al.

(10) Patent No.: US 12,383,263 B2
(45) Date of Patent: Aug. 12, 2025

(54) SURGICAL INSTRUMENT COMPRISING A SIGNAL INTERFERENCE RESOLUTION SYSTEM

(71) Applicant: Cilag GmbH International, Zug (CH)

(72) Inventors: Frederick E. Shelton, IV, Hillsboro, OH (US); Jason L. Harris, Lebanon, OH (US); Patrick L. Creamer, New Orleans, LA (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/388,345

(22) Filed: Nov. 9, 2023

(65) Prior Publication Data

US 2024/0148377 A1 May 9, 2024

Related U.S. Application Data

(62) Division of application No. 16/895,291, filed on Jun. 8, 2020, now Pat. No. 11,812,957.

(Continued)

(51) Int. Cl.
| | |
|---|---|
| *A61B 17/072* | (2006.01) |
| *A61B 34/20* | (2016.01) |
| *A61B 17/00* | (2006.01) |
| *A61B 17/068* | (2006.01) |
| *A61B 17/29* | (2006.01) |

(Continued)

(52) U.S. Cl.
CPC ...... *A61B 17/072* (2013.01); *A61B 17/07207* (2013.01); *A61B 34/20* (2016.02); *A61B 2017/00039* (2013.01); *A61B 2017/00477* (2013.01); *A61B 17/068* (2013.01); *A61B 2017/07214* (2013.01); *A61B 2017/07285* (2013.01); *A61B 2017/2927* (2013.01); *A61B 17/3423* (2013.01); *A61B 2034/2055* (2016.02); *A61B 2034/2072* (2016.02);

(Continued)

(58) Field of Classification Search
CPC ............... A61B 17/068; A61B 17/072; A61B 17/07207; A61B 17/3423; A61B 17/7074; A61B 17/115; A61B 34/20; A61B 34/30; A61B 34/37; A61B 34/76; A61B 2017/07214; A61B 2017/00017; A61B 2017/00022; A61B 2017/00477; A61B 2017/2927; A61B 2017/2943; A61B 90/03; A61B 90/98
USPC ..... 227/19, 175.1, 175.2, 176.1; 606/1, 139, 606/153, 213, 219
See application file for complete search history.

(56) References Cited

U.S. PATENT DOCUMENTS

| | | |
|---|---|---|
| 5,403,312 A | 4/1995 | Yates et al. |
| 5,693,042 A | 12/1997 | Boiarski et al. |

(Continued)

FOREIGN PATENT DOCUMENTS

| | | |
|---|---|---|
| CN | 201029899 Y | 3/2008 |
| CN | 107374752 A | 11/2017 |

(Continued)

OTHER PUBLICATIONS

"ATM-MPLS Network Interworking Version 2.0, af-aic-0178.001" ATM Standard, The ATM Forum Technical Committee, published Aug. 2003.

(Continued)

*Primary Examiner* — Scott A Smith

(57) ABSTRACT

A surgical instrument including a signal interference detection system.

20 Claims, 30 Drawing Sheets

Related U.S. Application Data

(60) Provisional application No. 62/955,306, filed on Dec. 30, 2019.

(51) Int. Cl.
    A61B 17/34    (2006.01)
    A61B 34/00    (2016.01)
    A61B 34/37    (2016.01)

(52) U.S. Cl.
    CPC ............... *A61B 34/37* (2016.02); *A61B 34/76* (2016.02); *A61B 2562/0223* (2013.01)

(56) References Cited

U.S. PATENT DOCUMENTS

| | | |
|---|---|---|
| 7,000,818 B2 | 2/2006 | Shelton, IV et al. |
| 7,422,139 B2 | 9/2008 | Shelton, IV et al. |
| 7,464,849 B2 | 12/2008 | Shelton, IV et al. |
| 7,525,309 B2 | 4/2009 | Sherman et al. |
| 7,670,334 B2 | 3/2010 | Hueil et al. |
| 7,753,245 B2 | 7/2010 | Boudreaux et al. |
| 7,784,663 B2 | 8/2010 | Shelton, IV |
| 7,845,537 B2 | 12/2010 | Shelton, IV et al. |
| 7,980,443 B2 | 7/2011 | Scheib et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,360,299 B2 | 1/2013 | Zemlok et al. |
| 8,393,514 B2 | 3/2013 | Shelton, IV et al. |
| 8,444,036 B2 | 5/2013 | Shelton, IV |
| 8,523,043 B2 | 9/2013 | Ullrich et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,807,414 B2 | 8/2014 | Ross et al. |
| 9,044,230 B2 | 6/2015 | Morgan et al. |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,307,986 B2 | 4/2016 | Hall et al. |
| 9,326,767 B2 | 5/2016 | Koch, Jr. et al. |
| 9,332,987 B2 | 5/2016 | Leimbach et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,398,911 B2 | 7/2016 | Auld |
| 9,421,014 B2 | 8/2016 | Ingmanson et al. |
| 9,468,438 B2 | 10/2016 | Baber et al. |
| 9,554,465 B1 | 1/2017 | Liu et al. |
| 9,554,794 B2 | 1/2017 | Baber et al. |
| 9,592,056 B2 | 3/2017 | Mozdzierz et al. |
| 9,629,623 B2 | 4/2017 | Lytle, IV et al. |
| 9,629,629 B2 | 4/2017 | Leimbach et al. |
| 9,649,110 B2 | 5/2017 | Parihar et al. |
| 9,687,230 B2 | 6/2017 | Leimbach et al. |
| 9,690,362 B2 | 6/2017 | Leimbach et al. |
| 9,700,309 B2 | 7/2017 | Jaworek et al. |
| 9,724,094 B2 | 8/2017 | Baber et al. |
| 9,733,663 B2 | 8/2017 | Leimbach et al. |
| 9,737,301 B2 | 8/2017 | Baber et al. |
| 9,743,929 B2 | 8/2017 | Leimbach et al. |
| 9,750,499 B2 | 9/2017 | Leimbach et al. |
| 9,757,128 B2 | 9/2017 | Baber et al. |
| 9,782,169 B2 | 10/2017 | Kimsey et al. |
| 9,788,836 B2 | 10/2017 | Overmyer et al. |
| 9,801,626 B2 | 10/2017 | Parihar et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,814,460 B2 | 11/2017 | Kimsey et al. |
| 9,815,211 B2 | 11/2017 | Cao et al. |
| 9,820,738 B2 | 11/2017 | Lytle, IV et al. |
| 9,826,976 B2 | 11/2017 | Parihar et al. |
| 9,826,977 B2 | 11/2017 | Leimbach et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,867,612 B2 | 1/2018 | Parihar et al. |
| 9,883,860 B2 | 2/2018 | Leimbach et al. |
| 9,888,919 B2 | 2/2018 | Leimbach et al. |
| 9,895,148 B2 | 2/2018 | Shelton, IV et al. |
| 9,901,342 B2 | 2/2018 | Shelton, IV et al. |
| 9,913,642 B2 | 3/2018 | Leimbach et al. |
| 9,924,961 B2 | 3/2018 | Shelton, IV et al. |
| 9,931,118 B2 | 4/2018 | Shelton, IV et al. |
| 9,943,309 B2 | 4/2018 | Shelton, IV et al. |
| 9,968,355 B2 | 5/2018 | Shelton, IV et al. |
| 9,987,000 B2 | 6/2018 | Shelton, IV et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| D822,206 S | 7/2018 | Shelton, IV et al. |
| 10,013,049 B2 | 7/2018 | Leimbach et al. |
| 10,016,199 B2 | 7/2018 | Baber et al. |
| 10,028,761 B2 | 7/2018 | Leimbach et al. |
| D826,405 S | 8/2018 | Shelton, IV et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,052,044 B2 | 8/2018 | Shelton, IV et al. |
| 10,052,102 B2 | 8/2018 | Baxter, III et al. |
| 10,085,748 B2 | 10/2018 | Morgan et al. |
| 10,111,679 B2 | 10/2018 | Baber et al. |
| 10,117,649 B2 | 11/2018 | Baxter, III et al. |
| 10,130,367 B2 | 11/2018 | Cappola et al. |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,159,483 B2 | 12/2018 | Beckman et al. |
| 10,178,992 B2 | 1/2019 | Wise et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,194,907 B2 | 2/2019 | Marczyk et al. |
| 10,201,364 B2 | 2/2019 | Leimbach et al. |
| 10,226,250 B2 | 3/2019 | Beckman et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,258,331 B2 | 4/2019 | Shelton, IV et al. |
| 10,265,068 B2 | 4/2019 | Harris et al. |
| 10,271,851 B2 | 4/2019 | Shelton, IV et al. |
| D847,989 S | 5/2019 | Shelton, IV et al. |
| 10,285,705 B2 | 5/2019 | Shelton, IV et al. |
| 10,292,704 B2 | 5/2019 | Harris et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,582 B2 | 6/2019 | Shelton, IV et al. |
| 10,321,907 B2 | 6/2019 | Shelton, IV et al. |
| D854,151 S | 7/2019 | Shelton, IV et al. |
| 10,335,149 B2 | 7/2019 | Baxter, III et al. |
| 10,342,543 B2 | 7/2019 | Shelton, IV et al. |
| 10,342,623 B2 | 7/2019 | Huelman et al. |
| 10,348,941 B2 | 7/2019 | Elliot, Jr. et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,390,841 B2 | 8/2019 | Shelton, IV et al. |
| 10,398,439 B2 | 9/2019 | Cabrera et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,420,552 B2 | 9/2019 | Shelton, IV et al. |

(56) References Cited

U.S. PATENT DOCUMENTS

| | | |
|---|---|---|
| D865,175 S | 10/2019 | Widenhouse et al. |
| 10,426,471 B2 | 10/2019 | Shelton, IV et al. |
| 10,433,837 B2 | 10/2019 | Worthington et al. |
| 10,433,849 B2 | 10/2019 | Shelton, IV et al. |
| 10,441,279 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,456,140 B2 | 10/2019 | Shelton, IV et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| D869,655 S | 12/2019 | Shelton, IV et al. |
| 10,492,785 B2 | 12/2019 | Overmyer et al. |
| 10,499,914 B2 | 12/2019 | Huang et al. |
| 10,517,595 B2 | 12/2019 | Hunter et al. |
| 10,517,596 B2 | 12/2019 | Hunter et al. |
| 10,524,789 B2 | 1/2020 | Swayze et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,603,036 B2 | 3/2020 | Hunter et al. |
| 10,610,224 B2 | 4/2020 | Shelton, IV et al. |
| 10,610,313 B2 | 4/2020 | Bailey et al. |
| 10,617,412 B2 | 4/2020 | Shelton, IV et al. |
| 10,624,635 B2 | 4/2020 | Harris et al. |
| 10,631,858 B2 | 4/2020 | Burbank |
| 10,631,859 B2 | 4/2020 | Shelton, IV et al. |
| 10,632,630 B2 | 4/2020 | Cao et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,646,292 B2 | 5/2020 | Solomon et al. |
| 10,653,413 B2 | 5/2020 | Worthington et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,702,270 B2 | 7/2020 | Shelton, IV et al. |
| 10,709,446 B2 | 7/2020 | Harris et al. |
| 10,722,233 B2 | 7/2020 | Wellman |
| D893,717 S | 8/2020 | Messerly et al. |
| 10,736,629 B2 | 8/2020 | Shelton, IV et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,765,427 B2 | 9/2020 | Shelton, IV et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,786,253 B2 | 9/2020 | Shelton, IV et al. |
| 10,806,454 B2 | 10/2020 | Kopp |
| 10,813,638 B2 | 10/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,492 B2 | 11/2020 | Shelton, IV et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,881,409 B2 | 1/2021 | Cabrera |
| 10,888,322 B2 | 1/2021 | Morgan et al. |
| 10,893,863 B2 | 1/2021 | Shelton, IV et al. |
| 10,893,864 B2 | 1/2021 | Harris et al. |
| 10,898,186 B2 | 1/2021 | Bakos et al. |
| 10,912,559 B2 | 2/2021 | Harris et al. |
| 10,918,385 B2 | 2/2021 | Overmyer et al. |
| D914,878 S | 3/2021 | Shelton, IV et al. |
| 10,932,766 B2 | 3/2021 | Tesar et al. |
| 10,945,727 B2 | 3/2021 | Shelton, IV et al. |
| 10,959,727 B2 | 3/2021 | Hunter et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,993,715 B2 | 5/2021 | Shelton, IV et al. |
| 10,993,716 B2 | 5/2021 | Shelton, IV et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,058,424 B2 | 7/2021 | Shelton, IV et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,096,688 B2 | 8/2021 | Shelton, IV et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,134,942 B2 | 10/2021 | Harris et al. |
| 11,141,154 B2 | 10/2021 | Shelton, IV et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |

(56) References Cited

U.S. PATENT DOCUMENTS

| | | |
|---|---|---|
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,406,382 B2 | 8/2022 | Shelton, IV et al. |
| 11,419,606 B2 | 8/2022 | Overmyer et al. |
| 11,424,027 B2 | 8/2022 | Shelton, IV |
| 11,426,167 B2 | 8/2022 | Shelton, IV et al. |
| D964,564 S | 9/2022 | Boudreaux |
| 11,446,029 B2 | 9/2022 | Shelton, IV et al. |
| 11,452,525 B2 | 9/2022 | Shelton, IV et al. |
| 11,464,511 B2 | 10/2022 | Timm et al. |
| 11,464,512 B2 | 10/2022 | Shelton, IV et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,206 B2 | 10/2022 | Henderson et al. |
| 11,478,242 B2 | 10/2022 | Shelton, IV et al. |
| 11,484,310 B2 | 11/2022 | Shelton, IV et al. |
| 11,504,122 B2 | 11/2022 | Shelton, IV et al. |
| 11,517,309 B2 | 12/2022 | Bakos et al. |
| 11,529,137 B2 | 12/2022 | Shelton, IV et al. |
| 11,529,139 B2 | 12/2022 | Shelton, IV et al. |
| 11,553,971 B2 | 1/2023 | Shelton, IV et al. |
| 11,559,304 B2 | 1/2023 | Boudreaux et al. |
| 11,559,307 B2 | 1/2023 | Shelton, IV et al. |
| 11,559,308 B2 | 1/2023 | Yates et al. |
| 11,571,210 B2 | 2/2023 | Shelton, IV et al. |
| 11,576,672 B2 | 2/2023 | Shelton, IV et al. |
| 11,576,677 B2 | 2/2023 | Shelton, IV et al. |
| 11,589,865 B2 | 2/2023 | Shelton, IV et al. |
| 11,589,888 B2 | 2/2023 | Shelton, IV et al. |
| 11,589,916 B2 | 2/2023 | Shelton, IV et al. |
| 11,607,219 B2 | 3/2023 | Shelton, IV et al. |
| 11,638,587 B2 | 5/2023 | Shelton, IV et al. |
| 11,653,920 B2 | 5/2023 | Shelton, IV et al. |
| 11,659,023 B2 | 5/2023 | Shelton, IV et al. |
| 11,660,089 B2 | 5/2023 | Shelton, IV et al. |
| 11,660,163 B2 | 5/2023 | Shelton, IV et al. |
| 11,666,368 B2 | 6/2023 | Henderson et al. |
| 11,678,880 B2 | 6/2023 | Shelton, IV et al. |
| 11,678,925 B2 | 6/2023 | Henderson et al. |
| 11,684,412 B2 | 6/2023 | Shelton, IV et al. |
| 11,684,434 B2 | 6/2023 | Shelton, IV |
| 11,696,759 B2 | 7/2023 | Shelton, IV et al. |
| 11,696,761 B2 | 7/2023 | Shelton, IV |
| 11,696,776 B2 | 7/2023 | Shelton, IV et al. |
| 11,701,111 B2 | 7/2023 | Shelton, IV et al. |
| 11,707,318 B2 | 7/2023 | Shelton, IV et al. |
| 11,723,716 B2 | 8/2023 | Fiebig et al. |
| 11,744,636 B2 | 9/2023 | Shelton, IV et al. |
| 11,751,872 B2 | 9/2023 | Zeiner et al. |
| 11,759,251 B2 | 9/2023 | Shelton, IV et al. |
| 11,771,419 B2 | 10/2023 | Shelton, IV et al. |
| 11,779,329 B2 | 10/2023 | Shelton, IV et al. |
| 11,779,387 B2 | 10/2023 | Salguero et al. |
| 11,786,291 B2 | 10/2023 | Sarley et al. |
| 11,786,294 B2 | 10/2023 | Shelton, IV et al. |
| 11,812,957 B2 | 11/2023 | Shelton, IV et al. |
| 11,853,835 B2 | 12/2023 | Shelton, IV |
| 11,857,152 B2 | 1/2024 | Shelton, IV et al. |
| 11,871,901 B2 | 1/2024 | Shelton, IV et al. |
| 11,903,601 B2 | 2/2024 | Shelton, IV et al. |
| 11,911,063 B2 | 2/2024 | Strobl |
| 11,937,769 B2 | 3/2024 | Shelton, IV et al. |
| 11,937,863 B2 | 3/2024 | Messerly et al. |
| 11,937,866 B2 | 3/2024 | Shelton, IV et al. |
| 11,944,366 B2 | 4/2024 | Faller et al. |
| 2007/0175955 A1 | 8/2007 | Shelton et al. |
| 2009/0090763 A1 | 4/2009 | Zemlok et al. |
| 2014/0207124 A1 | 7/2014 | Aldridge et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0373003 A1 | 12/2014 | Grez et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2016/0044841 A1 | 2/2016 | Chamberlain |
| 2016/0066913 A1 | 3/2016 | Swayze et al. |
| 2016/0249910 A1 | 9/2016 | Shelton, IV et al. |
| 2017/0224332 A1 | 8/2017 | Hunter et al. |
| 2017/0231628 A1 | 8/2017 | Shelton, IV et al. |
| 2017/0281186 A1 | 10/2017 | Shelton, IV et al. |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0289432 A1 | 10/2018 | Kostrzewski et al. |
| 2018/0325517 A1 | 11/2018 | Wingardner et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0038283 A1 | 2/2019 | Shelton, IV et al. |
| 2019/0200977 A1 | 7/2019 | Shelton, IV et al. |
| 2019/0200981 A1 | 7/2019 | Harris et al. |
| 2019/0201045 A1 | 7/2019 | Yates et al. |
| 2019/0201594 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0298353 A1 | 10/2019 | Shelton, IV et al. |
| 2019/0366562 A1 | 12/2019 | Zhang et al. |
| 2020/0054321 A1 | 2/2020 | Harris et al. |
| 2020/0100825 A1 | 4/2020 | Henderson et al. |
| 2020/0188047 A1 | 6/2020 | Itkowitz et al. |
| 2020/0315623 A1 | 10/2020 | Eisinger et al. |
| 2020/0315712 A1 | 10/2020 | Jasperson et al. |
| 2020/0405302 A1 | 12/2020 | Shelton, IV et al. |
| 2021/0186492 A1 | 6/2021 | Shelton, IV et al. |

(56) References Cited

U.S. PATENT DOCUMENTS

| | | |
|---|---|---|
| 2021/0186497 A1 | 6/2021 | Shelton, IV et al. |
| 2021/0186499 A1 | 6/2021 | Shelton, IV et al. |
| 2021/0186501 A1 | 6/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1* | 7/2021 | Shelton, IV ............ A61B 34/20 |
| 2021/0196269 A1 | 7/2021 | Shelton, IV et al. |
| 2021/0196270 A1 | 7/2021 | Shelton, IV et al. |
| 2021/0196302 A1 | 7/2021 | Shelton, IV et al. |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196352 A1 | 7/2021 | Messerly et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2022/0167982 A1 | 6/2022 | Shelton, IV et al. |
| 2022/0167984 A1* | 6/2022 | Shelton, IV ..... A61B 17/07207 |

FOREIGN PATENT DOCUMENTS

| | | |
|---|---|---|
| EP | 3476302 A2 | 5/2019 |
| EP | 3476331 A1 | 5/2019 |
| EP | 3694298 A1 | 8/2020 |
| WO | WO-2006091494 A1 | 8/2006 |
| WO | WO-2016130844 A1 | 8/2016 |
| WO | WO-2019130090 A1 | 7/2019 |
| WO | WO-2019130113 A1 | 7/2019 |

OTHER PUBLICATIONS

IEEE Std 802.3-2012 (Revision of IEEE Std 802.3-2008, published Dec. 28, 2012.

* cited by examiner

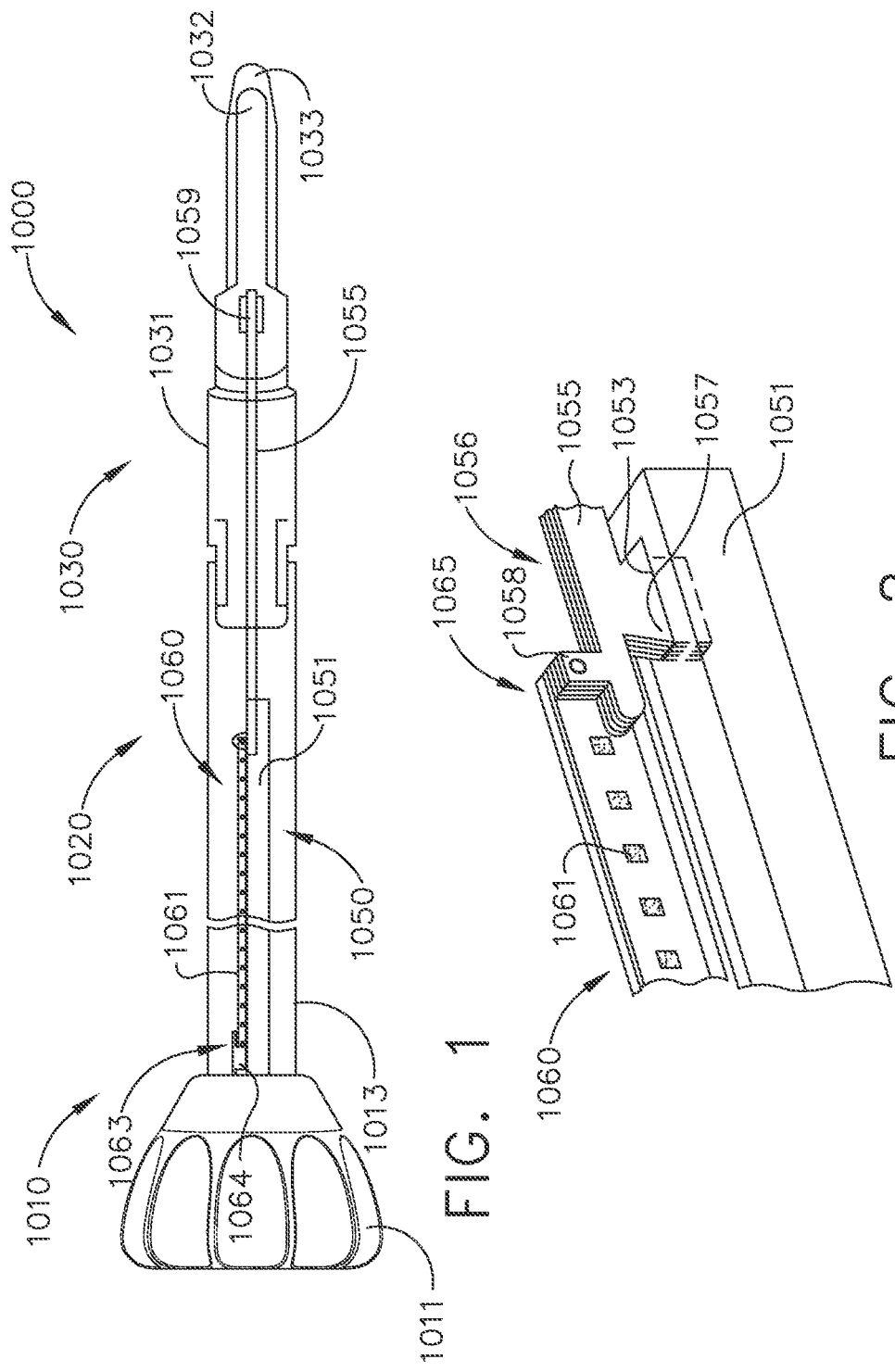

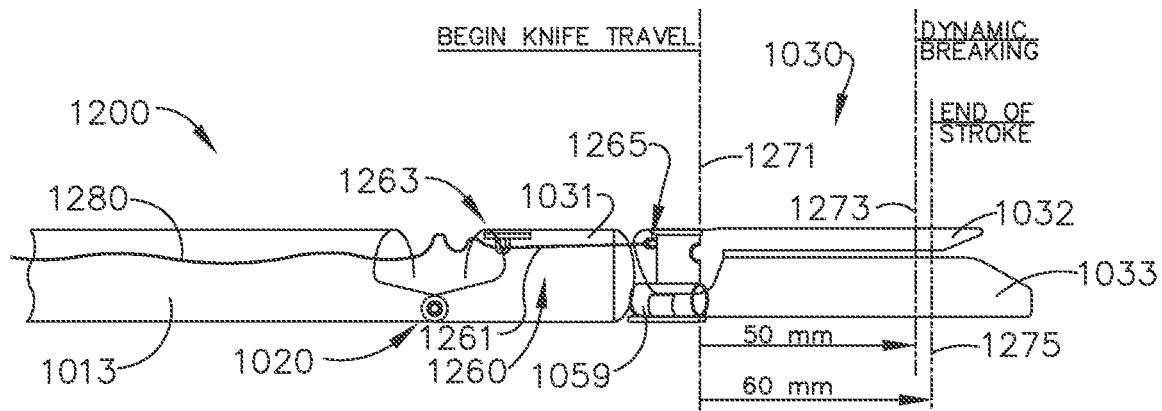
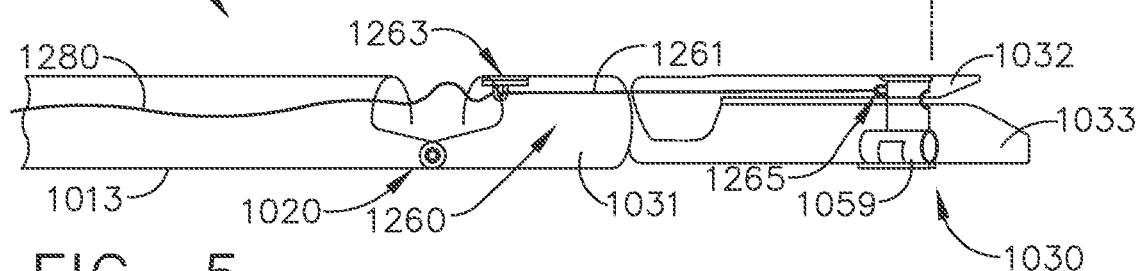
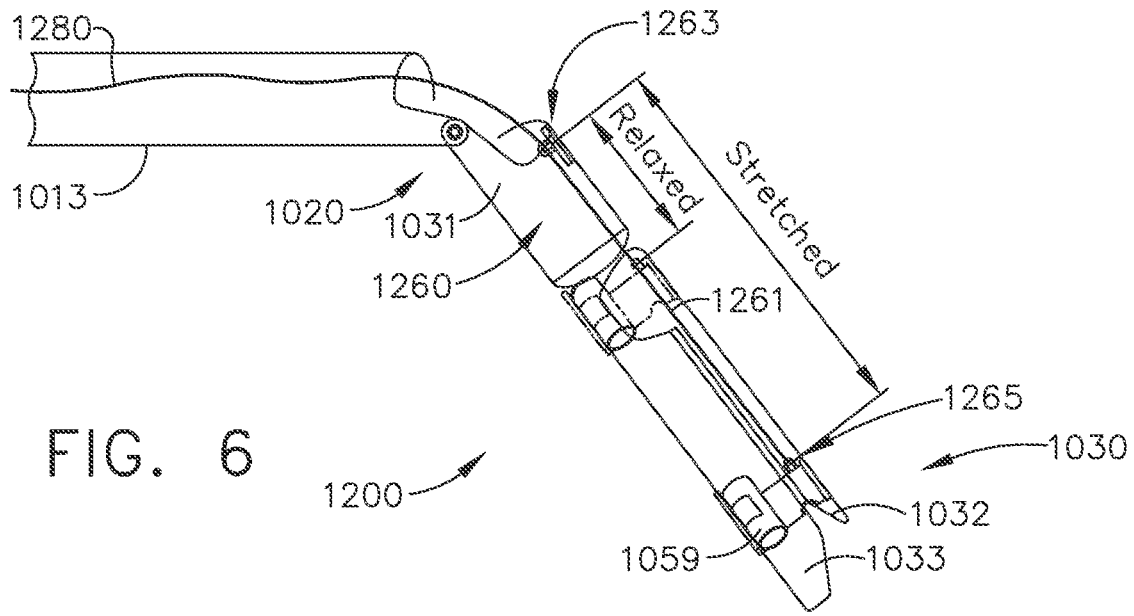

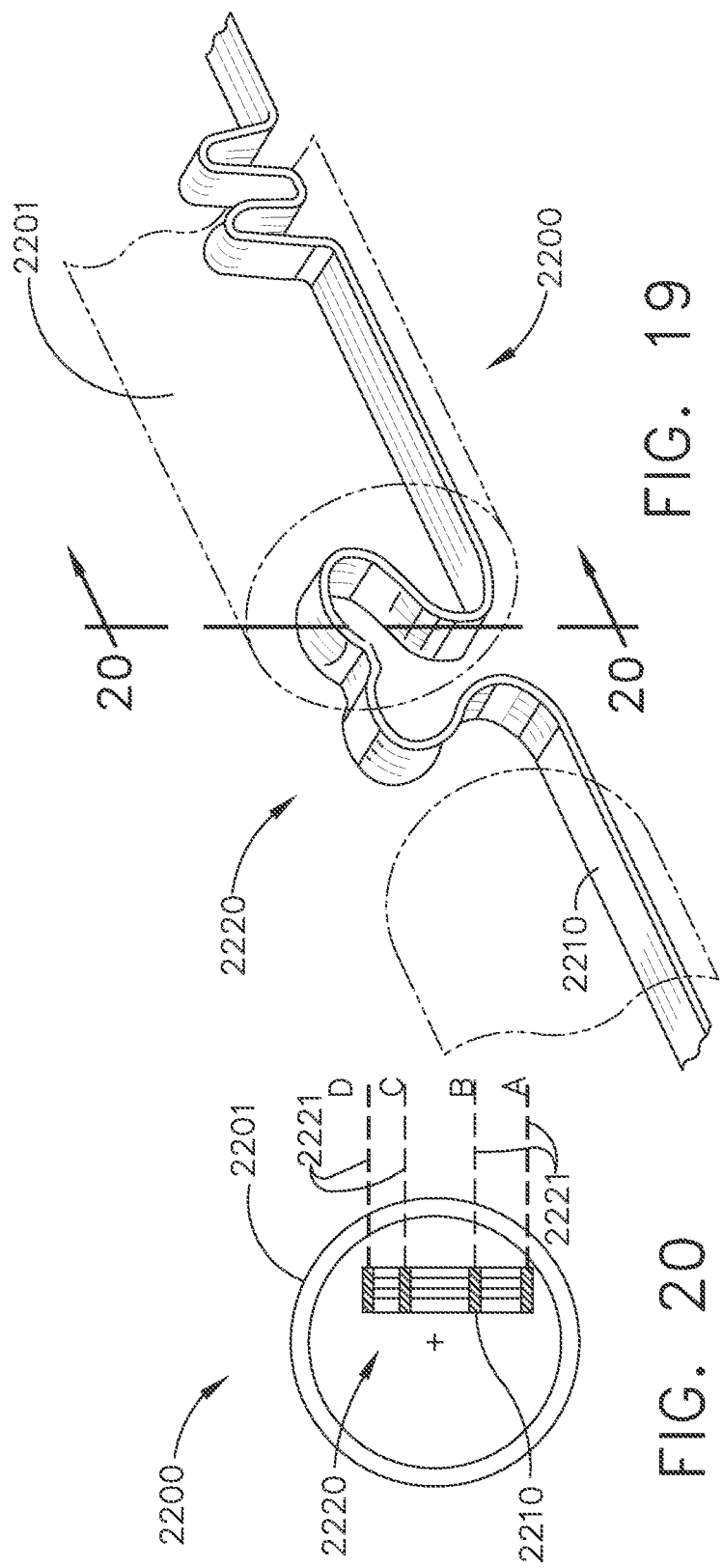

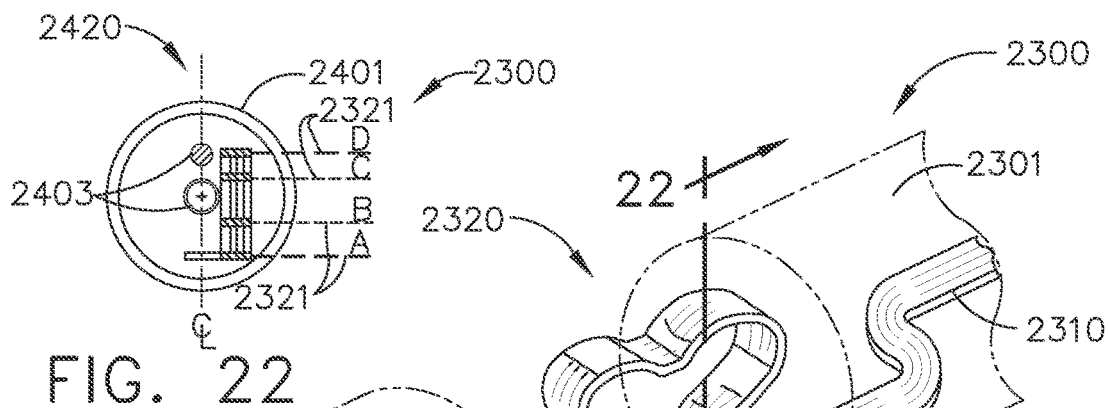
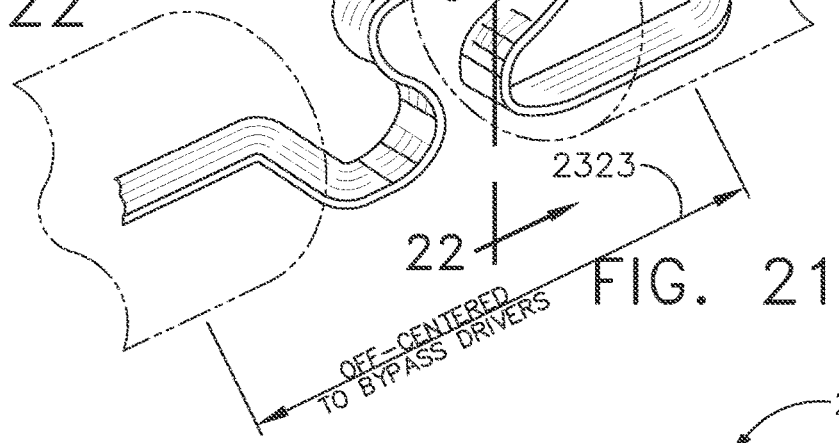
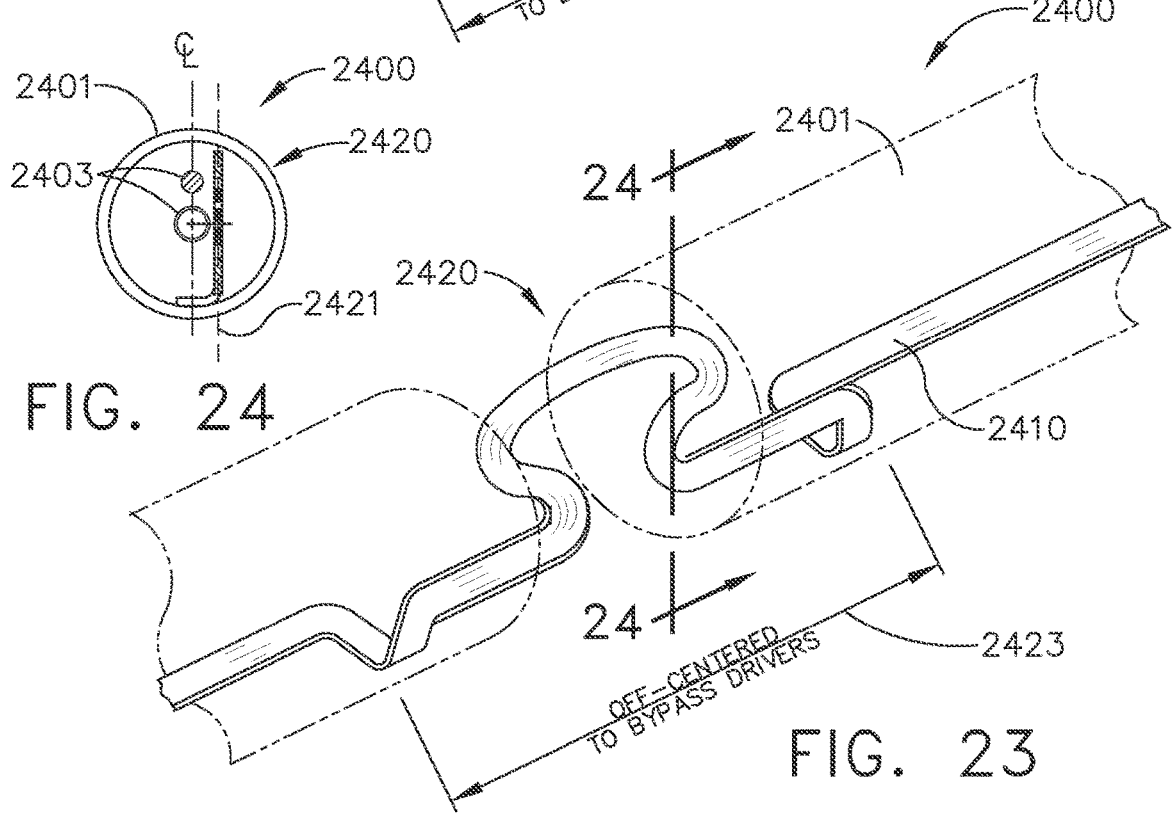

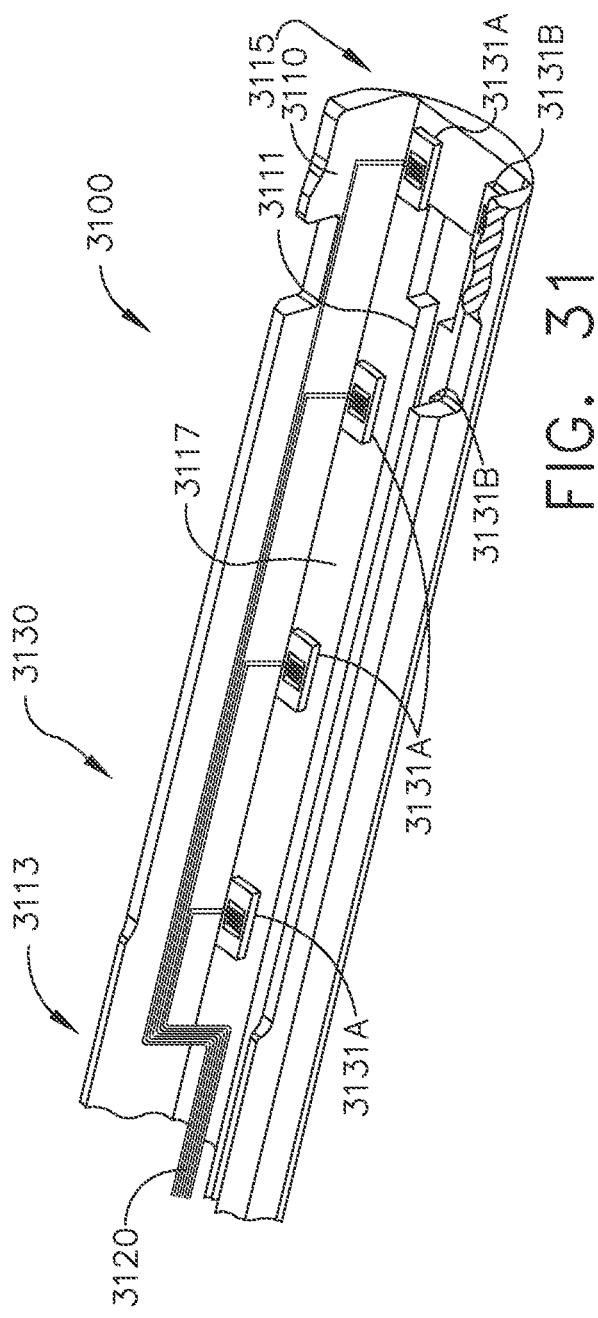
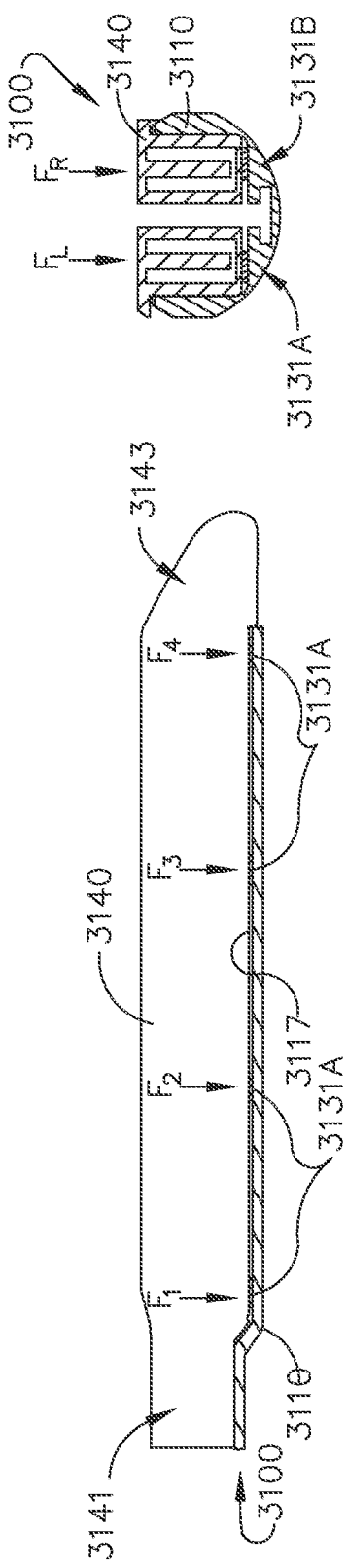
FIG. 31
FIG. 32
FIG. 33

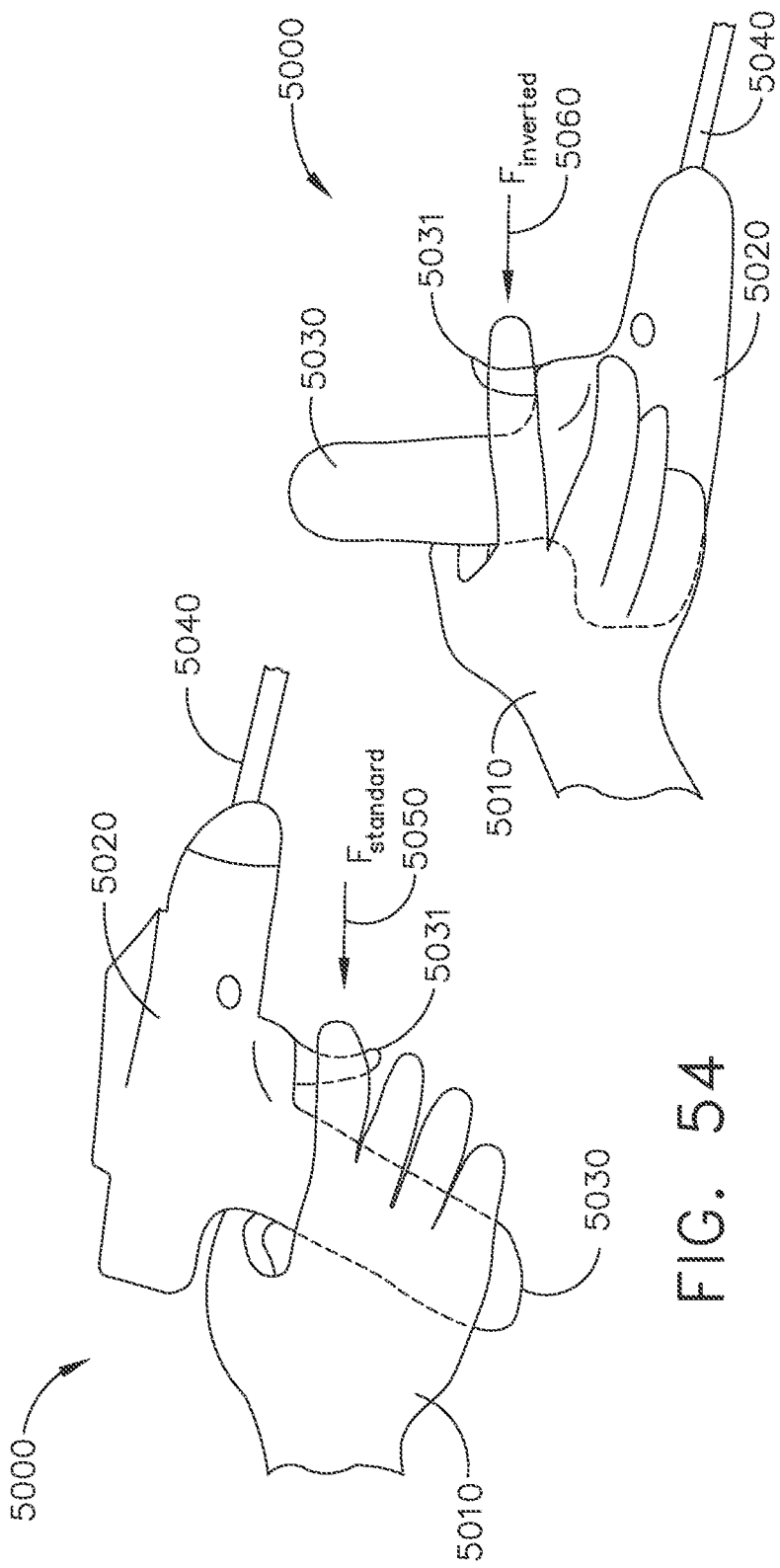

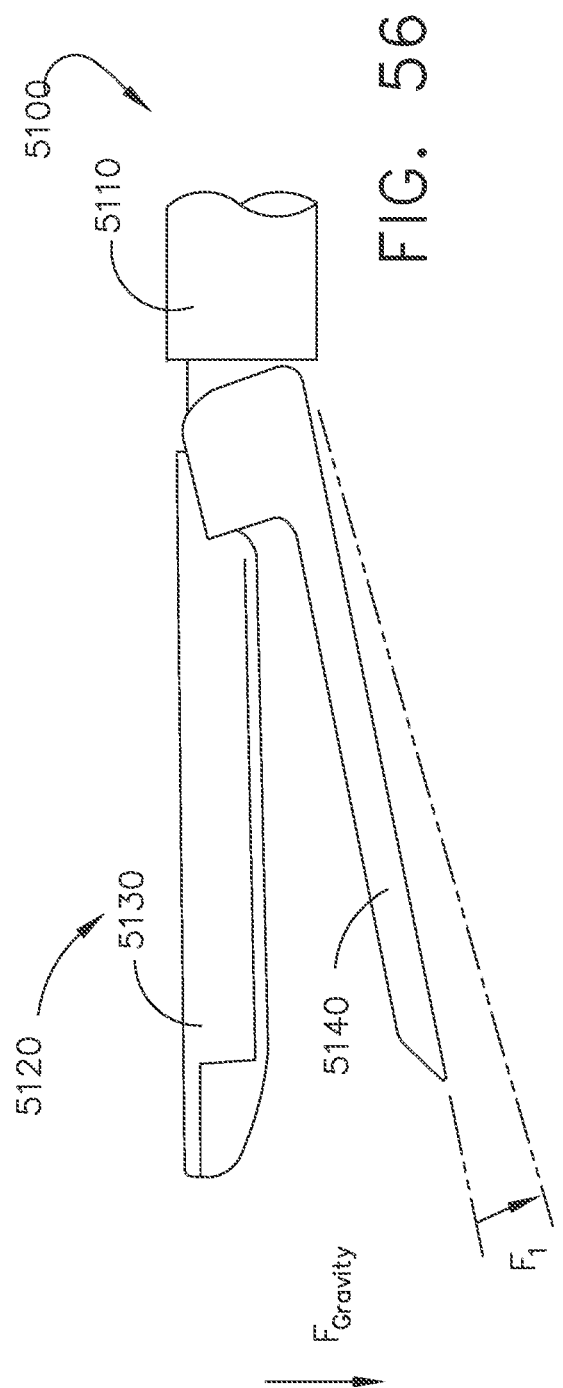
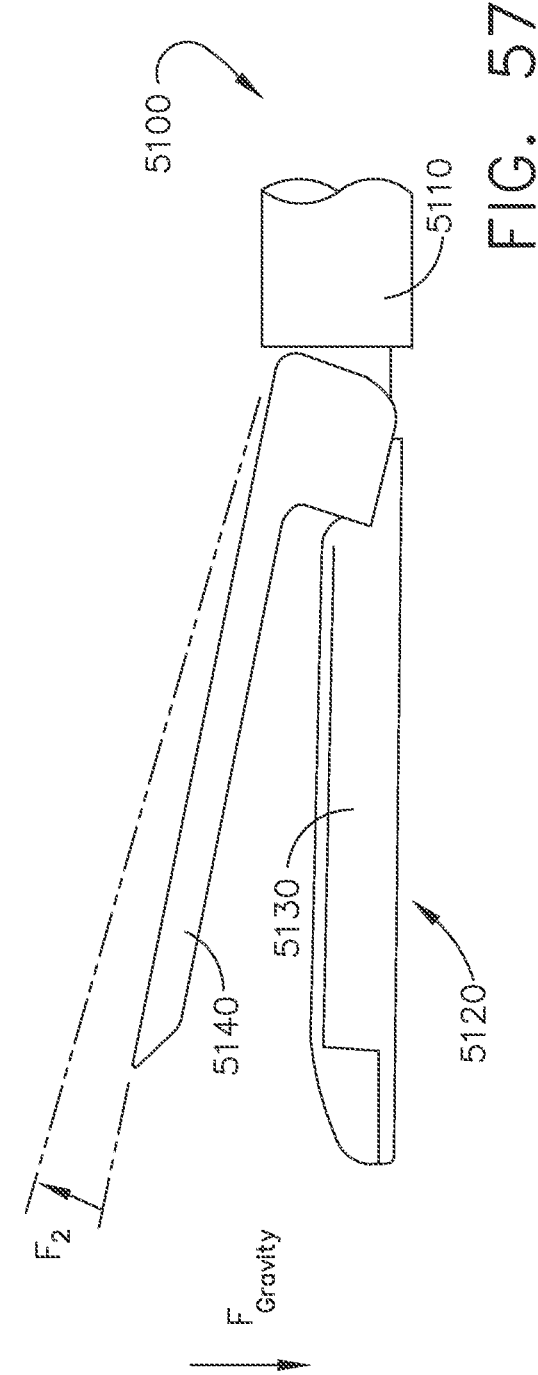

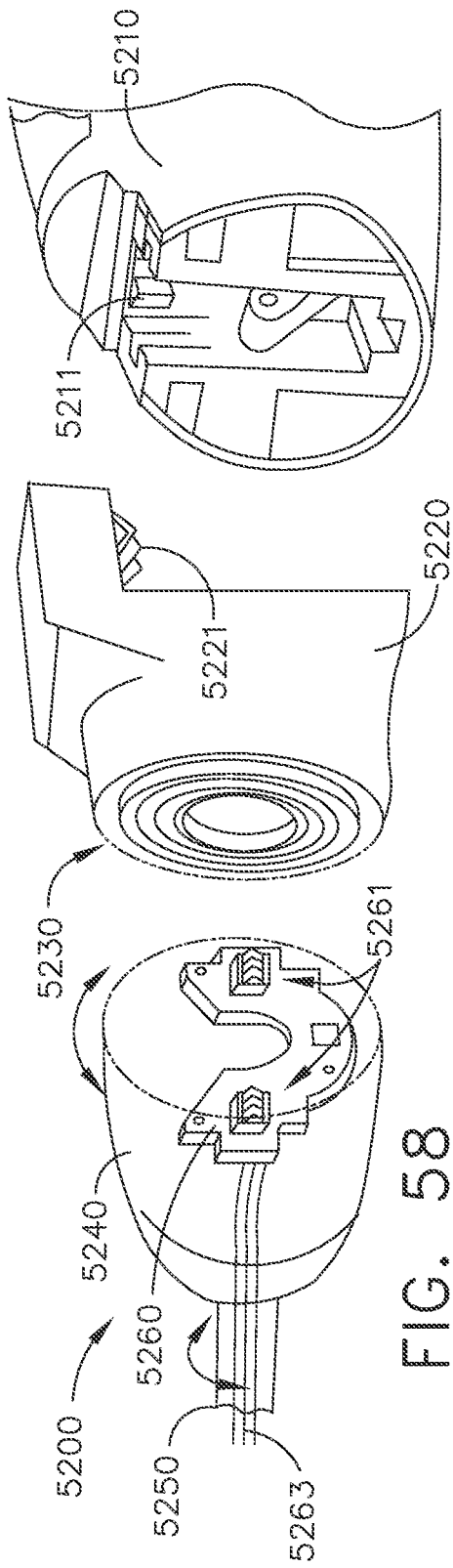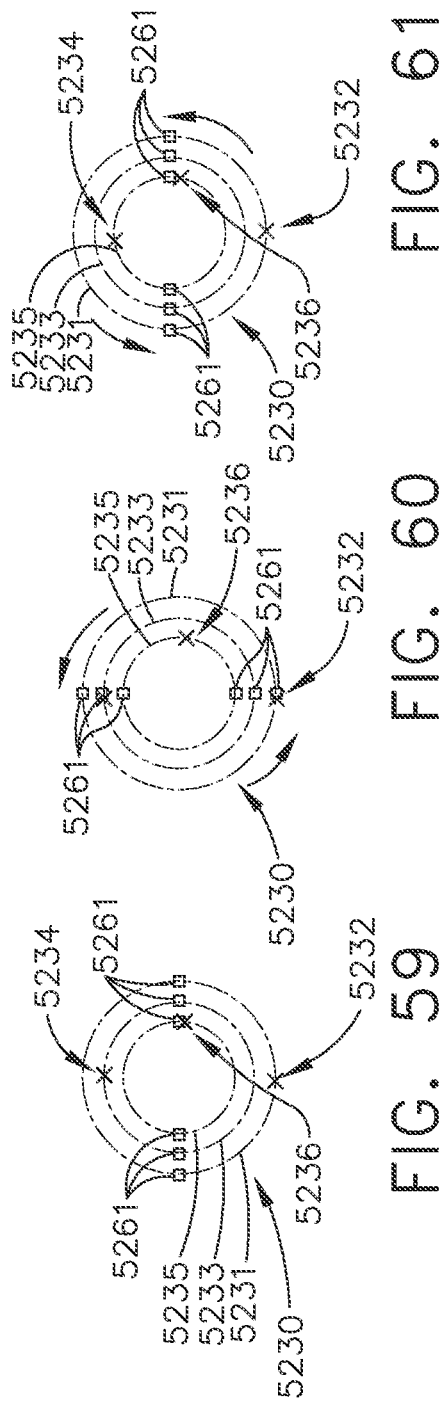
FIG. 58
FIG. 59
FIG. 60
FIG. 61

SURGICAL INSTRUMENT COMPRISING A SIGNAL INTERFERENCE RESOLUTION SYSTEM

CROSS-REFERENCE TO RELATED APPLICATION

This application is a divisional application claiming priority under 35 U.S.C. § 121 to U.S. patent application Ser. No. 16/895,291, entitled SURGICAL INSTRUMENT COMPRISING A SIGNAL INTERFERENCE RESOLUTION SYSTEM, filed Jun. 8, 2020, which issued as U.S. Pat. No. 11,812,957 on Nov. 14, 2023, which claims priority under 35 U.S.C. § 119(e) to U.S. Provisional Patent Application Ser. No. 62/955,306, entitled SURGICAL INSTRUMENT SYSTEMS, filed Dec. 30, 2019, the disclosure of which is incorporated by reference in its entirety.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 1 is a plan view of a surgical instrument assembly comprising a shaft, an end effector attached to the shaft, and a stretchable optical waveguide attached to the shaft and a firing member;

FIG. 2 is a partial perspective view of the surgical instrument assembly of FIG. 1 illustrated with components removed;

FIG. 4 is an elevational view of a surgical instrument assembly comprising the shaft and the end effector of FIG. 1 and a stretchable optical waveguide attached to the end effector and the knife body, wherein the knife body is illustrated in a home position;

FIG. 5 is an elevational view of the surgical instrument assembly of FIG. 4, wherein the knife body is illustrated in an end-of-stroke position;

FIG. 6 is an elevational view of the surgical instrument assembly of FIG. 4, wherein the end effector is articulated relative to the shaft;

FIG. 19 is a perspective view of a surgical instrument assembly, illustrated with components removed, comprising a shaft and a flex circuit extending through the shaft, wherein the flex circuit comprises a pre-bent section;

FIG. 20 is a cross-sectional view of the flex circuit of FIG. 19;

FIG. 21 is a perspective view of a surgical instrument assembly, illustrated with components removed, comprising a shaft and a flex circuit extending through the shaft, wherein the flex circuit comprises a pre-bent section;

FIG. 22 is a cross-sectional view of the flex circuit of FIG. 21;

FIG. 23 is a perspective view of a surgical instrument assembly, illustrated with components removed, comprising a shaft and a flex circuit extending through the shaft, wherein the flex circuit comprises a pre-bent section;

FIG. 24 is a cross-sectional view of the flex circuit of FIG. 23;

FIG. 31 is a perspective view of a surgical instrument assembly, illustrated with components removed, comprising an end effector jaw comprising a staple cartridge channel configured to receive a staple cartridge therein and a sensing system comprising a plurality of pressure sensors;

FIG. 32 is a cross-sectional view of the surgical instrument assembly of FIG. 31 illustrating a staple cartridge positioned within the end effector jaw;

FIG. 33 is a cross-sectional view of the surgical instrument assembly of FIG. 31 illustrating a staple cartridge positioned within the end effector jaw;

FIG. 54 is a partial perspective view of a surgical instrument assembly oriented in an upright orientation;

FIG. 55 is a partial perspective view of the surgical instrument assembly of FIG. 54 in an inverted orientation;

FIG. 56 is an elevational view of an end effector assembly comprising an anvil jaw and a cartridge jaw, wherein the end effector assembly is oriented in a direction where the anvil is opened in a direction which cooperates with gravity;

FIG. 57 is an elevational view of the end effector assembly of FIG. 56, wherein the end effector is oriented in a direction where the anvil is opened in a direction which opposes gravity;

FIG. 58 is a partial exploded perspective view of a surgical instrument assembly comprising an attachment interface, a shaft assembly attachable to the attachment interface, and a sensing system configured to detect the orientation of the shaft assembly relative to the attachment interface;

FIG. 59 is a schematic representation of the sensing system of FIG. 58, wherein the shaft assembly is oriented in a first orientation;

FIG. 60 is a schematic representation of the sensing system of FIG. 58, wherein the shaft assembly is oriented in a second orientation;

FIG. 61 is a schematic representation of the sensing system of FIG. 58, wherein the shaft assembly is oriented in a third orientation;

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

Figure 3:
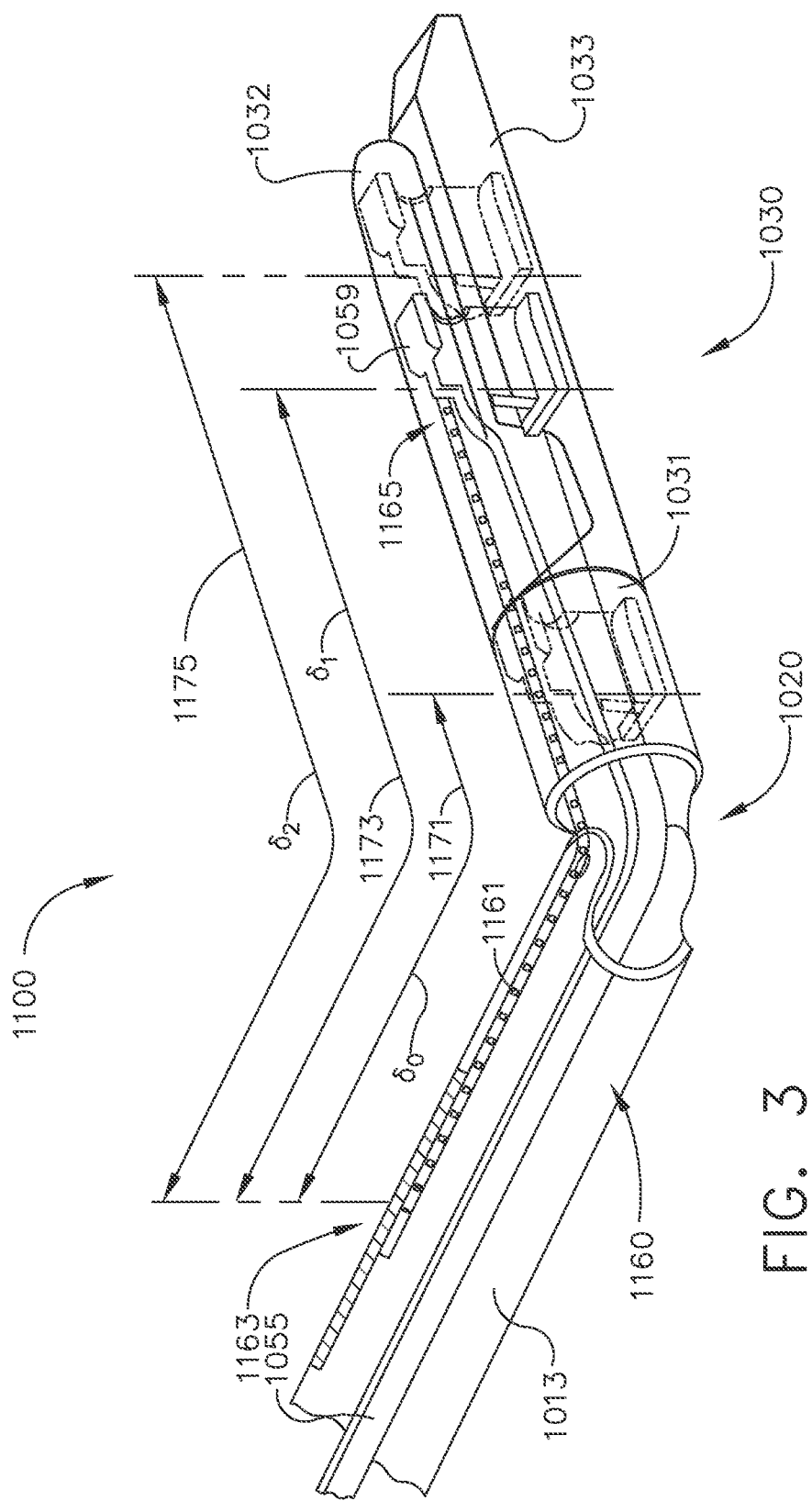
FIG. 3 is a perspective view of a surgical instrument assembly comprising the shaft and the end effector of FIG. 1 and a stretchable optical waveguide attached to the shaft and a knife body.

Applicant of the present application owns the following U.S. Patent Applications that were filed on Jun. 8, 2020, and which are each herein incorporated by reference in their respective entireties:

U.S. patent application Ser. No. 16/895,264, entitled METHOD FOR OPERATING A SURGICAL INSTRUMENT, now U.S. Patent Application Publication No. 2021/0196302;

U.S. patent application Ser. No. 16/895,273, entitled SURGICAL INSTRUMENT COMPRISING AN ADJUSTMENT SYSTEM, now U.S. Pat. No. 11,452,525;

U.S. patent application Ser. No. 16/895,276, entitled SURGICAL INSTRUMENT COMPRISING A CONTROL SYSTEM RESPONSIVE TO SOFTWARE CONFIGURATIONS, now U.S. Patent Application Publication No. 2021/0196266;

U.S. patent application Ser. No. 16/895,284, entitled SURGICAL INSTRUMENT COMPRISING AN ORIENTATION DETECTION SYSTEM, now U.S. Patent Application Publication No. 2021/0196267;

U.S. patent application Ser. No. 16/895,298, entitled SURGICAL INSTRUMENT COMPRISING A FEEDBACK CONTROL CIRCUIT, now U.S. Patent Application Publication No. 2021/0196269;

U.S. patent application Ser. No. 16/895,307, entitled SURGICAL INSTRUMENT COMPRISING A FLEX CIRCUIT, now U.S. Patent Application Publication No. 2021/0196270;

U.S. patent application Ser. No. 16/895,312, entitled SURGICAL INSTRUMENT COMPRISING A SENSING SYSTEM, now U.S. Patent Application Publication No. 2021/0196263; and U.S. patent application Ser. No. 16/895,315, entitled SURGICAL INSTRUMENT COMPRISING A FLEX CIRCUIT INCLUDING A SENSOR SYSTEM, now U.S. Patent Application Publication No. 2021/0196271.

Applicant of the present application owns the following U.S. Patent Applications that were filed on May 29, 2020, and which are each herein incorporated by reference in their respective entireties:

U.S. patent application Ser. No. 16/887,499, entitled USER INTERFACE FOR SURGICAL INSTRUMENT WITH COMBINATION ENERGY MODALITY END-EFFECTOR;

U.S. patent application Ser. No. 16/887,493, entitled METHOD OF OPERATING A COMBINATION ULTRASONIC/BIPOLAR RF SURGICAL DEVICE WITH A COMBINATION ENERGY MODALITY END-EFFECTOR;

U.S. patent application Ser. No. 16/887,506, entitled DEFLECTABLE SUPPORT OF RF ENERGY ELECTRODE WITH RESPECT TO OPPOSING ULTRASONIC BLADE;

U.S. patent application Ser. No. 16/887,515, entitled NON-BIASED DEFLECTABLE ELECTRODE TO MINIMIZE CONTACT BETWEEN ULTRASONIC BLADE AND ELECTRODE;

U.S. patent application Ser. No. 16/887,519, entitled DEFLECTABLE ELECTRODE WITH HIGHER DISTAL BIAS RELATIVE TO PROXIMAL BIAS;

U.S. patent application Ser. No. 16/887,532, entitled DEFLECTABLE ELECTRODE WITH VARIABLE COMPRESSION BIAS ALONG THE LENGTH OF THE DEFLECTABLE ELECTRODE;

U.S. patent application Ser. No. 16/887,554, entitled ASYMMETRIC SEGMENTED ULTRASONIC SUPPORT PAD FOR COOPERATIVE ENGAGEMENT WITH A MOVABLE RF ELECTRODE;

U.S. patent application Ser. No. 16/887,561, entitled VARIATION IN ELECTRODE PARAMETERS AND DEFLECTABLE ELECTRODE TO MODIFY ENERGY DENSITY AND TISSUE INTERACTION;

U.S. patent application Ser. No. 16/887,568, entitled TECHNIQUES FOR DETECTING ULTRASONIC BLADE TO ELECTRODE CONTACT AND REDUCING POWER TO ULTRASONIC BLADE;

U.S. patent application Ser. No. 16/887,576, entitled CLAMP ARM JAW TO MINIMIZE TISSUE STICKING AND IMPROVE TISSUE CONTROL; and U.S. patent application Ser. No. 16/887,579, entitled PARTIALLY CONDUCTIVE CLAMP ARM PAD TO ENABLE ELECTRODE WEAR THROUGH AND MINIMIZE SHORT CIRCUITING.

Applicant of the present application owns the following U.S. Patent Applications that were filed on May 28, 2020, and which are each herein incorporated by reference in their respective entireties:

U.S. patent application Ser. No. 16/885,813, entitled METHOD FOR AN ELECTROSURGICAL PROCEDURE;

U.S. patent application Ser. No. 16/885,820, entitled ARTICULATABLE SURGICAL INSTRUMENT;

U.S. patent application Ser. No. 16/885,823, entitled SURGICAL INSTRUMENT WITH JAW ALIGNMENT FEATURES;

U.S. patent application Ser. No. 16/885,826, entitled SURGICAL INSTRUMENT WITH ROTATABLE AND ARTICULATABLE SURGICAL END EFFECTOR;

U.S. patent application Ser. No. 16/885,838, entitled ELECTROSURGICAL INSTRUMENT WITH ASYNCHRONOUS ENERGIZING ELECTRODES;

U.S. patent application Ser. No. 16/885,851, entitled ELECTROSURGICAL INSTRUMENT WITH ELECTRODES BIASING SUPPORT;

U.S. patent application Ser. No. 16/885,860, entitled ELECTROSURGICAL INSTRUMENT WITH FLEXIBLE WIRING ASSEMBLIES;

U.S. patent application Ser. No. 16/885,866, entitled ELECTROSURGICAL INSTRUMENT WITH VARIABLE CONTROL MECHANISMS;

U.S. patent application Ser. No. 16/885,870, entitled ELECTROSURGICAL SYSTEMS WITH INTEGRATED AND EXTERNAL POWER SOURCES;

U.S. patent application Ser. No. 16/885,873, entitled ELECTROSURGICAL INSTRUMENTS WITH ELECTRODES HAVING ENERGY FOCUSING FEATURES;

U.S. patent application Ser. No. 16/885,879, entitled ELECTROSURGICAL INSTRUMENTS WITH ELECTRODES HAVING VARIABLE ENERGY DENSITIES;

U.S. patent application Ser. No. 16/885,881, entitled ELECTROSURGICAL INSTRUMENT WITH MONOPOLAR AND BIPOLAR ENERGY CAPABILITIES;

U.S. patent application Ser. No. 16/885,888, entitled ELECTROSURGICAL END EFFECTORS WITH THERMALLY INSULATIVE AND THERMALLY CONDUCTIVE PORTIONS;

U.S. patent application Ser. No. 16/885,893, entitled ELECTROSURGICAL INSTRUMENT WITH ELECTRODES OPERABLE IN BIPOLAR AND MONOPOLAR MODES;

U.S. patent application Ser. No. 16/885,900, entitled ELECTROSURGICAL INSTRUMENT FOR DELIVERING BLENDED ENERGY MODALITIES TO TISSUE;

U.S. patent application Ser. No. 16/885,917, entitled CONTROL PROGRAM ADAPTATION BASED ON DEVICE STATUS AND USER INPUT;

U.S. patent application Ser. No. 16/885,923, entitled CONTROL PROGRAM FOR MODULAR COMBINATION ENERGY DEVICE; and U.S. patent application Ser. No. 16/885,931, entitled SURGICAL SYSTEM COMMUNICATION PATHWAYS.

Applicant of the present application owns the following U.S. Provisional Patent Applications that were filed on Dec. 30, 2019 and which are each incorporated by reference in their respective entireties:

U.S. Provisional Patent Application Ser. No. 62/955,294, entitled USER INTERFACE FOR SURGICAL INSTRUMENT WITH COMBINATION ENERGY MODALITY END-EFFECTOR;

U.S. Provisional Patent Application Ser. No. 62/955,292, entitled COMBINATION ENERGY MODALITY END-EFFECTOR; and U.S. Provisional Patent Application Ser. No. 62/955,299, entitled ELECTROSURGICAL INSTRUMENTS FOR COMBINATION ENERGY DELIVERY.

Applicant of the present application owns the following U.S. Patent Applications that were filed on Dec. 19, 2019 and which are each incorporated by reference in their respective entireties:

U.S. patent application Ser. No. 16/720,766, entitled METHOD FOR OPERATING A SURGICAL INSTRUMENT;

U.S. patent application Ser. No. 16/720,706, entitled STAPLE CARTRIDGE COMPRISING A SEATING CAM;

U.S. patent application Ser. No. 16/720,731, entitled SURGICAL INSTRUMENT COMPRISING A RAPID CLOSURE MECHANISM;

U.S. patent application Ser. No. 16/720,735, entitled SURGICAL INSTRUMENT COMPRISING A CLOSURE SYSTEM INCLUDING A CLOSURE MEMBER AND AN OPENING MEMBER DRIVEN BY A DRIVE SCREW;

U.S. patent application Ser. No. 16/720,747, entitled SURGICAL INSTRUMENT COMPRISING A NESTED FIRING MEMBER;

U.S. patent application Ser. No. 16/720,751, entitled STAPLE CARTRIDGE COMPRISING A DEPLOYABLE KNIFE;

U.S. patent application Ser. No. 16/720,769, entitled STAPLE CARTRIDGE COMPRISING A DETACHABLE TISSUE CUTTING KNIFE;

U.S. patent application Ser. No. 16/720,730, entitled STAPLING SYSTEM COMPRISING A CLAMP LOCKOUT AND A FIRING LOCKOUT;

U.S. patent application Ser. No. 16/720,742, entitled STAPLE CARTRIDGE COMPRISING A LATCH LOCKOUT;

U.S. patent application Ser. No. 16/720,776, entitled SURGICAL INSTRUMENT COMPRISING A POWERED ARTICULATION SYSTEM;

U.S. patent application Ser. No. 16/720,781, entitled MOTOR DRIVEN SURGICAL INSTRUMENT;

U.S. patent application Ser. No. 16/720,789, entitled STAPLING INSTRUMENT COMPRISING INDEPENDENT JAW CLOSING AND STAPLE FIRING SYSTEMS;

U.S. patent application Ser. No. 16/720,725, entitled STAPLE CARTRIDGE COMPRISING DRIVER RETENTION MEMBERS;

U.S. patent application Ser. No. 16/720,740, entitled STAPLE CARTRIDGE COMPRISING DRIVER RETENTION MEMBERS;

U.S. patent application Ser. No. 16/720,788, entitled STAPLE CARTRIDGE COMPRISING PROJECTIONS EXTENDING FROM A CURVED DECK SURFACE; and U.S. patent application Ser. No. 16/720,806, entitled STAPLE CARTRIDGE COMPRISING A CURVED DECK SURFACE.

Applicant of the present application owns the following U.S. Patent Applications that were filed on Sep. 5, 2019 and which are each herein incorporated by reference in their respective entireties:

U.S. patent application Ser. No. 16/562,123, entitled METHOD FOR CONSTRUCTING AND USING A MODULAR SURGICAL ENERGY SYSTEM WITH MULTIPLE DEVICES;

U.S. patent application Ser. No. 16/562,135, entitled METHOD FOR CONTROLLING AN ENERGY MODULE OUTPUT;

U.S. patent application Ser. No. 16/562,144, entitled METHOD FOR CONTROLLING A MODULAR ENERGY SYSTEM USER INTERFACE; and U.S. patent application Ser. No. 16/562,125, entitled METHOD FOR COMMUNICATING BETWEEN MODULES AND DEVICES IN A MODULAR SURGICAL SYSTEM.

Applicant of the present application owns the following U.S. Patent Applications that were filed on Mar. 25, 2019 and which are each herein incorporated by reference in their respective entireties:

U.S. patent application Ser. No. 16/363,070, entitled FIRING DRIVE ARRANGEMENTS FOR SURGICAL SYSTEMS;

U.S. patent application Ser. No. 16/363,051, entitled FIRING DRIVE ARRANGEMENTS FOR SURGICAL SYSTEMS;

U.S. patent application Ser. No. 16/363,045, entitled ARTICULATION DRIVE ARRANGEMENTS FOR SURGICAL SYSTEMS; and U.S. patent application Ser. No. 16/363,062, entitled FIRING DRIVE ARRANGEMENTS FOR SURGICAL SYSTEMS.

Applicant of the present application owns the following U.S. Patent Applications that were filed on Jun. 30, 2019 and which are each herein incorporated by reference in their respective entireties:

U.S. patent application Ser. No. 16/458,104, entitled METHOD FOR AUTHENTICATING THE COMPATIBILITY OF A STAPLE CARTRIDGE WITH A SURGICAL INSTRUMENT;

U.S. patent application Ser. No. 16/458,108, entitled SURGICAL INSTRUMENT SYSTEM COMPRISING AN RFID SYSTEM;

U.S. patent application Ser. No. 16/458,111, entitled SURGICAL INSTRUMENT COMPRISING AN RFID SYSTEM FOR TRACKING A MOVABLE COMPONENT;

U.S. patent application Ser. No. 16/458,114, entitled SURGICAL INSTRUMENT COMPRISING AN ALIGNED RFID SENSOR;

U.S. patent application Ser. No. 16/458,105, entitled SURGICAL STAPLING SYSTEM HAVING AN INFORMATION DECRYPTION PROTOCOL;

U.S. patent application Ser. No. 16/458,110, entitled SURGICAL STAPLING SYSTEM HAVING AN INFORMATION ENCRYPTION PROTOCOL;

U.S. patent application Ser. No. 16/458,120, entitled SURGICAL STAPLING SYSTEM HAVING A LOCKOUT MECHANISM FOR AN INCOMPATIBLE CARTRIDGE;

U.S. patent application Ser. No. 16/458,125, entitled SURGICAL STAPLING SYSTEM HAVING A FRANGIBLE RFID TAG; and U.S. patent application Ser. No. 16/458,103, entitled PACKAGING FOR A REPLACEABLE COMPONENT OF A SURGICAL STAPLING SYSTEM.

Applicant of the present application owns the following U.S. Patent Applications that were filed on Jun. 30, 2019 and which are each herein incorporated by reference in their respective entireties:

U.S. patent application Ser. No. 16/458,107, entitled METHOD OF USING MULTIPLE RFID CHIPS WITH A SURGICAL ASSEMBLY;

U.S. patent application Ser. No. 16/458,109, entitled MECHANISMS FOR PROPER ANVIL ATTACHMENT SURGICAL STAPLING HEAD ASSEMBLY;

U.S. patent application Ser. No. 16/458,119, entitled MECHANISMS FOR MOTOR CONTROL ADJUSTMENTS OF A MOTORIZED SURGICAL INSTRUMENT;

U.S. patent application Ser. No. 16/458,115, entitled SURGICAL INSTRUMENT WITH BATTERY COMPATIBILITY VERIFICATION FUNCTIONALITY;

U.S. patent application Ser. No. 16/458,117, entitled SURGICAL SYSTEM WITH RFID TAGS FOR UPDATING MOTOR ASSEMBLY PARAMETERS;

U.S. patent application Ser. No. 16/458,121, entitled SURGICAL SYSTEMS WITH MULTIPLE RFID TAGS;

U.S. patent application Ser. No. 16/458,122, entitled RFID IDENTIFICATION SYSTEMS FOR SURGICAL INSTRUMENTS;

U.S. patent application Ser. No. 16/458,106, entitled RFID IDENTIFICATION SYSTEMS FOR SURGICAL INSTRUMENTS;

U.S. patent application Ser. No. 16/458,112, entitled SURGICAL RFID ASSEMBLIES FOR DISPLAY AND COMMUNICATION;

U.S. patent application Ser. No. 16/458,116, entitled SURGICAL RFID ASSEMBLIES FOR COMPATIBILITY DETECTION; and U.S. patent application Ser. No. 16/458,118, entitled SURGICAL RFID ASSEMBLIES FOR INSTRUMENT OPERATIONAL SETTING CONTROL.

Applicant of the present application owns the following U.S. Patent Applications, filed on Dec. 4, 2018, the disclosure of each of which is herein incorporated by reference in its entirety:

U.S. patent application Ser. No. 16/209,385, entitled METHOD OF HUB COMMUNICATION, PROCESSING, STORAGE AND DISPLAY;

U.S. patent application Ser. No. 16/209,395, entitled METHOD OF HUB COMMUNICATION;

U.S. patent application Ser. No. 16/209,403, entitled METHOD OF CLOUD BASED DATA ANALYTICS FOR USE WITH THE HUB;

U.S. patent application Ser. No. 16/209,407, entitled METHOD OF ROBOTIC HUB COMMUNICATION, DETECTION, AND CONTROL;

U.S. patent application Ser. No. 16/209,416, entitled METHOD OF HUB COMMUNICATION, PROCESSING, DISPLAY, AND CLOUD ANALYTICS;

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, entitled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, entitled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, entitled METHOD FOR SMOKE EVACUATION FOR SURGICAL HUB;

U.S. patent application Ser. No. 16/209,453, entitled METHOD FOR CONTROLLING SMART ENERGY DEVICES;

U.S. patent application Ser. No. 16/209,458, entitled METHOD FOR SMART ENERGY DEVICE INFRASTRUCTURE;

U.S. patent application Ser. No. 16/209,465, entitled METHOD FOR ADAPTIVE CONTROL SCHEMES FOR SURGICAL NETWORK CONTROL AND INTERACTION;

U.S. patent application Ser. No. 16/209,478, entitled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, entitled METHOD FOR FACILITY DATA COLLECTION AND INTERPRETATION; and U.S. patent application Ser. No. 16/209,491, entitled METHOD FOR CIRCULAR STAPLER CONTROL ALGORITHM ADJUSTMENT BASED ON SITUATIONAL AWARENESS.

Applicant of the present application owns the following U.S. Patent Applications that were filed on Jun. 26, 2019 and which are each herein incorporated by reference in their respective entireties:

U.S. patent application Ser. No. 16/453,273, entitled METHOD FOR PROVIDING AN AUTHENTICATION LOCKOUT IN A SURGICAL STAPLER WITH A REPLACEABLE CARTRIDGE;

U.S. patent application Ser. No. 16/453,283, entitled SURGICAL STAPLING ASSEMBLY WITH CARTRIDGE BASED RETAINER CONFIGURED TO UNLOCK A FIRING LOCKOUT;

U.S. patent application Ser. No. 16/453,289, entitled SURGICAL STAPLING ASSEMBLY WITH CARTRIDGE BASED RETAINER CONFIGURED TO UNLOCK A CLOSURE LOCKOUT;

U.S. patent application Ser. No. 16/453,302 entitled UNIVERSAL CARTRIDGE BASED KEY FEATURE THAT UNLOCKS MULTIPLE LOCKOUT ARRANGEMENTS IN DIFFERENT SURGICAL STAPLERS;

U.S. patent application Ser. No. 16/453,310, entitled STAPLE CARTRIDGE RETAINERS WITH FRANGIBLE RETENTION FEATURES AND METHODS OF USING SAME;

U.S. patent application Ser. No. 16/453,330, entitled STAPLE CARTRIDGE RETAINER WITH FRANGIBLE AUTHENTICATION KEY;

U.S. patent application Ser. No. 16/453,335, entitled STAPLE CARTRIDGE RETAINER WITH RETRACTABLE AUTHENTICATION KEY;

U.S. patent application Ser. No. 16/453,343, entitled STAPLE CARTRIDGE RETAINER SYSTEM WITH AUTHENTICATION KEYS;

U.S. patent application Ser. No. 16/453,355, entitled INSERTABLE DEACTIVATOR ELEMENT FOR SURGICAL STAPLER LOCKOUTS;

U.S. patent application Ser. No. 16/453,369, entitled DUAL CAM CARTRIDGE BASED FEATURE FOR UNLOCKING A SURGICAL STAPLER LOCKOUT;

U.S. patent application Ser. No. 16/453,391, entitled STAPLE CARTRIDGES WITH CAM SURFACES CONFIGURED TO ENGAGE PRIMARY AND SECONDARY PORTIONS OF A LOCKOUT OF A SURGICAL STAPLING DEVICE;

U.S. patent application Ser. No. 16/453,413, entitled SURGICAL STAPLE CARTRIDGES WITH MOVABLE AUTHENTICATION KEY ARRANGEMENTS;

U.S. patent application Ser. No. 16/453,423, entitled DEACTIVATOR ELEMENT FOR DEFEATING SURGICAL STAPLING DEVICE LOCKOUTS; and U.S. patent application Ser. No. 16/453,429 entitled SURGICAL STAPLE CARTRIDGES WITH INTEGRAL AUTHENTICATION KEYS.

Applicant of the present application owns the following U.S. Design Patent Applications that were filed on Jun. 25, 2019 which are each herein incorporated by reference in their respective entireties:

U.S. Design patent application Ser. No. 29/696,066, entitled SURGICAL STAPLE CARTRIDGE RETAINER WITH FIRING SYSTEM AUTHENTICATION KEY;

U.S. Design patent application Ser. No. 29/696,067, entitled SURGICAL STAPLE CARTRIDGE RETAINER WITH CLOSURE SYSTEM AUTHENTICATION KEY; and U.S. Design patent application Ser. No. 29/696,072, entitled SURGICAL STAPLE CARTRIDGE.

Applicant of the present application owns the following U.S. Patent Applications that were filed on Feb. 21, 2019 which are each herein incorporated by reference in their respective entireties:

U.S. patent application Ser. No. 16/281,658, entitled METHODS FOR CONTROLLING A POWERED SURGICAL STAPLER THAT HAS SEPARATE ROTARY CLOSURE AND FIRING SYSTEMS;

U.S. patent application Ser. No. 16/281,670, entitled STAPLE CARTRIDGE COMPRISING A LOCKOUT KEY CONFIGURED TO LIFT A FIRING MEMBER;

U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN;

U.S. patent application Ser. No. 16/281,685, entitled SURGICAL INSTRUMENT COMPRISING CO-OPERATING LOCKOUT FEATURES;

U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT;

U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN;

U.S. patent application Ser. No. 16/281,707, entitled SURGICAL INSTRUMENT COMPRISING A DEACTIVATABLE LOCKOUT;

U.S. patent application Ser. No. 16/281,741, entitled SURGICAL INSTRUMENT COMPRISING A JAW CLOSURE LOCKOUT;

U.S. patent application Ser. No. 16/281,762, entitled SURGICAL STAPLING DEVICES WITH CARTRIDGE COMPATIBLE CLOSURE AND FIRING LOCKOUT ARRANGEMENTS;

U.S. patent application Ser. No. 16/281,660, entitled SURGICAL STAPLE CARTRIDGE WITH FIRING MEMBER DRIVEN CAMMING ASSEMBLY THAT HAS AN ONBOARD TISSUE CUTTING FEATURE;

U.S. patent application Ser. No. 16/281,666, entitled SURGICAL STAPLING DEVICES WITH IMPROVED ROTARY DRIVEN CLOSURE SYSTEMS;

U.S. patent application Ser. No. 16/281,672, entitled SURGICAL STAPLING DEVICES WITH ASYMMETRIC CLOSURE FEATURES;

U.S. patent application Ser. No. 16/281,678, entitled ROTARY DRIVEN FIRING MEMBERS WITH DIFFERENT ANVIL AND FRAME ENGAGEMENT FEATURES; and U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-

BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Application, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Application, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS.

Applicant of the present application owns the following U.S. Patent Applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS;

U.S. patent application Ser. No. 16/105,183, entitled REINFORCED DEFORMABLE ANVIL TIP FOR SURGICAL STAPLER ANVIL;

U.S. patent application Ser. No. 16/105,150, entitled SURGICAL STAPLER ANVILS WITH STAPLE DIRECTING PROTRUSIONS AND TISSUE STABILITY FEATURES;

U.S. patent application Ser. No. 16/105,098, entitled FABRICATING TECHNIQUES FOR SURGICAL STAPLER ANVILS;

U.S. patent application Ser. No. 16/105,140, entitled SURGICAL STAPLER ANVILS WITH TISSUE STOP FEATURES CONFIGURED TO AVOID TISSUE PINCH;

U.S. patent application Ser. No. 16/105,081, entitled METHOD FOR OPERATING A POWERED ARTICULATABLE SURGICAL INSTRUMENT;

U.S. patent application Ser. No. 16/105,094, entitled SURGICAL INSTRUMENTS WITH PROGRESSIVE JAW CLOSURE ARRANGEMENTS;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM;

U.S. patent application Ser. No. 16/105,119, entitled ARTICULATABLE MOTOR POWERED SURGICAL INSTRUMENTS WITH DEDICATED ARTICULATION MOTOR ARRANGEMENTS;

U.S. patent application Ser. No. 16/105,160, entitled SWITCHING ARRANGEMENTS FOR MOTOR POWERED ARTICULATABLE SURGICAL INSTRUMENTS; and U.S. Design patent application Ser. No. 29/660,252, entitled SURGICAL STAPLER ANVILS.

Applicant of the present application owns the following U.S. Patent Applications that were filed on Aug. 3, 2017 and which are each herein incorporated by reference in their respective entireties:

U.S. patent application Ser. No. 15/668,324, entitled SURGICAL SYSTEM SHAFT INTERCONNECTION;

U.S. patent application Ser. No. 15/668,301, entitled SURGICAL SYSTEM BAILOUT; and U.S. patent application Ser. No. 15/668,319, entitled SURGICAL SYSTEM COMPRISING AN ARTICULATION BAILOUT.

Applicant of the present application owns the following U.S. Patent Applications that were filed on Jun. 28, 2017 and which are each herein incorporated by reference in their respective entireties:

U.S. patent application Ser. No. 15/635,693, entitled SURGICAL INSTRUMENT COMPRISING AN OFFSET ARTICULATION JOINT;

U.S. patent application Ser. No. 15/635,729, entitled SURGICAL INSTRUMENT COMPRISING AN ARTICULATION SYSTEM RATIO;

U.S. patent application Ser. No. 15/635,785, entitled SURGICAL INSTRUMENT COMPRISING AN ARTICULATION SYSTEM RATIO;

U.S. patent application Ser. No. 15/635,808, entitled SURGICAL INSTRUMENT COMPRISING FIRING MEMBER SUPPORTS;

U.S. patent application Ser. No. 15/635,837, entitled SURGICAL INSTRUMENT COMPRISING AN ARTICULATION SYSTEM LOCKABLE TO A FRAME;

U.S. patent application Ser. No. 15/635,941, entitled SURGICAL INSTRUMENT COMPRISING AN ARTICULATION SYSTEM LOCKABLE BY A CLOSURE SYSTEM;

U.S. patent application Ser. No. 15/636,029, entitled SURGICAL INSTRUMENT COMPRISING A SHAFT INCLUDING A HOUSING ARRANGEMENT;

U.S. patent application Ser. No. 15/635,958, entitled SURGICAL INSTRUMENT COMPRISING SELECTIVELY ACTUATABLE ROTATABLE COUPLERS;

U.S. patent application Ser. No. 15/635,981, entitled SURGICAL STAPLING INSTRUMENTS COMPRISING SHORTENED STAPLE CARTRIDGE NOSES;

U.S. patent application Ser. No. 15/636,009, entitled SURGICAL INSTRUMENT COMPRISING A SHAFT INCLUDING A CLOSURE TUBE PROFILE;

U.S. patent application Ser. No. 15/635,663, entitled METHOD FOR ARTICULATING A SURGICAL INSTRUMENT;

U.S. patent application Ser. No. 15/635,530, entitled SURGICAL INSTRUMENTS WITH ARTICULATABLE END EFFECTOR WITH AXIALLY SHORTENED ARTICULATION JOINT CONFIGURATIONS;

U.S. patent application Ser. No. 15/635,549, entitled SURGICAL INSTRUMENTS WITH OPEN AND CLOSABLE JAWS AND AXIALLY MOVABLE FIRING MEMBER THAT IS INITIALLY PARKED IN CLOSE PROXIMITY TO THE JAWS PRIOR TO FIRING;

U.S. patent application Ser. No. 15/635,559, entitled SURGICAL INSTRUMENTS WITH JAWS CONSTRAINED TO PIVOT ABOUT AN AXIS UPON CONTACT WITH A CLOSURE MEMBER THAT IS PARKED IN CLOSE PROXIMITY TO THE PIVOT AXIS;

U.S. patent application Ser. No. 15/635,578, entitled SURGICAL END EFFECTORS WITH IMPROVED JAW APERTURE ARRANGEMENTS;

U.S. patent application Ser. No. 15/635,594, entitled SURGICAL CUTTING AND FASTENING DEVICES WITH PIVOTABLE ANVIL WITH A TISSUE LOCATING ARRANGEMENT IN CLOSE PROXIMITY TO AN ANVIL PIVOT AXIS;

U.S. patent application Ser. No. 15/635,612, entitled JAW RETAINER ARRANGEMENT FOR RETAINING A PIVOTABLE SURGICAL INSTRUMENT JAW IN PIVOTABLE RETAINING ENGAGEMENT WITH A SECOND SURGICAL INSTRUMENT JAW;

U.S. patent application Ser. No. 15/635,621, entitled SURGICAL INSTRUMENT WITH POSITIVE JAW OPENING FEATURES;

U.S. patent application Ser. No. 15/635,631, entitled SURGICAL INSTRUMENT WITH AXIALLY MOVABLE CLOSURE MEMBER;

U.S. patent application Ser. No. 15/635,521, entitled SURGICAL INSTRUMENT LOCKOUT ARRANGEMENT;

U.S. Design patent application Ser. No. 29/609,083, entitled SURGICAL INSTRUMENT SHAFT;

U.S. Design patent application Ser. No. 29/609,087, entitled SURGICAL FORMING ANVIL;

U.S. Design patent application Ser. No. 29/609,093, entitled SURGICAL FASTENER CARTRIDGE;

U.S. Design patent application Ser. No. 29/609,121, entitled SURGICAL INSTRUMENT;

U.S. Design patent application Ser. No. 29/609,125, entitled SURGICAL INSTRUMENT;

U.S. Design patent application Ser. No. 29/609,128, entitled SURGICAL INSTRUMENT; and U.S. Design patent application Ser. No. 29/609,129, entitled DISPLAY SCREEN PORTION OF A SURGICAL INSTRUMENT HAVING A GRAPHICAL USER INTERFACE.

Applicant of the present application owns the following U.S. Patent Applications that were filed on Jun. 27, 2017 and which are each herein incorporated by reference in their respective entireties:

U.S. patent application Ser. No. 15/634,024, entitled SURGICAL ANVIL MANUFACTURING METHODS;

U.S. patent application Ser. No. 15/634,035, entitled SURGICAL ANVIL ARRANGEMENTS;

U.S. patent application Ser. No. 15/634,046, entitled SURGICAL ANVIL ARRANGEMENTS;

U.S. patent application Ser. No. 15/634,054, entitled SURGICAL ANVIL ARRANGEMENTS;

U.S. patent application Ser. No. 15/634,068, entitled SURGICAL FIRING MEMBER ARRANGEMENTS;

U.S. patent application Ser. No. 15/634,076, entitled STAPLE FORMING POCKET ARRANGEMENTS;

U.S. patent application Ser. No. 15/634,090, entitled STAPLE FORMING POCKET ARRANGEMENTS;

U.S. patent application Ser. No. 15/634,099, entitled SURGICAL END EFFECTORS AND ANVILS; and U.S. patent application Ser. No. 15/634,117, entitled ARTICULATION SYSTEMS FOR SURGICAL INSTRUMENTS.

Applicant of the present application owns the following U.S. Patent Applications that were filed on Dec. 21, 2016 and which are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF;

U.S. patent application Ser. No. 15/386,230, entitled ARTICULATABLE SURGICAL STAPLING INSTRUMENTS;

U.S. patent application Ser. No. 15/386,221, entitled LOCKOUT ARRANGEMENTS FOR SURGICAL END EFFECTORS;

U.S. patent application Ser. No. 15/386,209, entitled SURGICAL END EFFECTORS AND FIRING MEMBERS THEREOF;

U.S. patent application Ser. No. 15/386,198, entitled LOCKOUT ARRANGEMENTS FOR SURGICAL END EFFECTORS AND REPLACEABLE TOOL ASSEMBLIES;

U.S. patent application Ser. No. 15/386,240, entitled SURGICAL END EFFECTORS AND ADAPTABLE FIRING MEMBERS THEREFOR;

U.S. patent application Ser. No. 15/385,939, entitled STAPLE CARTRIDGES AND ARRANGEMENTS OF STAPLES AND STAPLE CAVITIES THEREIN;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS;

U.S. patent application Ser. No. 15/385,943, entitled SURGICAL STAPLING INSTRUMENTS AND STAPLE-FORMING ANVILS;

U.S. patent application Ser. No. 15/385,950, entitled SURGICAL TOOL ASSEMBLIES WITH CLOSURE STROKE REDUCTION FEATURES;

U.S. patent application Ser. No. 15/385,945, entitled STAPLE CARTRIDGES AND ARRANGEMENTS OF STAPLES AND STAPLE CAVITIES THEREIN;

U.S. patent application Ser. No. 15/385,946, entitled SURGICAL STAPLING INSTRUMENTS AND STAPLE-FORMING ANVILS;

U.S. patent application Ser. No. 15/385,951, entitled SURGICAL INSTRUMENTS WITH JAW OPENING FEATURES FOR INCREASING A JAW OPENING DISTANCE;

U.S. patent application Ser. No. 15/385,953, entitled METHODS OF STAPLING TIS SUE;

U.S. patent application Ser. No. 15/385,954, entitled FIRING MEMBERS WITH NON-PARALLEL JAW ENGAGEMENT FEATURES FOR SURGICAL END EFFECTORS;

U.S. patent application Ser. No. 15/385,955, entitled SURGICAL END EFFECTORS WITH EXPANDABLE TISSUE STOP ARRANGEMENTS;

U.S. patent application Ser. No. 15/385,948, entitled SURGICAL STAPLING INSTRUMENTS AND STAPLE-FORMING ANVILS;

U.S. patent application Ser. No. 15/385,956, entitled SURGICAL INSTRUMENTS WITH POSITIVE JAW OPENING FEATURES;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT;

U.S. patent application Ser. No. 15/385,947, entitled STAPLE CARTRIDGES AND ARRANGEMENTS OF STAPLES AND STAPLE CAVITIES THEREIN;

U.S. patent application Ser. No. 15/385,896, entitled METHOD FOR RESETTING A FUSE OF A SURGICAL INSTRUMENT SHAFT;

U.S. patent application Ser. No. 15/385,898, entitled STAPLE FORMING POCKET ARRANGEMENT TO ACCOMMODATE DIFFERENT TYPES OF STAPLES;

U.S. patent application Ser. No. 15/385,899, entitled SURGICAL INSTRUMENT COMPRISING IMPROVED JAW CONTROL;

U.S. patent application Ser. No. 15/385,901, entitled STAPLE CARTRIDGE AND STAPLE CARTRIDGE CHANNEL COMPRISING WINDOWS DEFINED THEREIN;

U.S. patent application Ser. No. 15/385,902, entitled SURGICAL INSTRUMENT COMPRISING A CUTTING MEMBER;

U.S. patent application Ser. No. 15/385,904, entitled STAPLE FIRING MEMBER COMPRISING A MISSING CARTRIDGE AND/OR SPENT CARTRIDGE LOCKOUT;

U.S. patent application Ser. No. 15/385,905, entitled FIRING ASSEMBLY COMPRISING A LOCKOUT;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT;

U.S. patent application Ser. No. 15/385,908, entitled FIRING ASSEMBLY COMPRISING A FUSE;

U.S. patent application Ser. No. 15/385,909, entitled FIRING ASSEMBLY COMPRISING A MULTIPLE FAILED-STATE FUSE;

U.S. patent application Ser. No. 15/385,920, entitled STAPLE FORMING POCKET ARRANGEMENTS;

U.S. patent application Ser. No. 15/385,913, entitled ANVIL ARRANGEMENTS FOR SURGICAL STAPLE/FASTENERS;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT;

U.S. patent application Ser. No. 15/385,893, entitled BILATERALLY ASYMMETRIC STAPLE FORMING POCKET PAIRS;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS;

U.S. patent application Ser. No. 15/385,911, entitled SURGICAL STAPLE/FASTENERS WITH INDEPENDENTLY ACTUATABLE CLOSING AND FIRING SYSTEMS;

U.S. patent application Ser. No. 15/385,927, entitled SURGICAL STAPLING INSTRUMENTS WITH SMART STAPLE CARTRIDGES;

U.S. patent application Ser. No. 15/385,917, entitled STAPLE CARTRIDGE COMPRISING STAPLES WITH DIFFERENT CLAMPING BREADTHS;

U.S. patent application Ser. No. 15/385,900, entitled STAPLE FORMING POCKET ARRANGEMENTS COMPRISING PRIMARY SIDEWALLS AND POCKET SIDEWALLS;

U.S. patent application Ser. No. 15/385,931, entitled NO-CARTRIDGE AND SPENT CARTRIDGE LOCKOUT ARRANGEMENTS FOR SURGICAL STAPLE/FASTENERS;

U.S. patent application Ser. No. 15/385,915, entitled FIRING MEMBER PIN ANGLE;

U.S. patent application Ser. No. 15/385,897, entitled STAPLE FORMING POCKET ARRANGEMENTS COMPRISING ZONED FORMING SURFACE GROOVES;

U.S. patent application Ser. No. 15/385,922, entitled SURGICAL INSTRUMENT WITH MULTIPLE FAILURE RESPONSE MODES;

U.S. patent application Ser. No. 15/385,924, entitled SURGICAL INSTRUMENT WITH PRIMARY AND SAFETY PROCESSORS;

U.S. patent application Ser. No. 15/385,912, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS;

U.S. patent application Ser. No. 15/385,910, entitled ANVIL HAVING A KNIFE SLOT WIDTH;

U.S. patent application Ser. No. 15/385,906, entitled FIRING MEMBER PIN CONFIGURATIONS;

U.S. patent application Ser. No. 15/386,188, entitled STEPPED STAPLE CARTRIDGE WITH ASYMMETRICAL STAPLES;

U.S. patent application Ser. No. 15/386,192, entitled STEPPED STAPLE CARTRIDGE WITH TISSUE RETENTION AND GAP SETTING FEATURES;

U.S. patent application Ser. No. 15/386,206, entitled STAPLE CARTRIDGE WITH DEFORMABLE DRIVER RETENTION FEATURES;

U.S. patent application Ser. No. 15/386,226, entitled DURABILITY FEATURES FOR END EFFECTORS AND FIRING ASSEMBLIES OF SURGICAL STAPLING INSTRUMENTS;

U.S. patent application Ser. No. 15/386,222, entitled SURGICAL STAPLING INSTRUMENTS HAVING END EFFECTORS WITH POSITIVE OPENING FEATURES;

U.S. patent application Ser. No. 15/386,236, entitled CONNECTION PORTIONS FOR DEPOSABLE LOADING UNITS FOR SURGICAL STAPLING INSTRUMENTS;

U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT;

U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM;

U.S. patent application Ser. No. 15/385,890, entitled SHAFT ASSEMBLY COMPRISING SEPARATELY ACTUATABLE AND RETRACTABLE SYSTEMS;

U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS;

U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM;

U.S. patent application Ser. No. 15/385,894, entitled SHAFT ASSEMBLY COMPRISING A LOCKOUT;

U.S. patent application Ser. No. 15/385,895, entitled SHAFT ASSEMBLY COMPRISING FIRST AND SECOND ARTICULATION LOCKOUTS;

U.S. patent application Ser. No. 15/385,916, entitled SURGICAL STAPLING SYSTEMS;

U.S. patent application Ser. No. 15/385,918, entitled SURGICAL STAPLING SYSTEMS;

U.S. patent application Ser. No. 15/385,919, entitled SURGICAL STAPLING SYSTEMS;

U.S. patent application Ser. No. 15/385,921, entitled SURGICAL STAPLE/FASTENER CARTRIDGE WITH MOVABLE CAMMING MEMBER CONFIGURED TO DISENGAGE FIRING MEMBER LOCKOUT FEATURES;

U.S. patent application Ser. No. 15/385,923, entitled SURGICAL STAPLING SYSTEMS;

U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR;

U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS;

U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT;

U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS;

U.S. patent application Ser. No. 15/385,932, entitled ARTICULATABLE SURGICAL END EFFECTOR WITH ASYMMETRIC SHAFT ARRANGEMENT;

U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK;

U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM;

U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION; and U.S. patent application Ser. No. 15/385,936, entitled ARTICULATABLE SURGICAL INSTRUMENTS WITH ARTICULATION STROKE AMPLIFICATION FEATURES.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES;

U.S. patent application Ser. No. 15/191,807, entitled STAPLING SYSTEM FOR USE WITH WIRE STAPLES AND STAMPED STAPLES;

U.S. patent application Ser. No. 15/191,834, entitled STAMPED STAPLES AND STAPLE CARTRIDGES USING THE SAME;

U.S. patent application Ser. No. 15/191,788, entitled STAPLE CARTRIDGE COMPRISING OVERDRIVEN STAPLES; and U.S. patent application Ser. No. 15/191,818, entitled STAPLE CARTRIDGE COMPRISING OFFSET LONGITUDINAL STAPLE ROWS.

Applicant of the present application owns the following U.S. Patent Applications that were filed on Jun. 24, 2016 and which are each herein incorporated by reference in their respective entireties:

U.S. Design patent application Ser. No. 29/569,218, entitled SURGICAL FASTENER;

U.S. Design patent application Ser. No. 29/569,227, entitled SURGICAL FASTENER;

U.S. Design patent application Ser. No. 29/569,259, entitled SURGICAL FASTENER CARTRIDGE; and U.S. Design patent application Ser. No. 29/569,264, entitled SURGICAL FASTENER CARTRIDGE.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM;

U.S. patent application Ser. No. 15/089,321, entitled MODULAR SURGICAL STAPLING SYSTEM COMPRISING A DISPLAY;

U.S. patent application Ser. No. 15/089,326, entitled SURGICAL STAPLING SYSTEM COMPRISING A DISPLAY INCLUDING A RE-ORIENTABLE DISPLAY FIELD;

U.S. patent application Ser. No. 15/089,263, entitled SURGICAL INSTRUMENT HANDLE ASSEMBLY WITH RECONFIGURABLE GRIP PORTION;

U.S. patent application Ser. No. 15/089,262, entitled ROTARY POWERED SURGICAL INSTRUMENT WITH MANUALLY ACTUATABLE BAILOUT SYSTEM;

U.S. patent application Ser. No. 15/089,277, entitled SURGICAL CUTTING AND STAPLING END EFFECTOR WITH ANVIL CONCENTRIC DRIVE MEMBER;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS;

U.S. patent application Ser. No. 15/089,258, entitled SURGICAL STAPLING SYSTEM COMPRISING A SHIFTABLE TRANSMISSION;

U.S. patent application Ser. No. 15/089,278, entitled SURGICAL STAPLING SYSTEM CONFIGURED TO PROVIDE SELECTIVE CUTTING OF TISSUE;

U.S. patent application Ser. No. 15/089,284, entitled SURGICAL STAPLING SYSTEM COMPRISING A CONTOURABLE SHAFT;

U.S. patent application Ser. No. 15/089,295, entitled SURGICAL STAPLING SYSTEM COMPRISING A TISSUE COMPRESSION LOCKOUT;

U.S. patent application Ser. No. 15/089,300, entitled SURGICAL STAPLING SYSTEM COMPRISING AN UNCLAMPING LOCKOUT;

U.S. patent application Ser. No. 15/089,196, entitled SURGICAL STAPLING SYSTEM COMPRISING A JAW CLOSURE LOCKOUT;

U.S. patent application Ser. No. 15/089,203, entitled SURGICAL STAPLING SYSTEM COMPRISING A JAW ATTACHMENT LOCKOUT;

U.S. patent application Ser. No. 15/089,210, entitled SURGICAL STAPLING SYSTEM COMPRISING A SPENT CARTRIDGE LOCKOUT;

U.S. patent application Ser. No. 15/089,324, entitled SURGICAL INSTRUMENT COMPRISING A SHIFTING MECHANISM;

U.S. patent application Ser. No. 15/089,335, entitled SURGICAL STAPLING INSTRUMENT COMPRISING MULTIPLE LOCKOUTS;

U.S. patent application Ser. No. 15/089,339, entitled SURGICAL STAPLING INSTRUMENT;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS;

U.S. patent application Ser. No. 15/089,304, entitled SURGICAL STAPLING SYSTEM COMPRISING A GROOVED FORMING POCKET;

U.S. patent application Ser. No. 15/089,331, entitled ANVIL MODIFICATION MEMBERS FOR SURGICAL STAPLE/FASTENERS;

U.S. patent application Ser. No. 15/089,336, entitled STAPLE CARTRIDGES WITH ATRAUMATIC FEATURES;

U.S. patent application Ser. No. 15/089,312, entitled CIRCULAR STAPLING SYSTEM COMPRISING AN INCISABLE TISSUE SUPPORT;

U.S. patent application Ser. No. 15/089,309, entitled CIRCULAR STAPLING SYSTEM COMPRISING ROTARY FIRING SYSTEM; and U.S. patent application Ser. No. 15/089,349, entitled CIRCULAR STAPLING SYSTEM COMPRISING LOAD CONTROL.

Applicant of the present application also owns the U.S. Patent Applications identified below which were filed on Dec. 31, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS;

U.S. patent application Ser. No. 14/984,525, entitled MECHANISMS FOR COMPENSATING FOR DRIVETRAIN FAILURE IN POWERED SURGICAL INSTRUMENTS; and U.S. patent application Ser. No. 14/984,552, entitled SURGICAL INSTRUMENTS WITH SEPARABLE MOTORS AND MOTOR CONTROL CIRCUITS.

Applicant of the present application also owns the U.S. Patent Applications identified below which were filed on Feb. 9, 2016 which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR;

U.S. patent application Ser. No. 15/019,228, entitled SURGICAL INSTRUMENTS WITH MULTIPLE LINK ARTICULATION ARRANGEMENTS;

U.S. patent application Ser. No. 15/019,196, entitled SURGICAL INSTRUMENT ARTICULATION MECHANISM WITH SLOTTED SECONDARY CONSTRAINT;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY;

U.S. patent application Ser. No. 15/019,215, entitled SURGICAL INSTRUMENTS WITH NON-SYMMETRICAL ARTICULATION ARRANGEMENTS;

U.S. patent application Ser. No. 15/019,227, entitled ARTICULATABLE SURGICAL INSTRUMENTS WITH SINGLE ARTICULATION LINK ARRANGEMENTS;

U.S. patent application Ser. No. 15/019,235, entitled SURGICAL INSTRUMENTS WITH TENSIONING ARRANGEMENTS FOR CABLE DRIVEN ARTICULATION SYSTEMS;

U.S. patent application Ser. No. 15/019,230, entitled ARTICULATABLE SURGICAL INSTRUMENTS WITH OFF-AXIS FIRING BEAM ARRANGEMENTS; and U.S. patent application Ser. No. 15/019,245, entitled SURGICAL INSTRUMENTS WITH CLOSURE STROKE REDUCTION ARRANGEMENTS.

Applicant of the present application also owns the U.S. Patent Applications identified below which were filed on Feb. 12, 2016 which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS;

U.S. patent application Ser. No. 15/043,259, entitled MECHANISMS FOR COMPENSATING FOR DRIVETRAIN FAILURE IN POWERED SURGICAL INSTRUMENTS;

U.S. patent application Ser. No. 15/043,275, entitled MECHANISMS FOR COMPENSATING FOR DRIVETRAIN FAILURE IN POWERED SURGICAL INSTRUMENTS; and U.S. patent application Ser. No. 15/043,289, entitled MECHANISMS FOR COMPENSATING FOR DRIVETRAIN FAILURE IN POWERED SURGICAL INSTRUMENTS.

Applicant of the present application owns the following patent applications that were filed on Jun. 18, 2015 and which are each herein incorporated by reference in their respective entirety:

U.S. patent application Ser. No. 14/742,925, entitled SURGICAL END EFFECTORS WITH POSITIVE JAW OPENING ARRANGEMENTS, now U.S. Pat. No. 10,182,818;

U.S. patent application Ser. No. 14/742,941, entitled SURGICAL END EFFECTORS WITH DUAL CAM ACTUATED JAW CLOSING FEATURES, now U.S. Pat. No. 10,052,102;

U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;

U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;

U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following patent applications that were filed on Mar. 6, 2015 and which are each herein incorporated by reference in their respective entirety:

U.S. patent application Ser. No. 14/640,746, entitled POWERED SURGICAL INSTRUMENT, now U.S. Pat. No. 9,808,246;

U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;

U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Patent Application Publication No. 2016/0256154;

U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Patent Application Publication No. 2016/0256071;

U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,985,148;

U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;

U.S. patent application Ser. No. 14/640,817, entitled INTERACTIVE FEEDBACK SYSTEM FOR POWERED SURGICAL INSTRUMENTS, now U.S. Pat. No. 9,924,961;

U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;

U.S. patent application Ser. No. 14/640,837, entitled SMART SENSORS WITH LOCAL SIGNAL PROCESSING, now U.S. Pat. No. 9,993,248;

U.S. patent application Ser. No. 14/640,765, entitled SYSTEM FOR DETECTING THE MIS-INSERTION OF A STAPLE CARTRIDGE INTO A SURGICAL STAPLE/FASTENER, now U.S. Patent Application Publication No. 2016/0256160;

U.S. patent application Ser. No. 14/640,799, entitled SIGNAL AND POWER COMMUNICATION SYSTEM POSITIONED ON A ROTATABLE SHAFT, now U.S. Pat. No. 9,901,342; and U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following patent applications that were filed on Feb. 27, 2015, and which are each herein incorporated by reference in their respective entirety:

U.S. patent application Ser. No. 14/633,576, entitled SURGICAL INSTRUMENT SYSTEM COMPRISING AN INSPECTION STATION, now U.S. Pat. No. 10,045,779;

U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;

U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;

U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;

U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;

U.S. patent application Ser. No. 14/633,542, entitled REINFORCED BATTERY FOR A SURGICAL INSTRUMENT, now U.S. Pat. No. 9,931,118;

U.S. patent application Ser. No. 14/633,548, entitled POWER ADAPTER FOR A SURGICAL INSTRUMENT, now U.S. Pat. No. 10,245,028;

U.S. patent application Ser. No. 14/633,526, entitled ADAPTABLE SURGICAL INSTRUMENT HANDLE, now U.S. Pat. No. 9,993,258;

U.S. patent application Ser. No. 14/633,541, entitled MODULAR STAPLING ASSEMBLY, now U.S. Pat. No. 10,226,250; and U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;

U.S. patent application Ser. No. 14/574,483, entitled SURGICAL INSTRUMENT ASSEMBLY COMPRISING LOCKABLE SYSTEMS, now U.S. Pat. No. 10,188,385;

U.S. patent application Ser. No. 14/575,139, entitled DRIVE ARRANGEMENTS FOR ARTICULATABLE SURGICAL INSTRUMENTS, now U.S. Pat. No. 9,844,375;

U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;

U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;

U.S. patent application Ser. No. 14/575,143, entitled SURGICAL INSTRUMENTS WITH IMPROVED CLOSURE ARRANGEMENTS, now U.S. Pat. No. 10,004,501;

U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;

U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;

U.S. patent application Ser. No. 14/574,493, entitled SURGICAL INSTRUMENT ASSEMBLY COMPRISING A FLEXIBLE ARTICULATION SYSTEM, now U.S. Pat. No. 9,897,000; and U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;

U.S. patent application Ser. No. 13/782,323, entitled ROTARY POWERED ARTICULATION JOINTS FOR SURGICAL INSTRUMENTS, now U.S. Pat. No. 9,782,169;

U.S. patent application Ser. No. 13/782,338, entitled THUMBWREEL SWITCH ARRANGEMENTS FOR SURGICAL INSTRUMENTS, now U.S. Patent Application Publication No. 2014/0249557;

U.S. patent application Ser. No. 13/782,499, entitled ELECTROMECHANICAL SURGICAL DEVICE WITH SIGNAL RELAY ARRANGEMENT, now U.S. Pat. No. 9,358,003;

U.S. patent application Ser. No. 13/782,460, entitled MULTIPLE PROCESSOR MOTOR CONTROL FOR MODULAR SURGICAL INSTRUMENTS, now U.S. Pat. No. 9,554,794;

U.S. patent application Ser. No. 13/782,358, entitled JOYSTICK SWITCH ASSEMBLIES FOR SURGICAL INSTRUMENTS, now U.S. Pat. No. 9,326,767;

U.S. patent application Ser. No. 13/782,481, entitled SENSOR STRAIGHTENED END EFFECTOR DURING REMOVAL THROUGH TROCAR, now U.S. Pat. No. 9,468,438;

U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;

U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

U.S. patent application Ser. No. 13/803,097, entitled ARTICULATABLE SURGICAL INSTRUMENT COMPRISING A FIRING DRIVE, now U.S. Pat. No. 9,687,230;

U.S. patent application Ser. No. 13/803,193, entitled CONTROL ARRANGEMENTS FOR A DRIVE MEMBER OF A SURGICAL INSTRUMENT, now U.S. Pat. No. 9,332,987;

U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;

U.S. patent application Ser. No. 13/803,086, entitled ARTICULATABLE SURGICAL INSTRUMENT COMPRISING AN ARTICULATION LOCK, now U.S. Patent Application Publication No. 2014/0263541;

U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;

U.S. patent application Ser. No. 13/803,148, entitled MULTI-FUNCTION MOTOR FOR A SURGICAL INSTRUMENT, now U.S. Pat. No. 10,470,762;

U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;

U.S. patent application Ser. No. 13/803,117, entitled ARTICULATION CONTROL SYSTEM FOR ARTICULATABLE SURGICAL INSTRUMENTS, now U.S. Pat. No. 9,351,726;

U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO DETECT MISLOADED CARTRIDGE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL INSTRUMENT SHAFT INCLUDING SWITCHES FOR CONTROLLING THE OPERATION OF THE SURGICAL INSTRUMENT, now U.S. Pat. No. 9,844,368;

U.S. patent application Ser. No. 14/248,588, entitled POWERED LINEAR SURGICAL STAPLE/FASTENER, now U.S. Pat. No. 10,405,857;

U.S. patent application Ser. No. 14/248,591, entitled TRANSMISSION ARRANGEMENT FOR A SURGICAL INSTRUMENT, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLE/FASTENER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

FIGS. 1 and 2 depict a surgical instrument assembly 1000 comprising a sensing system configured to sense a parameter such as displacement, for example, of an actuation member of the surgical instrument assembly 1000. The surgical instrument assembly 1000 comprises a shaft assembly 1010 and an end effector assembly 1030 attached to the shaft assembly 1010 by way of an articulation joint 1020. The shaft assembly 1010 comprises an attachment portion 1011 configured to be attached to an attachment interface. Such an attachment interface may comprise, for example, a surgical robot and/or a handheld surgical device. The shaft assembly 1010 further comprises a body portion 1013 configured to house internal components of the surgical instrument assembly 1000. The end effector assembly 1030 comprises a proximal frame portion 1031 attached to the shaft assembly 1011 by way of the articulation joint 1020. The end effector assembly 1030 further comprises a first jaw 1032 and a second jaw 1033. The end effector assembly 1030 comprises a surgical stapling end effector; however, other types of surgical end effectors are contemplated.

The surgical instrument assembly 1000 further comprises an actuation system 1050 configured to actuate a function of the end effector assembly 1030. The actuation system 1050 comprises a first actuation member 1051 configured to be operably coupled with an actuation driver of the attachment interface to actuate the function of the end effector assembly 1030. The actuation system 1050 further comprises a second actuation member 1055 coupled to the first actuation member 1051 such that the first actuation member 1051 can move the second actuation member 1055. The second actuation member 1055 comprises a proximal end 1056 comprising a tab 1057 extending into a slot 1053 of the first actuation member 1051. The second actuation member 1055 extends through the articulation joint 1020 and into the end effector assembly 1030. The second actuation member 1055 comprises a knife body 1059 configured to be actuated through the end effector assembly 1030 during a firing stroke. The second actuation member 1055 comprises a flexible configuration such that the second actuation member 1055 can be actuated when the surgical instrument assembly 1000 is in an articulated configuration. While a surgical stapling actuation member is depicted, other longitudinally translatable surgical actuation members are contemplated.

The surgical instrument assembly 1000 further comprises a sensing system 1060 configured to sense a parameter of the actuation system 1050. The sensing system 1060 comprises a stretchable optical waveguide 1061 comprising a proximal end 1063 fixed to the shaft 1013 relative to the actuation system 1050 and a distal end 1065 fixed to a tab 1058 of the second actuation member 1055. The stretchable optical waveguide 1061 extends across the articulation joint 1020. The stretchable optical waveguide 1061 is configured to stretch as the second actuation member 1055 is moved distally through the firing stroke. The tab 1058 is configured to pull the stretchable optical waveguide 1061 and stretch the stretchable optical waveguide as the second actuation member 1055 is advanced distally through the firing stroke. In at least one instance, the stretchable optical waveguide 1061 is held in tension in its home position.

The sensing system 1060 further comprises an attachment point 1064. The stretchable optical waveguide 1061 comprises a PDMS optical waveguide attached at the attachment point 1064. The stretchable optical waveguide 1061 comprises a light sensor that utilizes light emission within the optical wave guide and light measuring devices to measure the transmission of light through the waveguide as the waveguide stretches. In at least one instance, light is provided by vertical-cavity surface-emitting lasers. Such light measuring devices may comprise, for example, photodiodes. As the stretchable optical waveguide 1061 is stretched, the loss of light transmission within the stretchable optical waveguide 1061 increases. This difference in light transmission within the stretchable optical waveguide 1061 can be detected by the photodiodes. Similarly, as the stretchable optical waveguide 1061 returns to its un-stretched or, home, position, the amount of light transmitted within the stretchable optical waveguide 1061 increases.

The surgical instrument assembly 1000 further comprises a control circuit configured to monitor the light transmission through the stretchable optical waveguide 1061 by monitoring the signals transmitted by the photodiodes. In at least one instance, the stretchable optical waveguide 1061 comprises a single output corresponding to the stretch length of the stretchable optical waveguide 1061. The control circuit is configured to determine a parameter, such as displacement, for example, of the knife body 1059 based on the monitored light transmission within the stretchable optical waveguide 1061. In such instances, the signals received from the photodiodes correspond to the position of the knife body 1059. The position of the knife body 1059 can be determined by comparing the monitored signals to a pre-determined data set and/or by a pre-determined algorithm. In addition to the above, monitoring the signals of the photodiodes over time can allow the tracking of parameters involving time. Such parameters include acceleration and velocity, for example.

In at least one instance, the control circuit is configured to measure the light transmission, or optical loss, within the stretchable optical waveguide 1061 when the actuation system 1050 is in an unfired configuration. The control circuit can subsequently compare the measured light transmission within the stretchable optical waveguide 1061 to the light transmission measured in the unfired configuration to determine the position of the knife body 1059 relative to the unfired position of the knife body 1059. The position of the knife body 1059 can then be determined based on the change in light transmission within the stretchable optical waveguide 1061 as a function of the stretch length of the stretchable optical waveguide 1061.

In at least one instance, the control circuit is configured to compare the determined displacement of the knife body 1059 to an expected displacement of the knife body 1059 deduced by a motor encoder on the motor driving the actuation system 1050. In at least one instance, the control circuit is configured to adjust the control program of the actuation system 1050 if there are discrepancies between the motor-encoder data and the sensed displacement by way of the sensing system 1060. A discrepancy between the two systems could indicate that there is system backlash, for example, between the motor and the knife body 1059. Such detected variance can be corrected for by the control circuit to ensure a full firing stroke, for example.

In at least one instance, surgical instruments comprising can comprise multiple stretchable optical waveguides. For example, the articulation system may comprise a stretchable optical waveguide and/or a separate closure system may comprise a stretchable optical waveguide. The waveguides may be attached at any suitable location on the drive members and at any suitable location on the shaft. In at least one instance, a stretchable optical waveguide is attached to two non-fixed attachment locations. For example, a waveguide may be attached to a knife body and an articulation drive rod. In such an instance, the difference in actuation length of each member may vary substantially enough to be able to use a stretchable optical waveguide in such a manner.

A control system receiving data regarding the actual position of a staple firing drive, a closure drive, and/or an articulation drive can modify the actuation strokes of these drives after evaluating the data. For instance, if the control system detects that the staple firing drive is further distal than anticipated, the control system can shorten the actuation stroke of the staple firing drive.

FIG. 3 depicts a surgical instrument assembly 1100 comprising a sensing system configured to sense a parameter of an actuation member of the surgical instrument assembly 1100. The surgical instrument assembly 1100 is similar in many respects to the surgical instrument assembly 1000 discussed above. The surgical instrument assembly 1100 comprises a sensing system 1160 configured to sense a parameter of the actuation system 1050. The sensing system 1160 comprises a stretchable optical waveguide 1161 comprising a proximal end 1163 fixed to the shaft 1013 relative to the actuation system 1050 and a distal end 1165 fixed directly to the knife body 1059. The stretchable optical waveguide 1161 extends across the articulation joint 1020. The stretchable optical waveguide 1161 is configured to stretch as the second actuation member 1055 is moved through the firing stroke. The knife body 1059 is configured to pull the stretchable optical waveguide 1161 and stretch the stretchable optical waveguide 1161 as the second actuation member 1055 is advanced distally through the firing stroke. In at least one instance, the stretchable optical waveguide 1161 is held in tension in its home position.

Referring to FIG. 3, further to the above, distances 1171, 1173, 1175 are labeled and correspond to various positions of the knife body 1059 along its staple firing stroke. Distance 1171 corresponds to a home position of the knife body 1059, distance 1173 corresponds to an intermediate position of the knife body 1059, and distance 1175 corresponds to an end-of-stroke position of the knife body 1059. These distances 1171, 1173, 1175 correspond to magnitudes of light transmission sensed within the stretchable optical waveguide 1161. If the light sensed within the optical waveguide 1161 matches the expected light within the optical waveguide 1161 for a given position of the knife body 1059, the control system does not modify the stroke length of the knife body 1059. If, however, the light sensed within the optical waveguide 1161 does not match the expected light within the optical waveguide 1161, the control system can shorten or lengthen the stroke length of the knife body 1069 such that the knife body 1059 stops at the correct location at the end of the firing stroke. In addition to or in lieu of the above, the control system can modify another parameter of the firing stroke based on the light sensed within the optical waveguide 1161. For instance, the control system can alter the speed and/or acceleration of the knife body 1059 when the sensed light intensity within the optical waveguide 1161 does not match the expected light intensity. For example, the control system can lower the maximum speed of the knife body 1059 and/or lower the maximum acceleration of the knife body 1059 when the sensed and expected light intensities don't match. In many instances, a slower knife body 1059 is less likely to cause unexpected damage to the stapling system that might be caused by a shifted knife body 1059. Also, for example, the control system can lower the maximum current that can be drawn by the electric motor when the sensed and expected light intensities don't match. In such instances, the force transmitted through the knife body 1059 is lowered to reduce to possibility of unexpected damage to the stapling system. In certain instances, the control system can modify the time, or pause, between operational steps when a discrepancy is detected. In at least one instance, the control system can increase the pause between clamping the end effector and performing a staple firing stroke, for example.

FIGS. 4-6 depict a surgical instrument assembly 1200 comprising a sensing system configured to sense a parameter of an actuation member of the surgical instrument assembly 1200. The surgical instrument assembly 1200 is similar in many respects to the surgical instrument assemblies 1000, 1100 discussed above. The surgical instrument assembly 1200 comprises a sensing system 1260 configured to sense a parameter of the actuation system 1050. The sensing system 1260 comprises a stretchable optical waveguide 1261 comprising a proximal end 1263 fixed to the proximal frame portion 1031 (distal to the articulation joint 1020) of the end effector assembly 1030 relative to the actuation system 1050 and a distal end 1265 fixed directly to the knife body 1059. The sensing system 1260 further comprises an electrical connection 1280 attached to the sensing system 1260 configured to transmit signals to a control circuit. The stretchable optical waveguide 1261 does not extend across the articulation joint 1020. The stretchable optical waveguide 1261 is configured to stretch as the knife body 1059 is moved through the firing stroke. The knife body 1059 is configured to pull the stretchable optical waveguide 1261 and stretch the stretchable optical waveguide 1261 as the second actuation member 1055 is advanced distally through the firing stroke.

FIG. 4 illustrates the stretchable optical waveguide 1261 in its home configuration indicating that the knife body 1059 is at its home position 1271. In at least one instance, the stretchable optical waveguide 1261 is held in tension in its home configuration. FIG. 5 illustrates the stretchable optical waveguide 1261 in a stretched configuration indicating that the knife body 1059 is at an end-of-stroke position 1275. FIG. 6 illustrates the surgical instrument assembly 1200 in an articulated configuration where the electrical connection is bent around the articulation joint to accommodate the articulated configuration. As can be seen in FIG. 6, the stretchable optical waveguide 1261 is not affected by the articulation of the end effector assembly 1030.

In at least one instance, a control circuit is configured to determine when the knife body 1059 reaches position 1273 (FIG. 4). Once the knife body 1059 reaches the position 1273, the control circuit can dynamically break the motor driving the knife body 1059 to prevent the knife body 1059 from crashing into the end of the end effector assembly 1030. Such crashing may cause damage to the knife body 1059 and/or components within the surgical instrument assembly 1200 to seize and/or jam. In at least one instance, the control system can dynamically brake the knife body 1059 using a pulse width modulation (PWM) circuit which shortens the voltage pulses being applied to the electric motor. In other instances, a frequency modulation (FM) circuit can be used, for example. In certain instances, the magnitude of the voltage being applied to the electric motor is lowered. In some instances, the control system can apply reverse polarity pulses to the electric motor to slow the firing stroke. In any event, the information provided by the waveguide 1261 to the control system allows the control system to determine when to begin the braking process. In at least one instance, the staple firing stroke is 60 mm long, for example, and the control system is configured to begin its braking routine at the 50 mm location in the staple firing stroke. If the control system detects that the light intensity detected by the waveguide 1261 does not match the predicted light intensity for a given distance in the staple firing stroke, the control system may begin its braking process earlier than 50 mm, for example.

Further to the above, the control system can be configured to assess whether the measured light within a waveguide is within a certain acceptable range. In such instances, the control system will determine that a match has been made and will not alter the firing stoke characteristics, at least based on this type of measurement. If, however, the measured light falls outside of the acceptable range, the control system can modify the firing strike as described herein.

The stretchable optical waveguide 1261 is configured to stretch within a channel in the first jaw 1032 as the knife body 1059 is advanced. Embodiments are contemplated where the stretchable optical waveguide 1261 is positioned to stretch within the second jaw 1033. In at least one instance, the stretchable optical waveguide 1261 can be used to determine the position of the first jaw 1032 relative to the second jaw 1033. For example, in surgical stapling end effector assemblies, the knife body 1059 is used to clamp the first jaw 1032 relative to the second jaw 1033. In such assemblies, longitudinal travel of the knife body 1059 can also determine the state of clamping of the end effector assembly 1030. Another example can involve a separate clamping actuator; however, when the end effector assembly is clamped, the knife body 1059 is pulled and/or pushed forward slightly into a ready-to-fire position. This movement, caused by the clamping actuator, can be detected by the stretchable optical waveguide 1261.

Figure 7A:
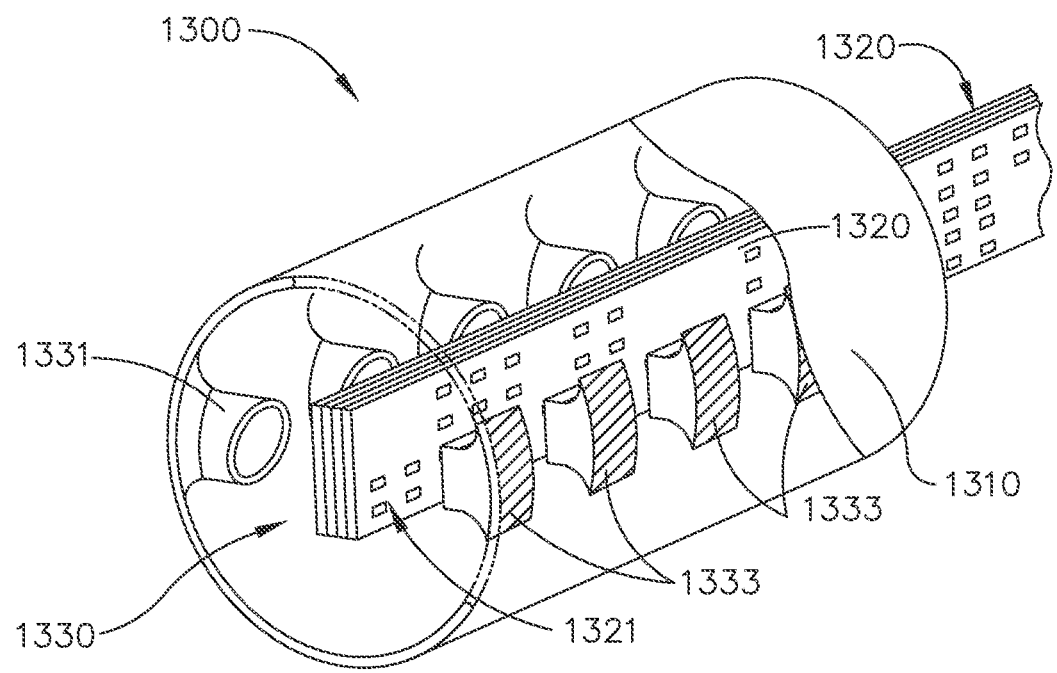
FIG. 7A is a partial perspective view of a surgical instrument assembly comprising a shaft, an actuation member, and a sensing system configured to sense a parameter of the actuation member.
Figure 7B:
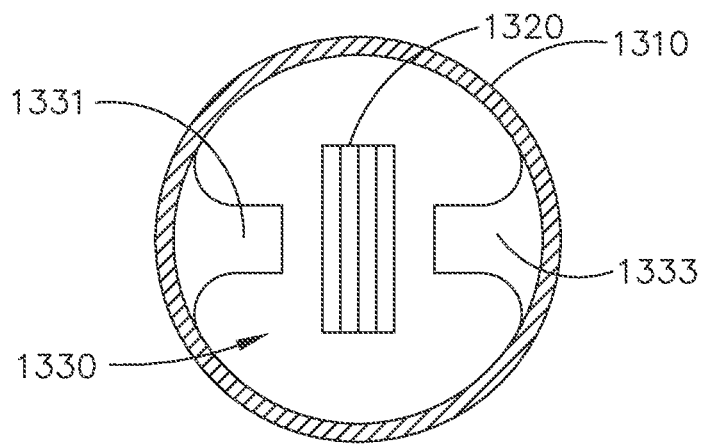
FIG. 7B is an end view of the surgical instrument assembly of FIG. 7A.

FIGS. 7A and 7B depict a surgical instrument assembly 1300 configured to detect a parameter of an actuation member of the surgical instrument assembly 1300. The surgical instrument assembly 1300 comprises a hollow shaft 1310, an actuation member 1320 such as a firing member, for example, and a sensing system 1330 configured to sense a parameter such as movement, for example, of the actuation member 1320. The sensing system 1330 comprises a plurality of light emitters 1331 oriented perpendicular to or at least substantially perpendicular to the actuation member 1320 and mounted to the hollow shaft 1310, a plurality of windows 1321 defined in the actuation member 1320 configured to allow light to pass through the actuation member 1320 and a plurality of light sensors, or receivers, 1333 configured to detect light emitted by the light emitters 1331 and mounted to the hollow shaft 1310.

As the actuation member 1320 translates within the hollow shaft 1310, the light sensors 1333 detect the change in light presence caused by the windows 1321. This change in light presence corresponds to movement of the actuation member 1320. Providing multiple light sensors 1333 longitudinally along the shaft 1310 allows the detection of changes in light presence along a length within the shaft 1310. A control circuit can monitor the signals of each light sensor and determine the exact position of the actuation member 1320. The control circuit can further monitor these signals over time to determine other parameters such as, for example, velocity and acceleration of the actuation member 1320.

In at least one instance, the light sensors 1333 comprise photodiodes. In at least one instance, the light emitters 1331 comprise LEDs. Any suitable light sensor and/or light emitter can be used. Moreover, any suitable combination of light sensor and light emitter can be used. In at least one instance, the detection of light presence, alone, is used to determine the position of the actuation member 1320. In at least one instance, the detection of light intensity is used to determine the position of the actuation member 1320. Light intensity can be varied by arranging the plurality of windows 1321 in specific patterns where some patterns allow a first amount of light to pass through and other patterns allow a second amount of light to pass through which is different than the first amount of light. Such a sensing system utilizing lights may provide a greater degree of reliability in aqueous environments. For example, light presence detection may be more reliable where bodily fluid and/or debris may be present within the range of the sensing system 1330.

Still referring to FIGS. 7A and 7B, a control circuit can compare the position of the actuation member 1320 detected by the sensing system 1330 with an expected position of the actuation member 1320 detected by a motor encoder driving the actuation member 1320. Adjustments can be made to the motor control program and/or alerts can be sent to a user indicating that a variance exists between the outputs of each detection system.

In various instances, one or more parameters of drive members in a surgical instrument assembly can be sensed using a stretchable resistive material in a similar fashion to the stretchable optical waveguide discussed above.

Figure 8:
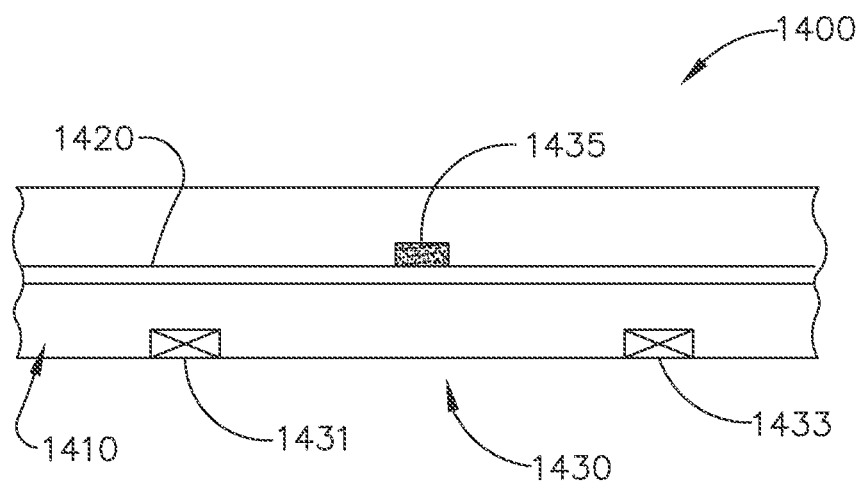
FIG. 8 is a partial elevational view of a surgical instrument assembly comprising a shaft, an actuation member, and a sensing system comprising Hall effect sensors configured to detect the position of the actuation member.

FIG. 8 depicts a surgical instrument assembly 1400 comprising a shaft 1410, an actuation member 1420, and a sensing system 1430 configured to sense a parameter such as, for example, the displacement of the actuation member 1420. The sensing system 1430 comprises a first Hall Effect sensor 1431 positioned with the shaft 1410, a second Hall Effect sensor 1433 positioned with the shaft 1410, and a magnet 1435 attached to the actuation member 1420. The first Hall Effect sensor 1431 is proximal to the second Hall Effect sensor 1433. The magnet 1435 is configured to alter the magnetic field surrounding the first Hall Effect sensor 1431 and the second Hall Effect sensor 1433 allowing a control circuit to determine the position of the actuation member 1420.

Figure 11:
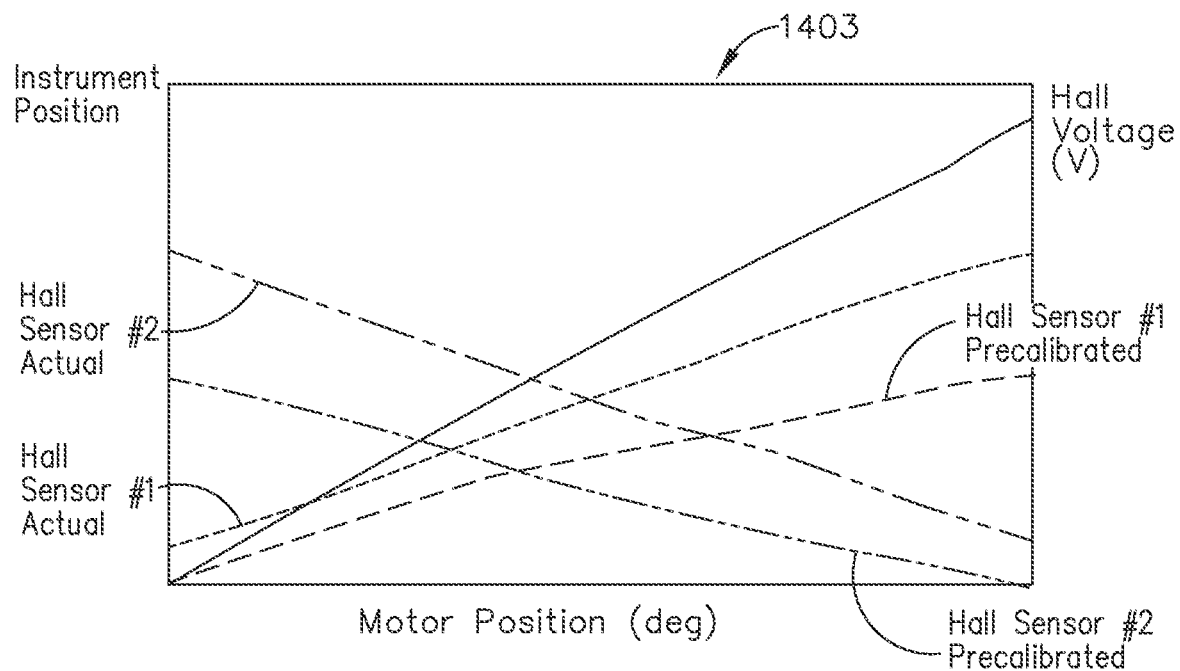
FIG. 11 is a graph including the graphs of FIGS. 9 and 10 and an example of an actual readout of the Hall effect sensors of FIG. 8 during an actuation stroke.
Figure 9:
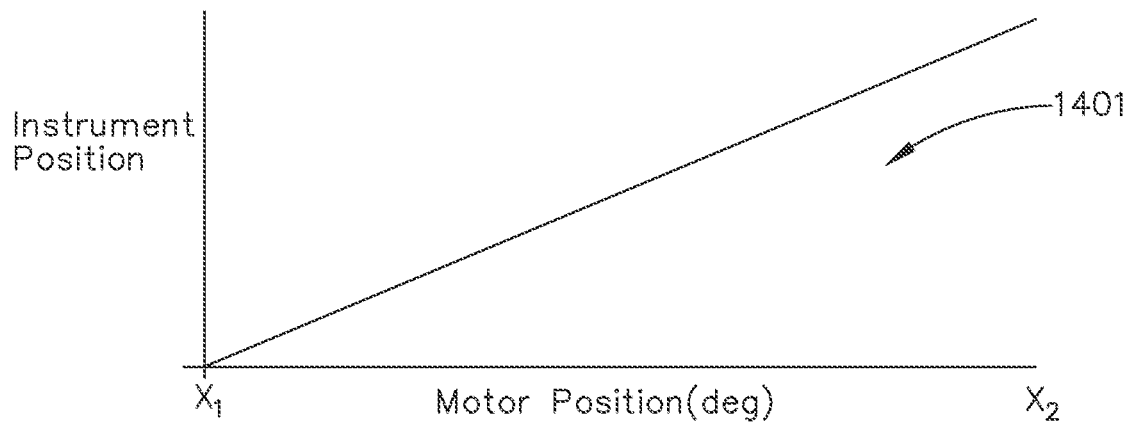
FIG. 9 is graph of the position of the actuation member of FIG. 8 relative to a motor position.
Figure 10:
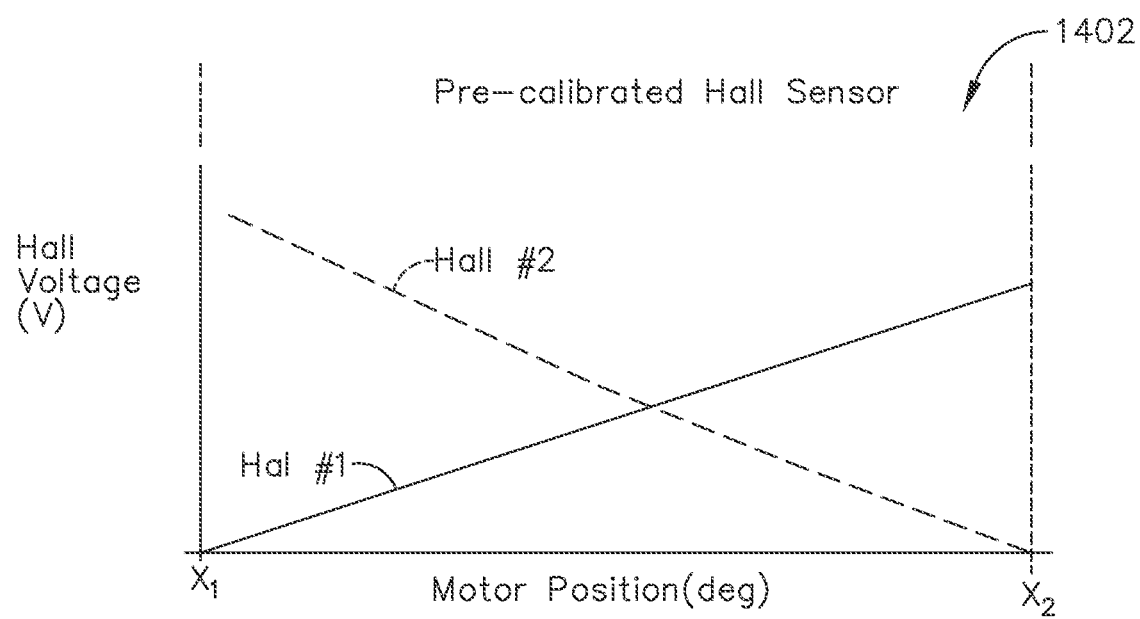
FIG. 10 is a graph of an expected voltage of the Hall effect sensors of FIG. 8 relative to the motor position.

FIG. 9 is graph 1401 of the position of the actuation member 1420 relative to the motor position. The motor position can be detected using an encoder, for example. FIG. 10 is a graph 1402 of the expected voltage of the Hall Effect sensors 1431, 1433 relative to the motor position. FIG. 11 is a graph 1403 including graphs 1401, 1402 as well as the actual readout of the Hall Effect sensors 1431, 1433 during an actuation stroke. The actual readout of the Hall Effect sensors 1431, 1433 differs from the expected readout of the Hall Effect sensors 1431, 1433. This may be attributed to component wear, for example. Because the actual readout of the Hall Effect sensors 1431, 1433 differs from the expected readout of the Hall Effect sensors 1431, 1433, a control circuit can detect this difference and adjust a motor control program actuating the actuation member 1420 to correct the position of the actuation member 1420 relative to the sensing system 1430 and/or otherwise alter the operation of the motor control program. In various instances, the motor control program can slow the actuation member 1420, shorten the stroke of the actuation member 1420, and/or reduce the maximum current that can be drawn by the electric motor, for example. In certain instances, the control system can modify the time, or pause, between operational steps when a discrepancy is detected. In at least one instance, the control system can increase the pause between clamping the end effector and performing a staple firing stroke, for example. In addition to or in lieu of the above, the control circuit can ignore the sensing system 1430 and rely only on the motor encoder when the expected readout differs from the actual readout.

In various embodiments, further to the above, the distance between the Hall Effect sensors 1431 and 1433 is fixed and known to the control system of the surgical instrument. In many instances, the magnet 1435 will simultaneously disturb the fields produced by the Hall Effect sensors 1431 and 1433. If the magnet 1435 is closer to the Hall Effect sensor 1431 than the Hall Effect sensor 1433, for instance, the disturbance detected by the Hall Effect sensor 1431 may be greater than the disturbance detected by the Hall Effect sensor 1433. In at least one instance, the relative disturbances detected by the Hall Effect sensors 1431 and 1433 can be used by the control system to determine and verify the position of the actuation member 1420. If one or both of these sensors is producing an output that does not match the expected output for a given output of the electric motor, the control system can enter into a remedial state in which the data input streams are prioritized.

Figure 12:
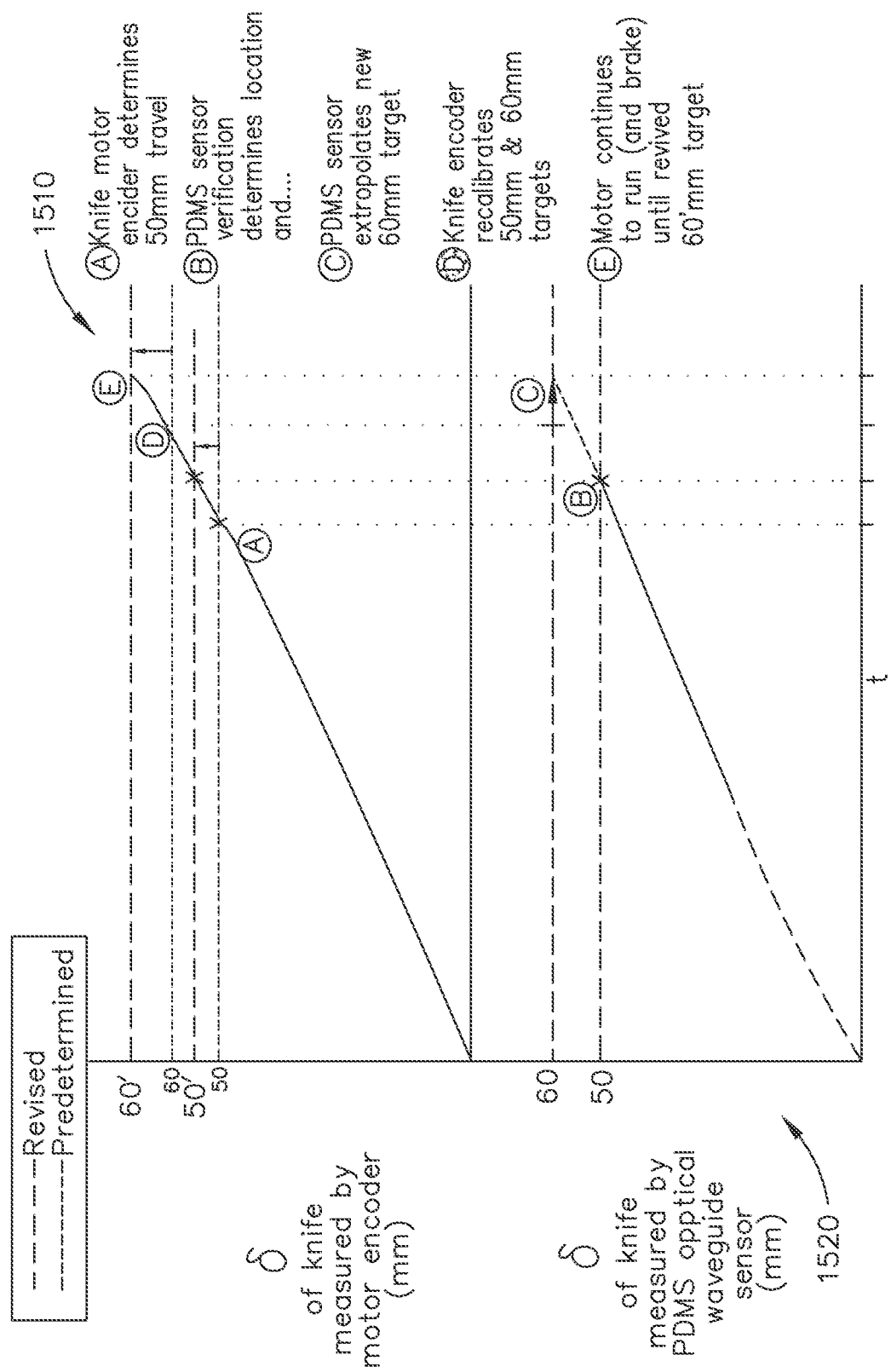
FIG. 12 is a graph of an actuation stroke of an actuation member measured by a motor encoder and a graph of the actuation stroke of the actuation member measured by a stretchable optical waveguide.

In at least one instance, a control circuit is configured to monitor the movement of a motor and the movement of an actuator configured to be actuated by the motor. The control circuit is configured to compare the monitored movements and take action accordingly. FIG. 12 is a graph illustrating a relationship between a motor and an actuator configured to be actuated by the motor. The control circuit is configured to move the actuator through a 60 mm stroke, for example, although any suitable stroke lengths could be used. For instance, a 30 mm stroke or a 45 mm stroke could be used. Movement of the motor 1510 is directly monitored by a motor encoder. Movement of the actuator 1520 is directly monitored by any suitable sensing systems such as those discussed herein, for example. In this instance, the actuator movement is sensed by a stretchable optical waveguide. The graph 1510 illustrates sensed motor movement by a motor encoder relative to time. This measurement is local to the motor. The graph 1520 illustrates sensed movement of the actuator by the stretchable optical waveguide relative to time. This measurement is local to the actuator. In at least one instance, the actuator is downstream one or more modular attachment location in a modular surgical instrument system. For instance, a first measurement can be taken in a first component of the modular instrument system while a second measurement can be taken in a second component attached to the first component wherein the attachment between the first and second components is either direct or indirect.

The control circuit is configured to run the motor to actuate the actuator. At position A, the control circuit determines that the motor has been actuated a specific amount corresponding to an expected 50 mm of movement of the actuator. As can be seen at position A, the actuator has not traveled the expected 50 mm because the stretchable optical waveguide has not sensed 50 mm of movement, yet. At position B, the actuator has been sensed by the stretchable optical waveguide to have moved 50 mm and the motor has been actuated more than the specific amount corresponding to the expected 50 mm of movement of the actuator. This new amount, seen at position D, can be logged by the control circuit to calibrate the motor control program such that this new amount of motor movement corresponds to the expected 50 mm of movement of the actuator from this point forward. This data may also simply be logged and taken into consideration in subsequent actuations.

Once the actual movement of the actuator is sensed at the 50 mm location (B), the control circuit is configured to extrapolate a new 60 mm target (E). At such point, the control circuit is configured to re-calibrate the 50 mm and 60 mm targets for the motor movement. Once the new targets D and E are logged, the control circuit can run the motor until the both sensed movements of the motor and the actuator reach the target (C, E). This calibration can be done for each modular attachment and for each actuation of a surgical instrument attachment. The control circuit is configured to compensate for varied actuation that may be caused by dive train slop, backlash, and/or wear, for example.

In at least one instance, predefined parameters for a motor such as the inertia of a rotor, for example, could be measured and/or calibrated as part of the initial assembly of a modular attachment to a motor. Such a parameter can be measured during a dynamic breaking event which slows the motor down to prevent inadvertent overstressing of components as an actuation member approaches an end-of-stroke position (such as the beginning or end of the stroke). Such a parameter can also be measured during the acceleration of the motor (such as starting a stroke and/or re-starting a stroke, for example). During such an event, a control circuit can utilize a motor encoder to monitor the inertia of the rotor and a local sensing system within the shaft to determine a corresponding inertia of the rotor. If a difference is detected between the determined inertia values based on the motor encoder and the local sensing system within the shaft given the predefined parameters, the system could adjust the dynamic braking and/or acceleration of the motor (rate, initiation trigger, magnitude) to have more efficient motor control with the attached surgical instrument.

Figure 14:
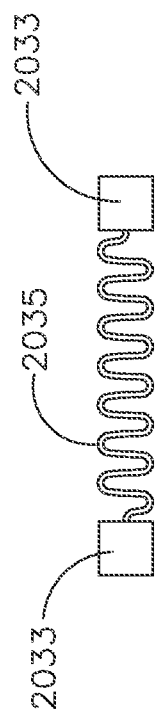
FIG. 14 is an elevational view of a stretchable zone of the flex circuit of FIG. 13 in a non-stretched configuration.
Figure 15:
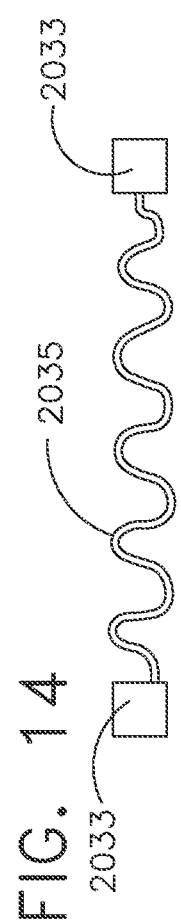
FIG. 15 is an elevational view of a stretchable zone of the flex circuit of FIG. 13 in a stretched configuration.
Figure 13:
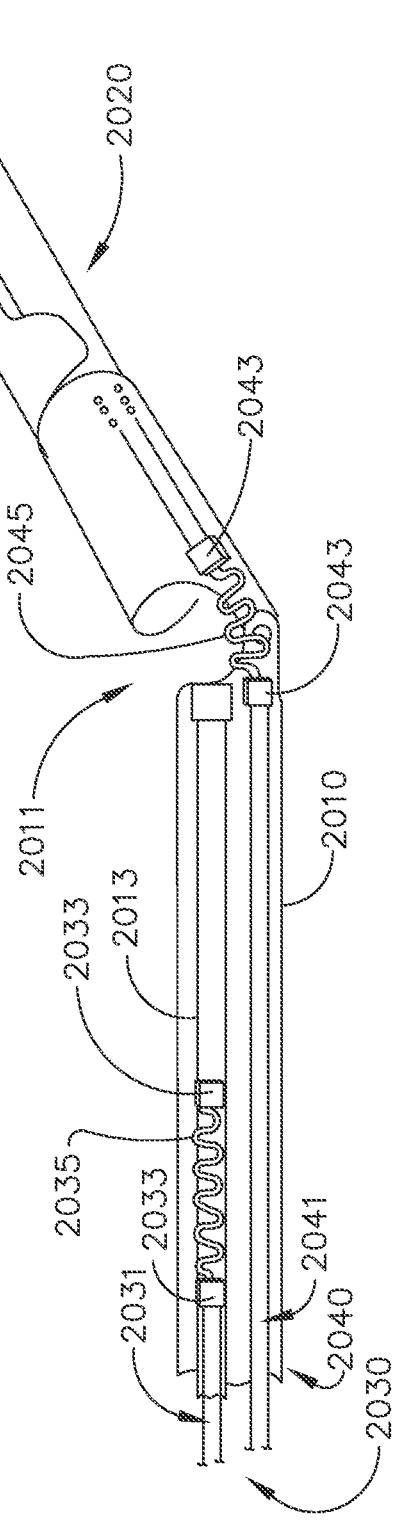
FIG. 13 is a partial perspective view of a surgical instrument assembly comprising a shaft, an end effector attached to the shaft by way of an articulation joint, and a flex circuit comprising a stretchable zone and a non-stretchable zone.

In various instances, surgical instrument attachments configured to be attached to surgical instrument control interfaces such as a surgical robot, for example, comprise onboard electronics. The onboard electronics can comprise any suitable circuitry elements such as sensors, printed circuit boards, processors, and/or batteries, for example. Referring now to FIGS. 13-15, a surgical instrument assembly 2000 is depicted. The surgical instrument assembly 2000 comprises a shaft 2010, an articulation joint 2011, and an end effector 2020 attached to the shaft 2010 by way of the articulation joint 2011. The end effector 2020 is configured to be articulated relative to the shaft 2010 about the articulation joint 2011. The surgical instrument assembly 2000 further comprises an articulation actuator 2013 configured to articulate the end effector 2020.

Still referring to FIGS. 13-15, the surgical instrument assembly 2000 further comprises a first flex circuit 2030 attached to the articulation actuator 2013 and a second flex circuit 2040 attached to another actuator of the surgical instrument assembly 2000 such as a firing member, for example. The first flex circuit 2030 extends through the shaft 2010 from a proximal end where the first flex circuit 2030 may be electrically coupled with contacts of the surgical control interface. The second flex circuit 2040 extends through the shaft 2010 from the proximal end where the second flex circuit 2040 may also be electrically coupled with the contacts of the surgical control interface.

The first flex circuit 2030 comprises a non-stretchable zone 2031 and a stretchable zone 2035. The stretchable zone 2035 comprises stretchable printed copper attached to printed circuit board 2033 at both ends of the stretchable zone 2035. The printed circuit board 2033 may be attached to the first flex circuit 2030 in a proximal location and attached to the articulation actuator 2013 in a distal location. The non-stretchable zone 2031 is configured to act as a normal flex circuit and the stretchable zone 2035 is configured to elastically stretch within the shaft 2010. The first flex circuit 2030 may be connected to various sensors, for example, positioned on the articulation actuator 2013 which are configured to measure a parameter of the articulation actuator 2013. The stretchable zone 2035 is configured elongate as the articulation actuator 2013 is moved through an articulation stroke while maintaining an electrical connection between the sensors of the articulation actuator and an upstream electrical circuit.

The second flex circuit 2040 comprises a non-stretchable zone 2041 and a stretchable zone 2045. The stretchable zone 2045 comprises stretchable printed copper attached to printed circuit board 2043 at both ends of the stretchable zone 2045. The printed circuit board 2043 is attached to the second flex circuit 2040 in a proximal location and is attached to the firing member in a distal location across the articulation joint 2011. The non-stretchable zone 2041 is configured to act as a normal flex circuit and the stretchable zone 2045 is configured to elastically stretch within the shaft 2010 across the articulation joint 2011. The stretchable zone 2045, in this instance, may be referred to as an articulation section of the second flex circuit 2040. The second flex circuit 2040 may be connected to various sensors, for example, positioned on the firing member and/or within the end effector 2020 which are configured to measure one or more parameters of the end effector. The stretchable zone 2045 is configured to stretch as the end effector 2020 is articulated about the articulation joint 2011 while maintaining an electrical connection between the sensors of the end effector 2020 and/or firing member and an upstream electrical circuit. The stretchable zone 2045 is also be configured to stretch, or elongate, as the firing member is advanced within the end effector 2020 should the second flex circuit 2040 be attached directly to the firing member.

In at least one instance, the first flex circuit 2030 and the second flex circuit 2040 are configured to elastically rebound and resiliently assume neutral, un-stretched configurations. Once in the neutral configurations, the first flex circuit 2030 and the second flex circuit 2040 may be stretched again upon the actuation of various actuators within the surgical instrument assembly 2000.

In at least one instance, the stretchable zones comprise flexible conductive inks and the non-stretchable zones comprise conductive metallic traces.

Figure 16:
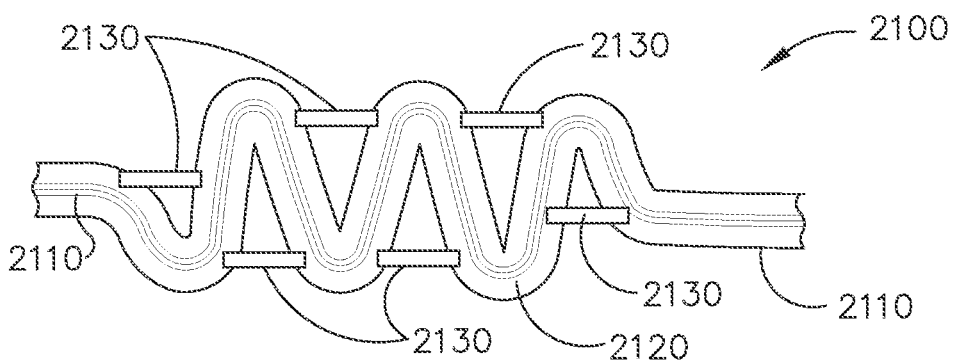
FIG. 16 is an elevational view of a flex circuit comprising a stretchable zone comprising elastic strut members, wherein the stretchable zone is illustrated in a non-stretched configuration.
Figure 17:
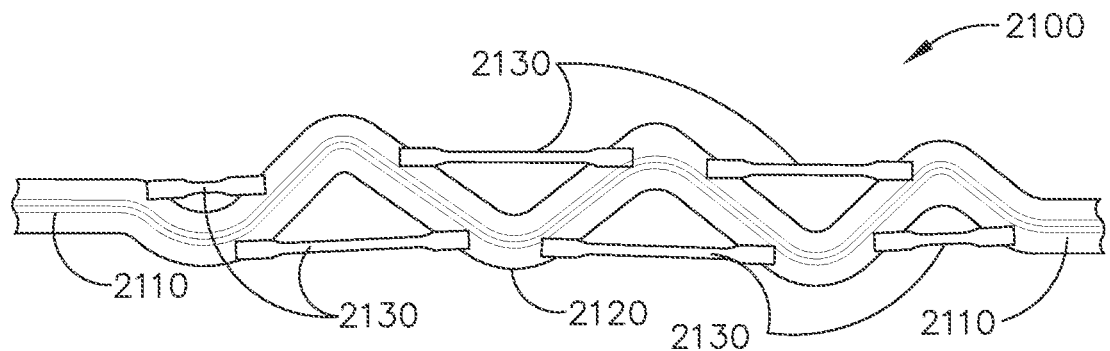
FIG. 17 is an elevational view of the flex circuit of FIG. 16, wherein the stretchable zone is illustrated in a stretched configuration.
Figure 18:
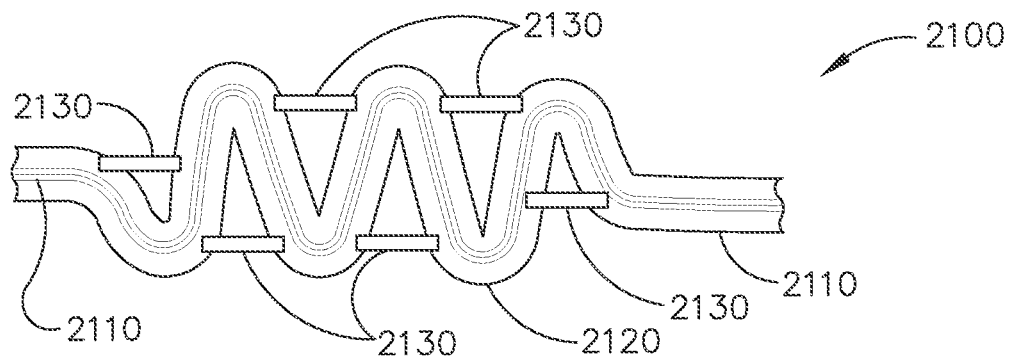
FIG. 18 is an elevational view of the flex circuit of FIG. 16, wherein the stretchable zone is illustrated in a non-stretched configuration.

In at least one instance, a configuration is provided that ensures the stretchable zones re-assume the proper neutral configuration after the load which stretched the stretchable zones is relaxed. FIGS. 16-18 depict a flex circuit 2100 comprising non-stretchable zones 2110 and a stretchable zone 2120 positioned between the non-stretchable zones 2110. The stretchable zone 2120 comprise a plurality of elastic strut, or connection, members 2130 attaching portions of the flex circuit 2100 within the stretchable zone 2120 together. FIG. 16 illustrates the stretchable zone 2120 in a relaxed state. In such a state, the elastic strut members 2130 and the stretchable zone 2120 of the flex circuit 2100 are in a neutral, un-loaded state. In at least one instance, the elastic strut members 2130 are configured to be in tension in the neutral, un-loaded state. Once the stretchable zone 2120 is stretched (FIG. 17), the elastic strut members 2130 are also stretched in the same direction and orientation that the stretchable zone 2120 is stretched. In this stretched state, the elastic strut members 2130 can ensure the integrity of the stretchable zone 2120 by carrying at least some of the force load and controlling the relative positioning of the zones. When the load that is stretching the stretchable zone 2120 is relaxed, the stretchable zone 2120 can be encouraged to its original neutral, un-loaded state (FIG. 18) by the elastic strut members 2130. In at least one instance, the elastic strut members 2130 can be used to ensure that the stretchable zone 2120 is not overstretched.

As can be seen in FIGS. 16-18, the elastic strut members 2130 are oriented in the same direction along a predetermined stretched direction. The elastic strut members 2130 may comprise a material and construction that is designed to only stretch in the intended stretch direction to increase the predictability of the elastic strut members 2130. In at least one instance, the elastic strut members 2130 are oriented in a crisscross configuration. Such a configuration may increase the tensile force provided by the elastic strut members 2130.

In at least one instance, as described in greater detail herein, a stretchable zone of a flex circuit can be used to measure a parameter of an actuator. For example, the stretchable zone can be attached to a fixed location and an actuator such that the actuator stretches the stretchable zone as the actuator is actuated. A sensor arrangement, such as a Hall Effect sensor positioned at on the fixed attachment, or index, location and a magnet positioned on the actuator attachment location, for example, can be used to measure displacement, for example, of the actuator as the actuator moves through an actuation stroke.

In various instances, surgical instrument assemblies comprise a flex circuit attached to a fixed location of a shaft of the surgical instrument assembly and one or more locations of an actuation member of the surgical instrument assembly. The flex circuit can comprise one or more sections extending from the portion fixed to the shaft which wrap around the shaft in a coiled pattern. One section wrapped around the shaft is wrapped around the shaft a half turn more than the other section so that it extends in the opposite direction from the other section. The flex circuit is spring biased into the coiled pattern. The flex circuit is configured to be pulled by the actuator to unwrap relative to the shaft and stretch across a length of the shaft. When the load on the flex circuit is relaxed, the flex circuit is configured to re-wrap itself around the shaft back into its coiled pattern. In at least one instance, the shaft is configured to translate to actuate a function of the surgical instrument assembly. In various instances, the shaft is rotatable and/or articulatable and, in other instances, the shaft is fixed.

In various instances, joints within a surgical instrument assembly such as an articulation joint and/or a rotation joint where multiple drive members are connected to each other comprise means for protecting wiring harnesses and/or flex circuits, for example, extending through and/or around the joints. The wiring harnesses are protected from induced stress and strains through the full range of motion of the joints. In at least one instance, the wiring harness comprises a pre-bent section that extends through an articulation joint. In such an instance, the pre-bent section is formed in a manner in anticipation of how the wiring harness will react as an end effector is articulated about the articulation joint.

FIGS. 19 and 20 depict a surgical instrument assembly 2200 comprising a shaft 2201 and a flex circuit, or wiring harness, 2210 extending through the shaft 2201. The flex circuit 2210 comprises a pre-bent section 2220 configured to be positioned near a joint within the surgical instrument assembly 2200. In at least one instance, the pre-bent configuration of the pre-bent section 2220 provides slack in a manner that accommodates the bending of components around the joint near which the pre-bent section 2220 is positioned. In at least one instance, the pre-bent section 2220 provides space for components. In at least one instance, the pre-bent section 2220 comprises one or more portions fixed to components of the surgical instrument assembly 2200 at and/or near the joint. In at least one instance, the pre-bent section 2220 is configured to be flexed, or bent, by the components to which it is attached as the components are actuated within the surgical instrument assembly 2200.

As can be seen in FIG. 20, the pre-bent section 2220 of the flex circuit 2210 resides in multiple flex-circuit profile planes 2221. A flex circuit profile plane is considered to be a plane defined by a substrate layer of the flex circuit itself. In at least one instance, the flex circuit 2210 is configured to only substantially bend in a flex circuit bend plane. As can be seen in FIGS. 19 and 20, the pre-bent section 2220 of the flex circuit 2210 comprises multiple bends in the flex circuit bend plane. In at least one instance, the flex circuit 2210 can bend slightly outside of the flex circuit bend plane.

FIGS. 21 and 22 depict a surgical instrument assembly 2300 comprising a shaft 2301 and a flex circuit, or wiring harness, 2310 extending through the shaft 2301. The flex circuit 2310 comprises a pre-bent section 2320 configured to be positioned near a joint within the surgical instrument assembly 2300. In at least one instance, the pre-bent configuration of the pre-bent section 2320 provides slack in a manner that accommodates the bending of components around the joint near which the pre-bent section 2320 is positioned. In at least one instance, the pre-bent section 2320 provides space within the shaft for other components in the shaft. In at least one instance, the pre-bent section 2320 comprises one or more portions fixed to components of the surgical instrument assembly 2300 at and/or near the joint. In at least one instance, the pre-bent section 2320 is configured to be flexed, or bent, by the components to which it is attached as the components are actuated within the surgical instrument assembly 2200.

As can be seen in FIG. 22, the pre-bent section 2320 of the flex circuit 2310 resides in multiple flex-circuit profile planes 2321. A flex circuit profile plane is considered to be a plane defined by a substrate layer of the flex circuit itself. In at least one instance, the flex circuit 2310 is configured to only substantially bend in a flex circuit bend plane. As can be seen in FIGS. 21 and 22, the pre-bent section 2320 of the flex circuit 2310 comprises multiple bends in the flex circuit bend plane. In at least one instance, the flex circuit 2310 can bend slightly outside of the flex circuit bend plane.

Still referring to FIGS. 21 and 22, the flex circuit 2310 comprises an off-centered section 2323 which comprises a section of flex circuit that is off-centered laterally with respect to a shaft axis. Such positioning can provide space within the shaft for other shaft components in certain areas. In this instance, the pre-bent section 2320 is offset relative to the shaft axis to bypass on-center drivers 2303. Various surgical instrument systems such as surgical stapling end effectors, for example, require on-center drive systems owing to the high operational loads required to fire the surgical stapling end effectors. In such systems, the off-center flex circuit 2310 can provide space for such on-center drive systems.

FIGS. 23 and 24 depict a surgical instrument assembly 2400 comprising a shaft 2401 and a flex circuit, or wiring harness, 2410 extending through the shaft 2401. The flex circuit 2410 comprises a pre-curved section 2420. In at least one instance, the pre-curved section 2420 is configured to be positioned near a joint within the surgical instrument assembly 2400. In at least one instance, the pre-curved section 2420 provides space within the shaft for other components. In at least one instance, the pre-curved section 2420 is mounted to an inner surface of the shaft 2401 such that the pre-curved section 2420 conforms to the tubular shape of the shaft 2401.

As can be seen in FIG. 24, the pre-curved section 2420 of the flex circuit 2410 resides in a single flex-circuit profile plane 2421. In at least one instance, this single flex-circuit profile plane 2421 conforms to the tubular shape of the shaft 2401. A flex circuit profile plane is considered to be a plane defined by a substrate layer of the flex circuit itself. In at least one instance, the flex circuit 2410 is configured to only substantially bend in a flex circuit bend plane. As can be seen in FIGS. 23 and 24, the pre-curved section 2420 of the flex circuit 2410 is shaped to bend along the tubular shape of the shaft 2401 as well as in a flex circuit bend plane which is transverse to the flex-circuit profile plane 2421. Such bending can be advantageous near an articulation joint to control the movement of the flex circuit 2410 within the shaft.

Still referring to FIGS. 23 and 24, the flex circuit 2410 comprises an off-centered section 2423 which comprises a section of flex circuit that is off-centered laterally with respect to the longitudinal axis of the shaft. Such positioning can provide space for other shaft components in certain areas. In this instance, the pre-curved section 2420 is offset relative to the shaft axis to bypass on-center drivers 2403. Various surgical instrument systems such as surgical stapling end effectors, for example, often require on-center drive systems, i.e., drive systems oriented along the longitudinal axis of the shaft, owing to the high operational loads required to fire the surgical stapling end effectors. The flex circuit 2410 can provide space for such on-center drive systems. In at least one instance, a flex circuit for use in a shaft of a surgical instrument assembly is configured to bend in multiple planes and directions corresponding to the bending planes of joints and/or components of the surgical instrument assembly.

In at least one instance, the flex circuits are fabricated with pre-bent and/or pre-curved sections such that the pre-bent and/or pre-curved sections are not required to be bent or curved into this configuration during use. In various instances, a pre-curved section comprises a portion of the flex circuit that is in a curved configuration when the flex circuit is not under load. Under load, the pre-curved section can curve further and/or straighten under load.

Figure 25:
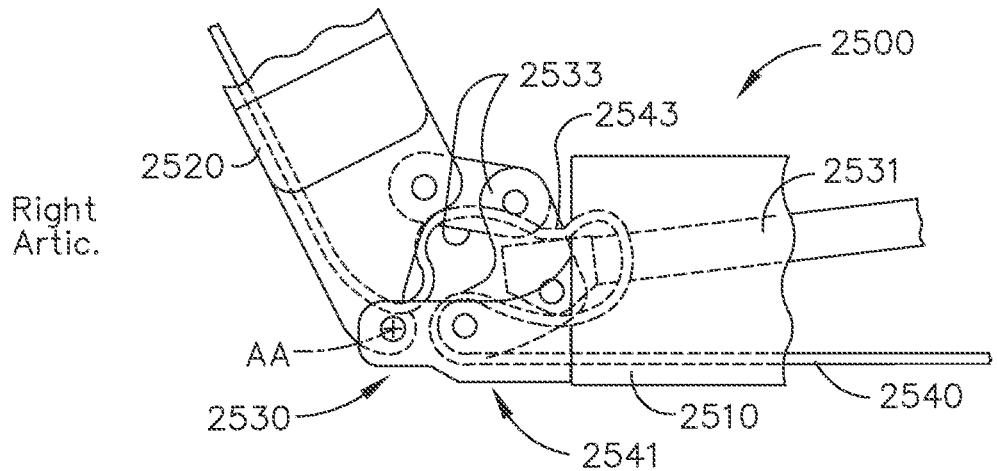
FIG. 25 is a plan view of a surgical instrument assembly, illustrated with components removed, comprising an articulation joint and a flex circuit extending through the articulation joint, wherein the surgical instrument assembly is illustrated in a first articulated configuration.
Figure 26:
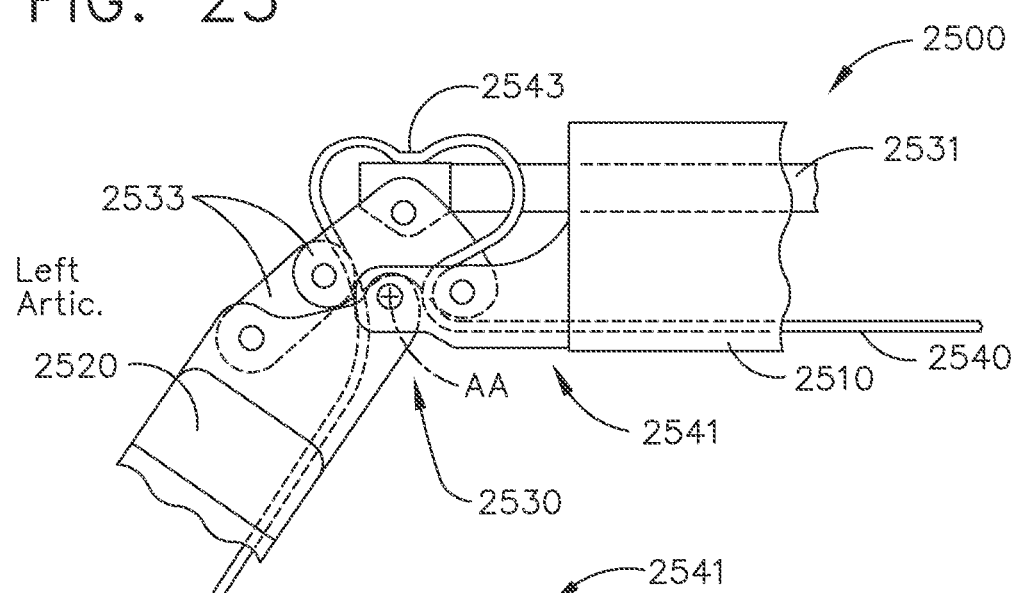
FIG. 26 is a plan view of the surgical instrument assembly of FIG. 25, wherein the surgical instrument assembly is illustrated in a second articulated configuration.
Figure 27:
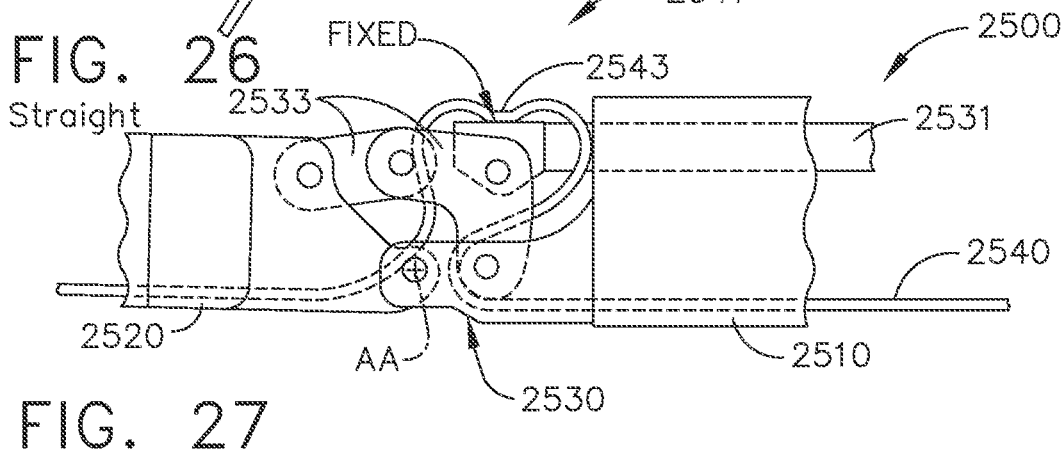
FIG. 27 is a plan view of the surgical instrument assembly of FIG. 25, wherein the surgical instrument assembly is illustrated in a non-articulated configuration.

FIGS. 25-27 depict a surgical instrument assembly 2500 comprising a shaft 2510, an articulation joint 2530, and an end effector 2520 attached to the shaft 2510 by way of the articulation joint 2530. The end effector 2520 is configured to be articulated relative to the shaft 2510 with articulation links 2533 coupled to an articulation driver 2531. The articulation links are connected to the shaft 2510, the end effector 2520, and the articulation driver 2531. When the articulation driver 2531 is actuated, the end effector 2520 is rotated about the articulation axis AA by way of the articulation links 2533.

The surgical instrument assembly 2500 further comprises a flex circuit 2540 extending through the shaft 2510, the articulation joint 2530, and into the end effector 2520. The flex circuit 2540 can be used for any suitable electrical connection that is distal to the articulation joint 2530. In at least one instance, the flex circuit 2540 comprises fixed attachment points within the shaft 2510 and the end effector 2520. In various instances, flex circuits comprise a substantial width and need to be routed through various moving components. The flex circuit 2540 comprises a pre-bent section 2541 routed through the articulation joint 2530 of the surgical instrument assembly 2500. The flex circuit 2540 extends through the articulation links 2533 and comprises an attachment portion 2543 attached to the articulation driver 2531. As the end effector 2520 is articulated about the articulation axis AA, the pre-bent section 2543 conforms to the movement of the articulation links 2533, the end effector 2520, the articulation driver 2531, and the shaft 2510. The articulation driver 2531 is configured to guide the pre-bent section 2541 by way of the attachment portion 2543 into suitable configurations as the end effector 2520 is articulated about the articulation axis AA. The pre-bent section 2541 permits slack, or slop, proximal to the attachment portion 2543 and distal to the attachment portion 2543 to prevent any possible strain on the flex circuit 2540.

In at least one instance, the flex circuit 2540 comprises one or more S-shaped portions. In at least one instance, one or more bends of each S-shaped portion is fixed to a moving component of the surgical instrument assembly 2500. In at least one instance, the flex circuit 2540 comprises a plurality of elastic strut members configured to bias the pre-bent section 2541 into its neutral pre-bent configuration as seen in FIG. 27 when the end effector 2520 is not in an articulated position. A flex circuit having integrated moving component support locations can provide a greater degree of stability through regions of a surgical instrument assembly that comprises moving regions such as articulation joints, for example.

Figure 28:
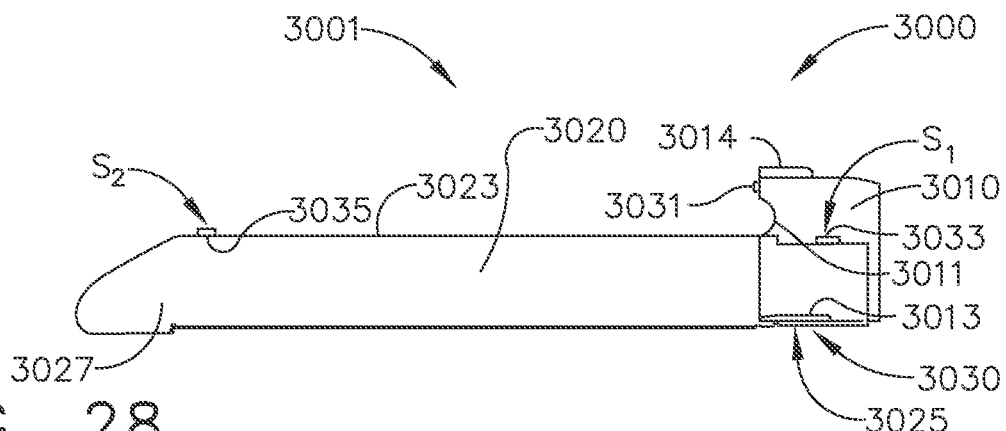
FIG. 28 is an elevational view of a surgical instrument assembly, illustrated with components removed, comprising an end effector, a firing member, and a sensing system comprising a plurality of sensors and a magnet.
Figure 29:
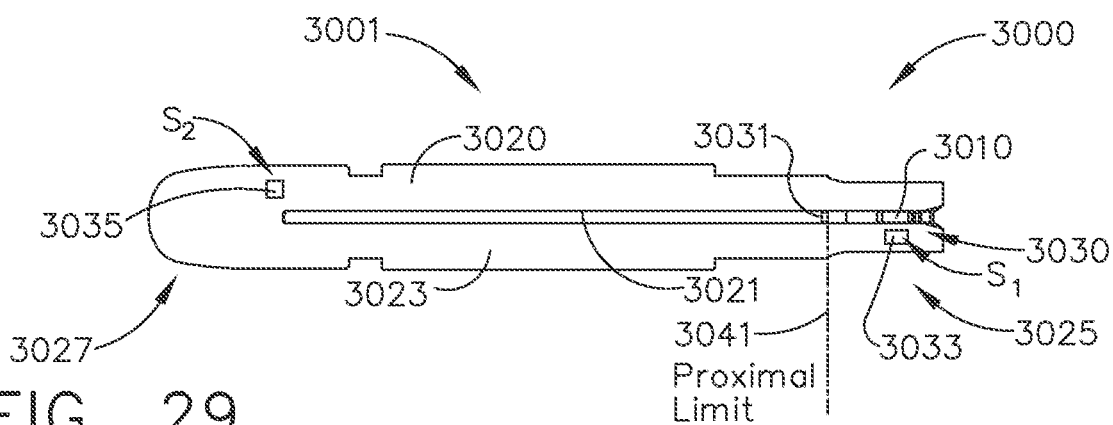
FIG. 29 is a plan view of the surgical instrument assembly of FIG. 28, wherein the firing member is in an unfired position.
Figure 30:
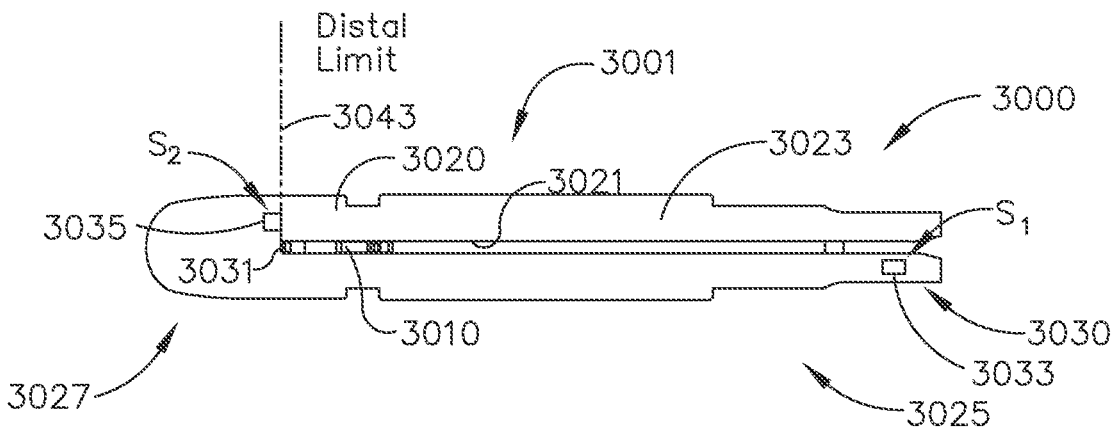
FIG. 30 is a plan view of the surgical instrument assembly of FIG. 28, wherein the firing member is in a fired position.
Figure 34:
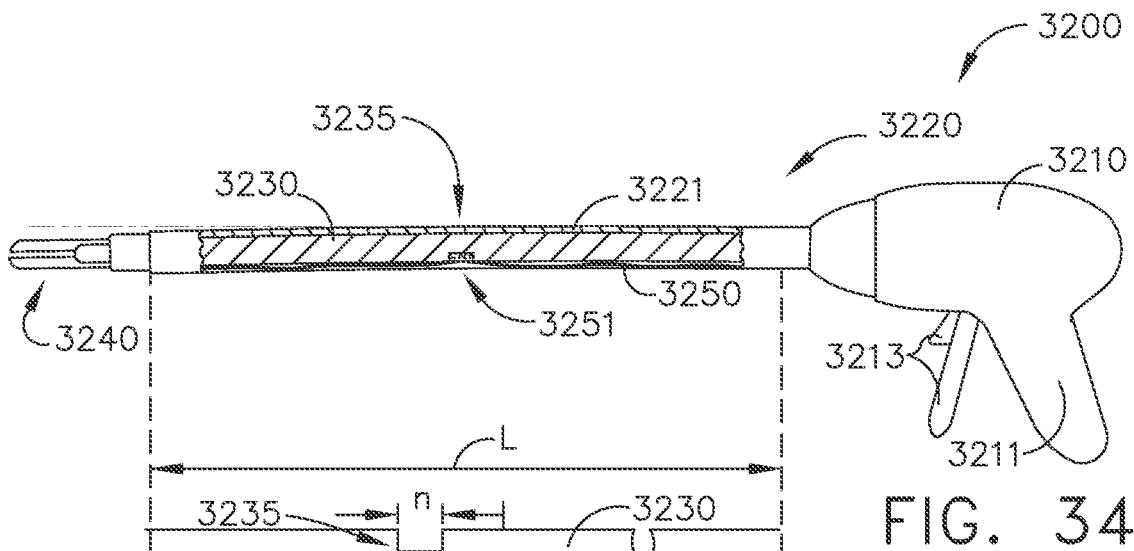
FIG. 34 is a perspective view of a surgical instrument assembly comprising a handle, a shaft extending from the handle, an end effector extending from the shaft, and a flex circuit extending through the shaft and comprising a sensing system.

FIGS. 28-30 depict a surgical instrument assembly 3000 comprising an end effector 3001, a firing member 3010, and a sensing system 3030 configured to sense a parameter of the firing member 3010. The end effector 3001 comprises a staple cartridge 3020 including a plurality of staples stored therein. The staple cartridge 3020 comprises a longitudinal slot 3021 configured to receive the firing member 3010 therein, a tissue-supporting surface, or deck, 3023, a proximal end 3025, and a distal end 3027. The firing member 3010 is configured to eject the staples and cut patient tissue compressed against the deck 3023 during a staple-firing stroke as the firing member is advanced from the proximal end 3025 to the distal end 3027. The firing member 3010 comprises a cutting edge 3011, a lower camming member 3013 configured to engage a lower jaw of the end effector 3001, and an upper camming member 3014 configured to engage an upper jaw of the end effector 3001.

The sensing system 3030 is configured to sense a parameter such as, for example, the displacement of the firing member 3010 as the firing member 3010 moves within the end effector 3001. The sensing system 3030 comprises a magnet 3031 and a plurality of sensors comprising a proximal sensor 3033 positioned on the tissue-supporting surface 3023 at the proximal end 3025 of the staple cartridge 3020 and a distal sensor 3035 positioned on the tissue-supporting surface 3023 at the distal end 3027 of the staple cartridge 3020. The sensors 3033, 3035 comprise Hall Effect sensors; however, any suitable sensor can be used. The magnet 3031 is positioned on the front of the firing member 3010. As the firing member moves through a firing stroke, the signals of the sensors 3033, 3035 are configured to fluctuate as the magnet 3031 moves toward and away from the sensors 3033, 3035. These signals can be used by a control circuit to interpret a parameter of the firing member 3010 such as displacement, velocity, and/or acceleration, for example. The magnet 3031 comprises a proximal limit 3041 (FIG. 29) adjacent the sensor 3033 and a distal limit 3043 (FIG. 30) adjacent the sensor 3035.

In at least one instance, a sled of a surgical stapling assembly is monitored utilizing Hall Effect sensors and magnets, for example. Any suitable movable actuation member can be sensed within a surgical instrument assembly utilizing the sensing system 3033. For example, a translating member within a bi-polar energy surgical instrument can be sensed utilizing the sensing system 3033. In at least one such embodiment, the translating member comprises a tissue cutting knife, for example.

In at least one instance, the sensing system 3033 is utilized in conjunction with a control circuit configured to adjust a motor control program. For example, the sensing system 3033 may detect that the firing member 3010 has not traveled an expected distance compared to a monitored motor movement while the surgical instrument assembly 3000 is in an articulated configuration. This can be due to an increased stroke length of an actuation member configured to move the firing member 3010 caused by the actuation member being articulated around an articulation joint. In such an instance, the control circuit is configured to adjust the motor control program to compensate for the increased stroke length caused by the articulation of the surgical instrument assembly 3000. In at least one instance, component wear can cause loss of stroke length within an actuation system. In such an instance, the control circuit is configured to adjust the motor control program to compensate for the loss of stroke length such that a full staple firing stroke can ultimately be completed.

FIGS. 31-33 depict a surgical instrument assembly 3100 comprising an end effector jaw 3101 comprising a staple cartridge channel 3110 configured to receive a staple cartridge 3140 therein and a sensing system 3130 configured to measure a parameter of the surgical instrument assembly 3100. The staple cartridge channel 3110 comprises a proximal end 3113, a distal end 3115, and a slot 3111 extending between the proximal end 3113 and the distal end 3115 configured to receive a portion of a firing member therein. The staple cartridge channel 3110 further comprises a bottom 3117 configured to support a bottom of the staple cartridge 3140.

The sensing system 3130 is configured to monitor pressure applied to the staple cartridge 3140. The sensing system 3130 comprises a plurality of pressure sensors comprising a first set of sensors 3131A positioned on a first side of the slot 3111 on the bottom 3117 of the cartridge channel 3110 and a second set of sensors 3131B positioned on a second side of the slot 3111 on the bottom 3117 of the cartridge channel 3110. In at least one instance, pressure sensors can be positioned on the sides of the cartridge channel in addition to or in lieu of sensors positioned on the bottom 3117 of the cartridge channel 3110. In at least one instance, an anvil jaw can comprise pressure sensors configured to detect pressure applied to the anvil jaw. In at least one instance, a pressure sensitive fabric and/or conductive thread can be laid on the bottom 3117 of the cartridge channel 3110. In at least one instance, a Velostat sensor can be used, for example; however, any suitable sensor can be used.

The sensing system 3130 is configured to detect pressure between the staple cartridge 3140 and the cartridge channel 3110. The sensors 3131A, 3131B are connected to a flex circuit 3120 configured to communicate the signals of the sensors 3131A, 3131B to a control circuit of the surgical instrument assembly 3100. The sensing system 3130 is configured to measure pressure corresponding to each side of the staple cartridge 3140 as well as pressure corresponding to a proximal end 3141 and a distal end 3143 of the staple cartridge 3140. A control circuit is configured to monitor the pressure sensed by the sensors 3131A, 3131B. In at least one instance, the control circuit is configured to map out, in real time, to a user geographically a pressure profile sensed by the sensing system 3130. Such a pressure profile can be displayed to a user, for example. In at least one instance, the control circuit is configured to automatically adjust a motor control program of a firing member based on signals received from the pressure sensors 3131A, 3131B. Oftentimes, the tissue compressed between the anvil jaw and the staple cartridge 3140 is not evenly compressed which creates an uneven pressure profile in the tissue and, in some instances, can affect the staple formation process. The sensors 3131A, 3131B are positioned and arranged to provide the control system with data regarding the pressure profile within the tissue. For instance, the control system can assess whether the tissue is thicker on the first side of the end effector as compared to the second side of the end effector. In at least one such instance, the control system is configured to slow down the staple firing stroke when the difference between the first side pressure and the second side pressure exceeds a threshold. In such instances, a slower staple firing stroke can result in better staple formation.

FIGS. 34-37 illustrate a surgical instrument assembly 3200 comprising a handle 3210, a shaft assembly 3220 extending from the handle 3210, and an end effector 3240 extending from the shaft assembly 3220. The handle 3210 comprises a plurality of actuators 3213 configured to be actuated by a user and a hold-able portion 3211 configured to be held by a user. The actuators 3213 are configured to actuate one or more actuation members within the shaft assembly 3220 to actuate a function of the end effector 3240.

The surgical instrument assembly 3200 further comprises a sensing system configured to detect a parameter of a shaft component 3230 extending through an outer shaft 3221 of the shaft assembly 3220. The shaft component 3230 comprises a plurality of apertures 3231 defined therein configured to slideably receive actuation members therein. In at least one instance, the shaft component 3230 is configured to experience a load during the actuation of one or more actuation systems within the surgical instrument assembly 3200. Any suitable component can be sensed by the sensing system. For example, a firing actuator, closure actuator, and/or articulation actuator may be sensed by such a sensing system. The sensing system comprises a flex circuit 3250 and a sensor 3253 extending from a sensor region 3251 of the flex circuit 3250. The sensor 3253 may comprise a strain gauge, for example; however, any suitable sensor can be used. In at least one instance, the flex circuit 3250 extends to the end effector 3240 where additional sensors are positioned and connected to flex circuit 3250. The shaft component 3230 comprises a channel 3233 defined therein within which the flex circuit 3250 is positioned.

Figure 35:
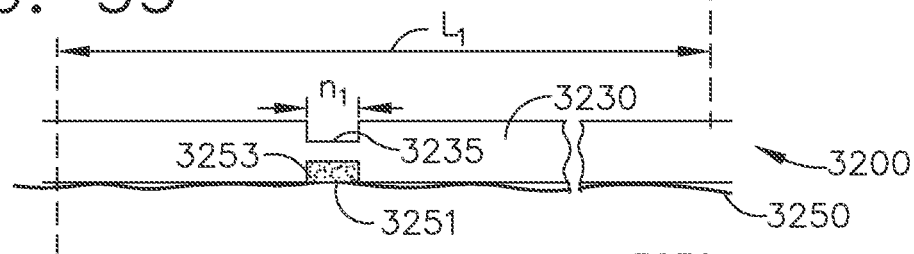
FIG. 35 is a partial elevational view of the surgical instrument assembly of FIG. 34, wherein an actuation member configured to be sensed by the sensing system comprises a first length.
Figure 36:
FIG. 36 is a partial elevational view of the surgical instrument assembly of FIG. 34, wherein the actuation member is under a load and comprises a second length different than the first length of FIG. 35.
Figure 37:
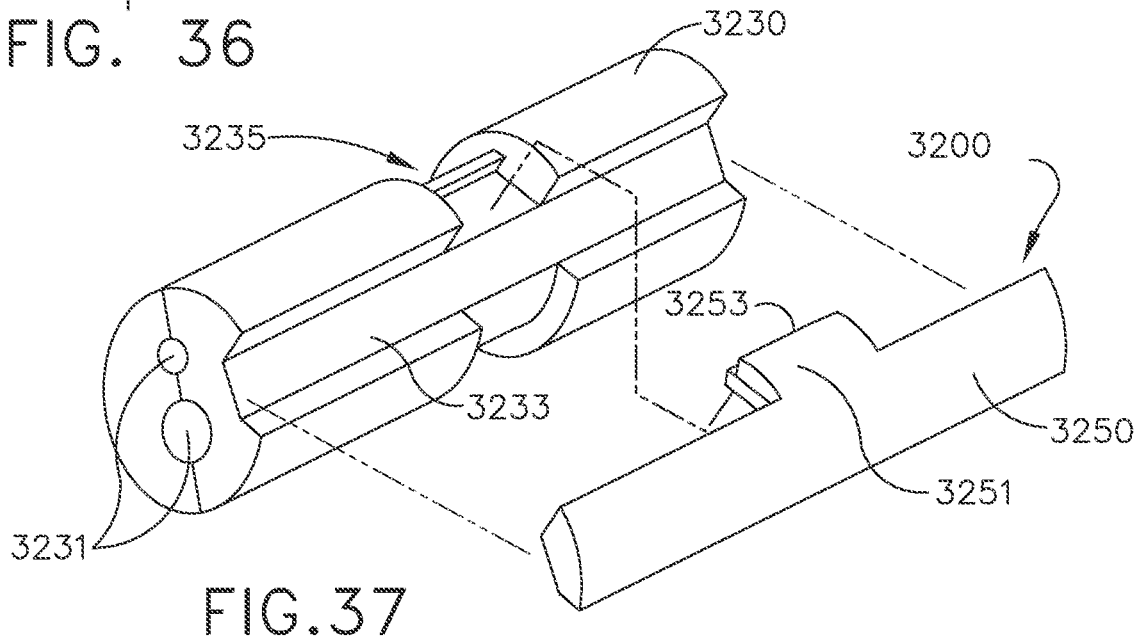
FIG. 37 is a partial exploded view of the surgical instrument assembly of FIG. 34.

In many instances, the measurement of tensile and compression forces and/or strains transmitted through a drive member is more reliable when they are measured toward the central axis of the drive member as opposed to the outer perimeter of the drive member. Stated another way, necking of the shaft component can also provide a more localized concentration of stress and strain. To this end, the sensor 3253 is mounted to a necked portion 3235 of the shaft component 3230. A region comprising such necking can provide a more dependable region for a sensor to measure a load applied to the shaft component 3230 because even the slightest of load applied to the shaft component 3230 will result in an amplified strain in the necked portion 3235. As can be seen in FIG. 35, the shaft component 3230 is unloaded and the necked portion 3235 comprises a first width and the shaft component 3230 comprises a first length. In FIG. 36, the shaft component 3230 is loaded and the necked portion 3235 is elongated resulting in the necked portion 3235 comprising a second width that is greater than the first width and the shaft component 3230 comprising a second length that is greater than the first length. In at least one instance, the stretching of the shaft component 3230 can be determined by a control circuit interpreting a change in strain values received from the sensor 3253 as the shaft component 3230 is loaded and unloaded.

In various instances, the sensor 3253 does not change the overall shape and/or properties of the shaft component 3230. In at least one instance, the flex circuit and/or sensors 3253 are embedded in recesses in the shaft component 3230 such that the overall dimension of the shaft component 3230 is not changed by the flex circuit and/or sensors 3253. For instance, the thickness of the flex circuit and/or sensors 3253 is equal to or less than the depth of the recess. Such an arrangement can allow a structural component to maintain its integrity while its properties are monitored locally within the shaft assembly 3220.

In at least one instance, strain gauges extending from a flex circuit are attached to several different components within a shaft assembly. In at least one instance, a portion of a flex circuit extending through a shaft assembly is primarily non-stretchable and another portion of the flex circuit is stretchable. In various instances, the primarily non-stretchable portion has a higher modulus of elasticity than the other portions of the flex circuit. In at least one instance, the modulus of elasticity of the primarily non-stretchable portion is 10 times higher than the modulus of elasticity of the other portions of the flex circuit, for example. In at least one instance, the modulus of elasticity of the primarily non-stretchable portion is 100 times higher than the modulus of elasticity of the other portions of the flex circuit, for example. In at least one instance, the stretchable portion of the flex circuit is used to sense a parameter of a component of a shaft assembly. In at least one instance, the stretchable portion of the flex circuit comprises a substrate material that is thinner than the substrate material that makes up the non-stretchable portion. In at least one instance, the substrate material used for the stretchable portion of the flex circuit is different than the substrate material for the non-stretchable portion of the flex circuit. In at least one instance, conductors within the flex circuit are used as resistive elements to sense stretch. Such conductors can be used to measure a parameter of a structural component within a shaft assembly and/or end effector, for example. In at least one instance, a force experienced by a sensed structural member is proportionate to the strain experienced by the sensed structural member which may be detected using any of the methods disclosed herein.

In at least one instance, a stretchable portion of a flex circuit used to detect a parameter of a structural member within a shaft assembly comprises a length that is spread out across the entire length of the structural member itself so as to maintain a homogenous stretch along the length of the structural member. For example, if only a portion of the structural member is in contact with a stretchable portion of a flex circuit, that portion may be strengthened by the additional material of the stretchable portion of the flex circuit and this may inadvertently fluctuate the sensor readings within that region relative to the region that is not in contact with the stretchable portion of the flex circuit. In at least one instance, this is avoided by covering the entire length of the structural member with a stretchable flex circuit portion. In at least one instance, a stretchable flex circuit portion is used to strengthen a portion of a structural member to be sensed.

In at least one instance, a structural member to be sensed comprises features to concentrate force experienced by the structural member, direct the force experienced by the structural member in a specific direction, and/or amplify the load experienced by the structural member across its length. In various instances, directing and/or amplifying the flow of strain through a drive member can be accomplished by changes in the cross-section and/or geometry of the drive member.

In at least one instance, strain experienced by a structural component of a shaft assembly owing to bending can be sensed by a strain gauge positioned at the farthest location from the bending axis. Positioning such an integrated flex circuit strain gauge can amplify the detectable stress on the bending structural component. In at least one instance, this location is artificially created. An artificially created fin may extend from a structural component where the fin creates a position further from a bending axis of the structural component than any portion of the structural component itself.

In at least one instance, a control circuit is configured to monitor a parameter of the structural component to be sensed by a sensing system within the shaft assembly and is configured to adjust the operation of the surgical instrument assembly in any suitable way, including those disclosed herein.

Figure 38:
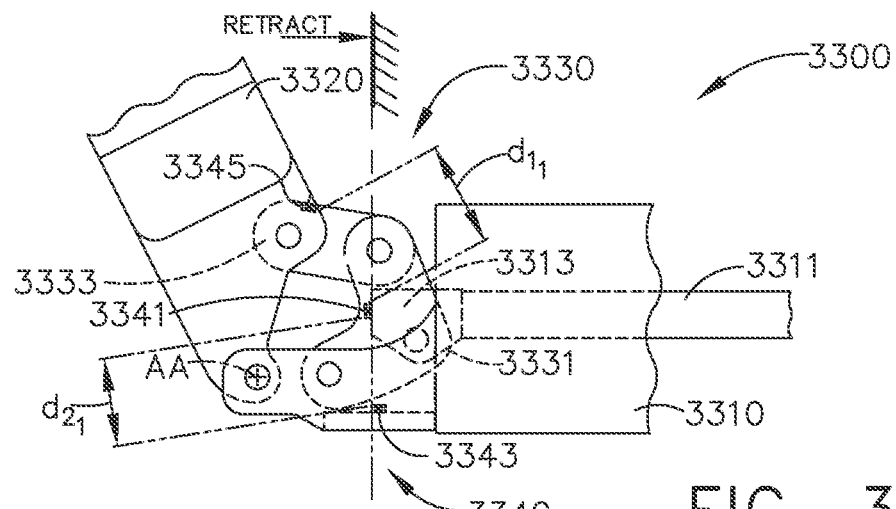
FIG. 38 is a plan view of a surgical instrument assembly, illustrated with components removed, comprising a shaft, an articulation joint, an end effector attached to the shaft by way of the articulation joint, and a sensing system, wherein the surgical instrument assembly is in a first articulated configuration.
Figure 39:
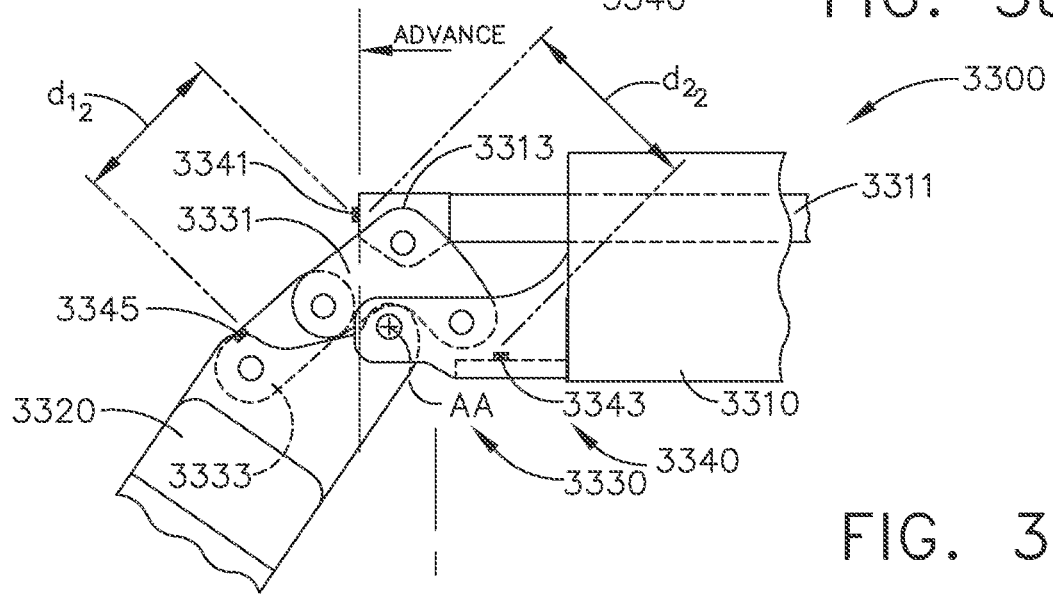
FIG. 39 is a plan view of the surgical instrument assembly of FIG. 38, wherein the surgical instrument assembly is in a second articulated configuration.
Figure 40:
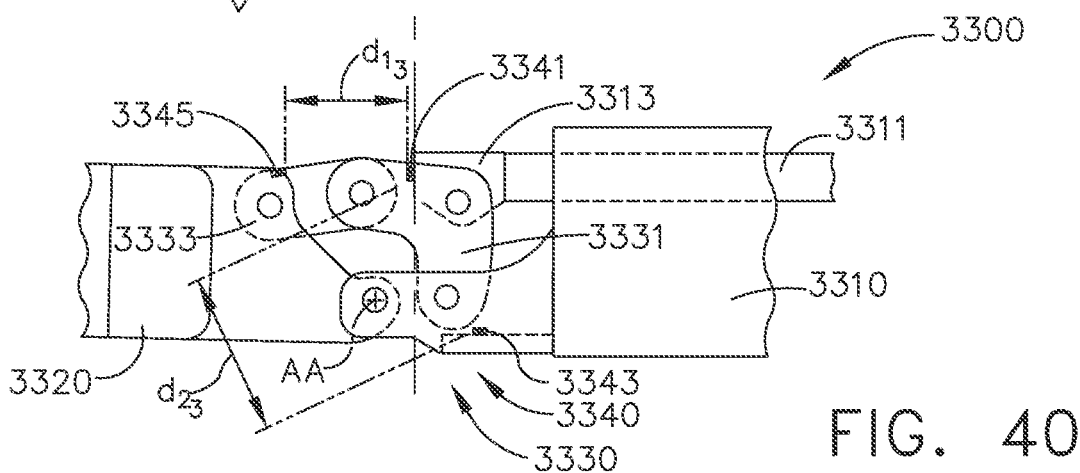
FIG. 40 is a plan view of the surgical instrument assembly of FIG. 38, wherein the surgical instrument assembly is in a non-articulated configuration.

In various instances, the local displacement sensing of a shaft component within a shaft assembly of a surgical instrument assembly can be used to determine the beginning and end of a stroke of the component being sensed. FIGS. 38-40 depict a surgical instrument assembly 3300 comprising a shaft 3310, an articulation joint 3330, an end effector 3320 pivotally coupled to the shaft 3310 about the articulation joint 3330. The surgical instrument assembly 3300 further comprises a sensing system 3340 configured to monitor the displacement of an articulation actuator 3311 configured to articulate the end effector 3320 relative to the shaft 3310 about an articulation axis AA.

The articulation joint 3330 comprises a first articulation link 3331 connected to the articulation actuator 3311 and the shaft 3310 and a second articulation link 3333 connected to the first articulation link 3331 and the end effector 3320. The articulation actuator 3311 is configured to be advanced and retracted longitudinally within the shaft 3310 to pivot the end effector 3320 about the articulation axis AA. The first articulation link 3331 is pivotally coupled to the shaft 3310, the articulation actuator 3331, and the second articulation link 3333. The second articulation link 3333 is pivotally coupled to the first articulation link 3331 and the end effector 3320.

The sensing system 3340 comprises a sensor 3341 positioned on a distal end 3313 of the articulation actuator 3311, a first magnet 3343 positioned on the shaft 3310, and a second magnet 3345 positioned on the second articulation link 3333. The sensor 3341 comprises a Hall Effect sensor; however, any suitable sensor and trigger arrangement may be used. For example, an inductive sensor arrangement can be used. A control circuit is configured to monitor signals received by the sensor 3341 to determine the exact articulated position of the end effector 3320 relative to the shaft 3310. As the articulation actuator 3311 is moved through an articulation stroke, the sensor 3341 is moved within a magnetic field that is being altered by the magnets 3343, 3345 thereby resulting in a variance of signal of the sensor 3341. This variance in signal can be interpreted by a control circuit by comparing the signal to a range of expected signals and articulated positions to determine the exact articulated position of the end effector 3320 relative to the shaft 3310.

FIG. 38 illustrates the end effector 3320 in a first articulated position where the articulation actuator 3331 is actuated in a fully-proximal position. In this configuration, the first magnet 3343 is a first distance $d_{21}$ from the sensor 3341 and the second magnet 3345 is a second distance $d_{11}$ from the sensor 3341. A control circuit is configured to determine the position of the magnets 3343, 3345 by interpreting the signal from the Hall Effect sensor 3341. This can be achieved by comparing the signal to an expected range of signals corresponding to known actuation positions as discussed above. FIG. 39 illustrates the end effector 3320 in a second articulated position where the articulation actuator 3331 is actuated in a fully-distal position. In this configuration, the first magnet 3343 is a first distance $d_{22}$ from the sensor 3341 and the second magnet 3345 is a second distance $d_{12}$ from the sensor 3341. A control circuit is configured to determine the position of the magnets 3343, 3345 by interpreting the signal from the Hall Effect sensor 3341. FIG. 40 illustrates the end effector 3320 in a non-articulated position. In this configuration, the first magnet 3343 is a first distance $d_{23}$ from the sensor 3341 and the second magnet 3345 is a second distance $d_{13}$ from the sensor 3341. A control circuit is configured to determine the position of the magnets 3343, 3345 by interpreting the signal from the Hall Effect sensor 3341.

The sensing system 3340 can be used by a control circuit to determine the actual position of the end effector 3320 relative to the shaft 3310 without having to monitor the output of the articulation drive system motor. In at least one instance, the control circuit is configured to automatically adjust a motor control program configured to actuate the articulation actuator 3311 according to a desired outcome based on the monitored position of the end effector 3320. For example, a user may instruct the instrument to place the end effector 3320 in a non-articulated configuration. The sensing system 3340 can be used to determine the actual position of the end effector 3320. If the end effector 3320 does not fully attain the desired position, the control circuit can be configured to alert a user and/or automatically adjust the motor control program to actuate the articulation actuator 3311 until the sensing system 3340 detects the end effector 3320 in the desired position.

A sensing system such as the sensing system 3340, for example, that measures a distal-most movable actuation component can provide a greater degree of accuracy compared to sensing systems that measure intermediate movable actuation components. For example, when measuring a movable actuation component upstream of the distal-most movable actuation component, the sensing system may not be able to detect any slop or backlash in the system downstream of the intermediate component being sensed. Measuring the distal-most movable actuation component of a drive system ensures that all variance in the drive system is detected and, thus, can be compensated for, for example. In at least one instance, the second magnet 3345 is positioned on the end effector 3320 itself.

In at least one instance, the inertia and/or friction of a kinematic system within a surgical instrument assembly is configured to be monitored. In at least one instance, a control circuit is configured to adjust a motor control program corresponding to the monitored kinematic system. In at least one instance, adjustments can be performed to minimize excessive loading on a drive member, eliminate an impact event of a drive member, and/or ensure complete actuation strokes of a drive member, for example.

In at least one instance, a control circuit is configured to monitor local displacement and velocity of a drive member as well as motor current of a motor configured to actuate the drive member. These parameters can be monitored during an acceleration and/or braking event of the drive member to determine an inertia of the system. The control circuit can then determine if the determined inertia is different from an expected inertia. As a result, inertia detection can be used to adjust a control program of the motor to more accurately execute such breaking and/or acceleration events of the drive member. In at least one instance, a control circuit is configured to alter the initiation timing of a braking cycle of a drive member based on the determined inertia of a previous braking cycle of the drive member.

In at least one instance, a control circuit is configured to prevent a high load impact event within a surgical stapling end effector based on a monitored inertia of a firing system within the surgical stapling end effector. The control circuit can further be configured to ensure a complete actuation cycle of the firing system even after an adjustment to a braking cycle is made to prevent the high load impact event. In at least one instance, retraction strokes also come with a risk of a high load impact event at a proximal end of the retraction stroke. In at least one instance, a control circuit is also configured to prevent proximal end high load impact events.

In at least one instance, a control circuit is configured to monitor a brake initiation trigger event such as, for example, at a determined stroke location and/or at a maximum force threshold. Both events may require a braking of a drive system. The control circuit is configured to learn the brake initiation triggers and can prevent the drive system from reaching the brake initiation triggers in subsequent firings of the drive system. In at least one instance, a brake timing is sped up to avoid a brake initiation trigger. In at least one instance, the brake timing is slowed down to avoid a brake initiation trigger. In at least one instance, a first test actuation could be performed within a surgical instrument assembly to determine inertia differences within the surgical instrument assembly compared to a nominal inertia of the surgical instrument assembly.

In various instances, a control circuit is provided to monitor friction within a drive system and adjust a motor control program accordingly. For example, a closure member of a surgical instrument can be monitored as the closure member clamps a jaw within an end effector. The acceleration, velocity, and/or displacement of the closure member can be monitored to map a closure event profile every time the closure member is actuated. The control circuit is configured to adjust the motor control program which actuates the closure member to ensure that the closure event profile is as consistent as possible through the life of the closure member during every closure stroke. The closure system may experience parasitic loss and wear over time resulting in a variance in the closure stroke of the system. The control circuit is configured to compensate for this. In at least one instance, the control circuit is configured to adjust the closure stroke based on tissue thickness and/or compressibility differences which can also be monitored.

Figure 41:
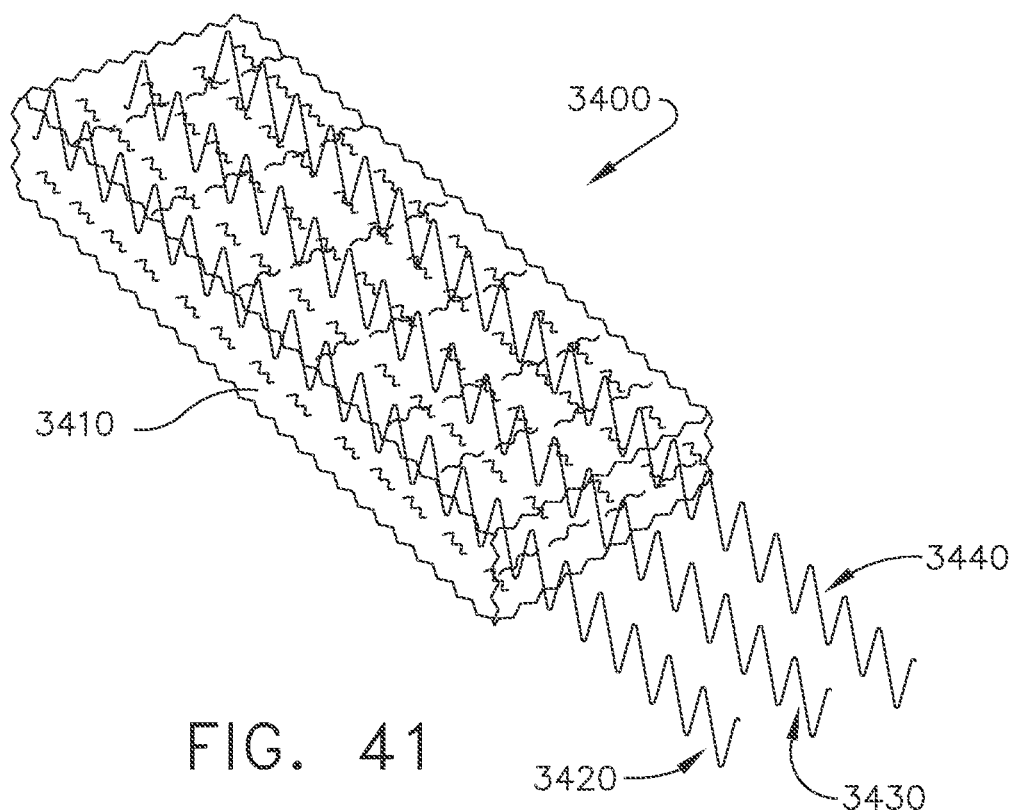
FIG. 41 is a perspective view of a stretchable sensing fabric comprising a body portion and a plurality of sensing materials positioned within the body portion.
Figure 42:
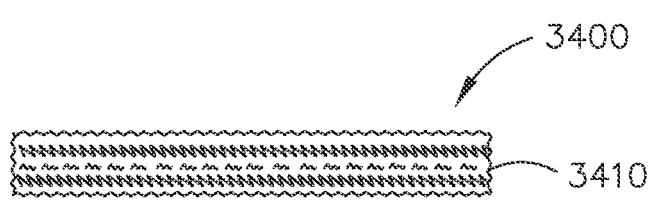
FIG. 42 is a plan view of the stretchable sensing fabric of FIG. 41, wherein the stretchable sensing fabric is in a relaxed configuration.
Figure 43:
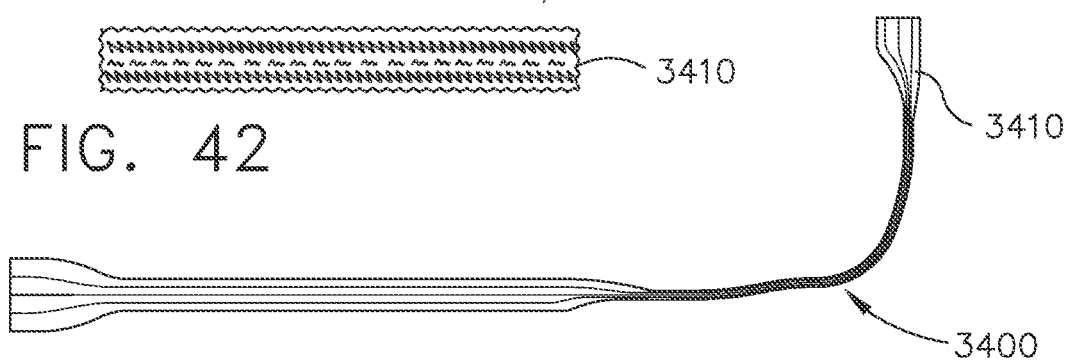
FIG. 43 is a plan view of the stretchable sensing fabric of FIG. 41, wherein the stretchable sensing fabric is in a stretched configuration.

FIGS. 41-43 depict a stretchable sensing fabric 3400 configured to sense one or more parameters of a surgical instrument assembly. The stretchable sensing fabric 3400 comprises a body portion 3410 and a plurality of sensing materials position within the body portion 3410. The plurality of sensing materials comprise a plurality of sensing fibers 3420, 3430, 3440 configured to sense one or more parameters of the surgical instrument assembly. In at least one instance, the sensing fibers 3420, 3430, 3440 are configured to measure pressure, bending stress, stretch, and/or shear force. The sensing fibers 3420, 3430, 3440 comprise electrically conductive material. In at least one instance, the fibers 3420, 3430, 3440 are interwoven into the body portion 3410 of the stretchable sensing fabric 3400. In at least one instance, the body portion 3410 comprises an elastic silicone, for example. In at least one instance, the fibers 3420, 3430, 3440 are placed into a mold for the body portion 3410 and the fibers 3420, 3430, 3440 are enveloped by a material of the body portion 3410. At any rate, the fibers 3420, 3430, 3440 are configured to stretch, twist, and/or bend with the body portion 3410. FIG. 42 illustrates the stretchable sensing fabric 3400 in a relaxed configuration and FIG. 43 illustrates the stretchable sensing fabric 3400 in a stretched configuration. The fibers 3420, 3430, 3440 are configured to be connected to an electrical circuit such that a control circuit can monitor the resistance of the fibers 3420, 3430, 3440 as the fibers 3420, 3430, 3440 change shape.

In at least one instance, the resistance of the fibers 3420, 3430, 3440 can be amplified or suppressed by connecting the fibers 3420, 3430, 3440 in parallel or in series. In at least one instance, each fiber 3420, 3430, 3440 comprises a different material. In at least one instance, the material of each fiber 3420, 3430, 3440 is selected based on its resistive properties. For example, when sensing a system with very little movement such as, for example, a closure member that may only move slightly through a closure stroke, a material and configuration may be selected that comprises a wide range of resistance variance with very little stretch.

In at least one instance, the fibers 3420, 3430, 3440 may be interlocked by weaving the fibers 3420, 3430, 3440 together, for example, to increase the available stretchable length of each fiber 3420, 3430, 3440. In at least one instance, the stretchable sensing fabric 3400 is attached by way of an adhesive only to a structural member to be sensed. In at least one instance, the stretchable sensing fabric 3400 is attached to a fixed location within a shaft, for example, and a structural member to be sensed such that the stretchable sensing fabric 3400 stretches relative to the shaft to which it is attached as the structural member moves relative to the shaft. In at least one instance, a supplemental spring is provided to increase or decrease sensitivity of the stretchable sensing fabric 3400.

In at least one instance, the fibers 3420, 3430, 3440 are oriented in multiple different directions and/or positioned in multiple different planes. In at least one instance, the stretchable sensing fabric 3400 comprises a full-bridge strain gauge configuration. In at least one instance, the stretchable sensing fabric 3400 comprises a half-bridge strain gauge configuration. In at least one instance, the stretchable sensing fabric 3400 comprises a quarter-bridge strain gauge configuration.

In at least one instance, the stretchable sensing fabric 3400 is used to monitor displacement, stress, and/or strain. Such parameters can be determined by a control circuit configured to interpret monitored resistance signals from the fibers within the sensing fabric 3400.

In at least one instance, the body portion 3410 comprises material properties that effect how the fibers 3420, 3430, 3440 stretch. In such an instance, the load applied to the body portion 3410 can be directly detected by the fibers 3420, 3430, 3440. In at least one instance, the stretchable sensing fabric 3400 comprises EeonTex conductive textile. In at least one instance, the stretchable sensing fabric 3400 comprises SHIELDEX metallized conductive fabric.

In at least one instance, a transparent portion is provided within a surgical instrument drive system. A drive member itself may comprise the transparent portion. In at least one instance, the transparent portion is a supplemental component integrated into the drive system. Optical light diffraction can be used to detect a load applied to the transparent portion by measuring the change in light within the transparent portion owing to the change in the transmissibility and/or reflectivity changes in the material when it is loaded and unloaded.

Figures 44, 45:
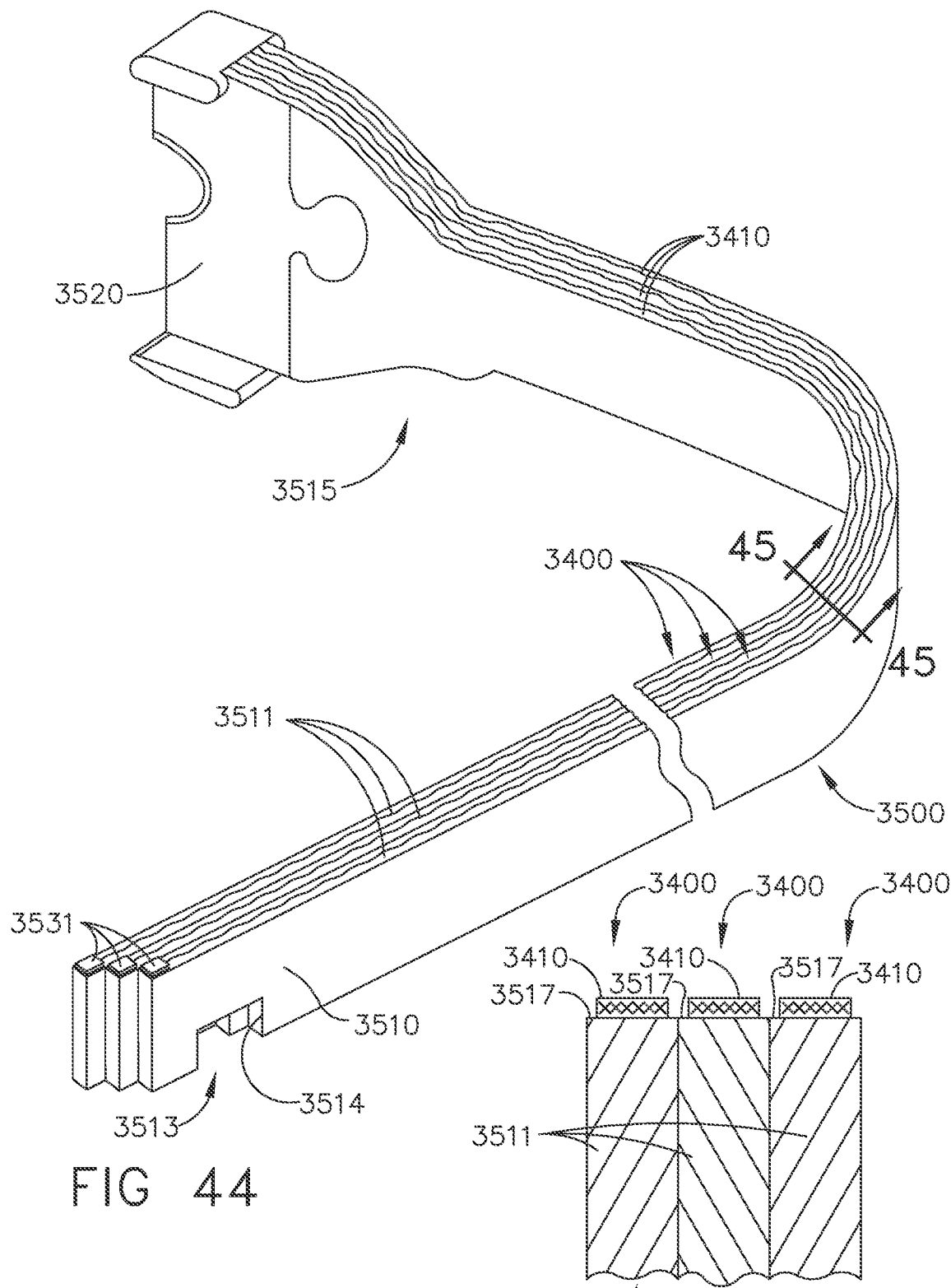
FIG. 44 is a perspective view of a surgical instrument assembly, illustrated with components removed, comprising a firing member and a plurality of the stretchable sensing fabric of FIG. 41.
FIG. 45 is a cross-sectional view of the surgical instrument assembly of FIG. 44.

In at least one instance, the stretchable sensing fabric 3400 can be used in conjunction with any movable drive members within a surgical instrument system. FIGS. 44 and 45 depict a surgical instrument assembly 3500 comprising a surgical stapling drive member 3510 configured for use with a surgical stapling instrument and a plurality of stretchable sensing fabrics 3400 positioned on the surgical stapling drive member 3510. The surgical stapling drive member 3510 comprises a plurality of bands 3511 stacked together and coupled to a firing member 3520 configured to cut tissue and deploy staples during a staple-firing stroke. As the bands 3511 are displaced around an articulation joint, the bands 3511 bend around the articulation joint and splay relative to each other. This bending can be detected by the stretchable sensing fabrics 3400 and can be correlated by the control system to the degree in which the end effector is articulated.

The stretchable sensing fabrics 3400 are positioned on the top 3517 of each band 3511. In at least one instance, the stretchable sensing fabrics 3400 are attached to each band 3511 with an adhesive, for example. In at least one instance, the attachment means for the stretchable sensing fabrics 3400 to each band 3511 does not affect the conductive fibers within the stretchable sensing fabrics 3400. The surgical instrument assembly 3500 further comprises electrical contacts 3531 configured to be coupled to the fabrics 3400 such that an electrical connection can be made with a flex circuit, for example. Each band 3511 further comprises a proximal engagement feature 3513 comprising a window 3514 configured to receive a firing drive system to actuate the surgical stapling drive member 3510. The fabrics 3400 can each stretch relative to each other to monitor one or more parameters of each band 3511 separately. Such a configuration can be used to monitor various parameters of articulation of an end effector. Such a configuration can also be used to detect a load applied to the firing member 3520 as the firing member 3520 is advanced through the staple-firing stroke.

Figure 46:
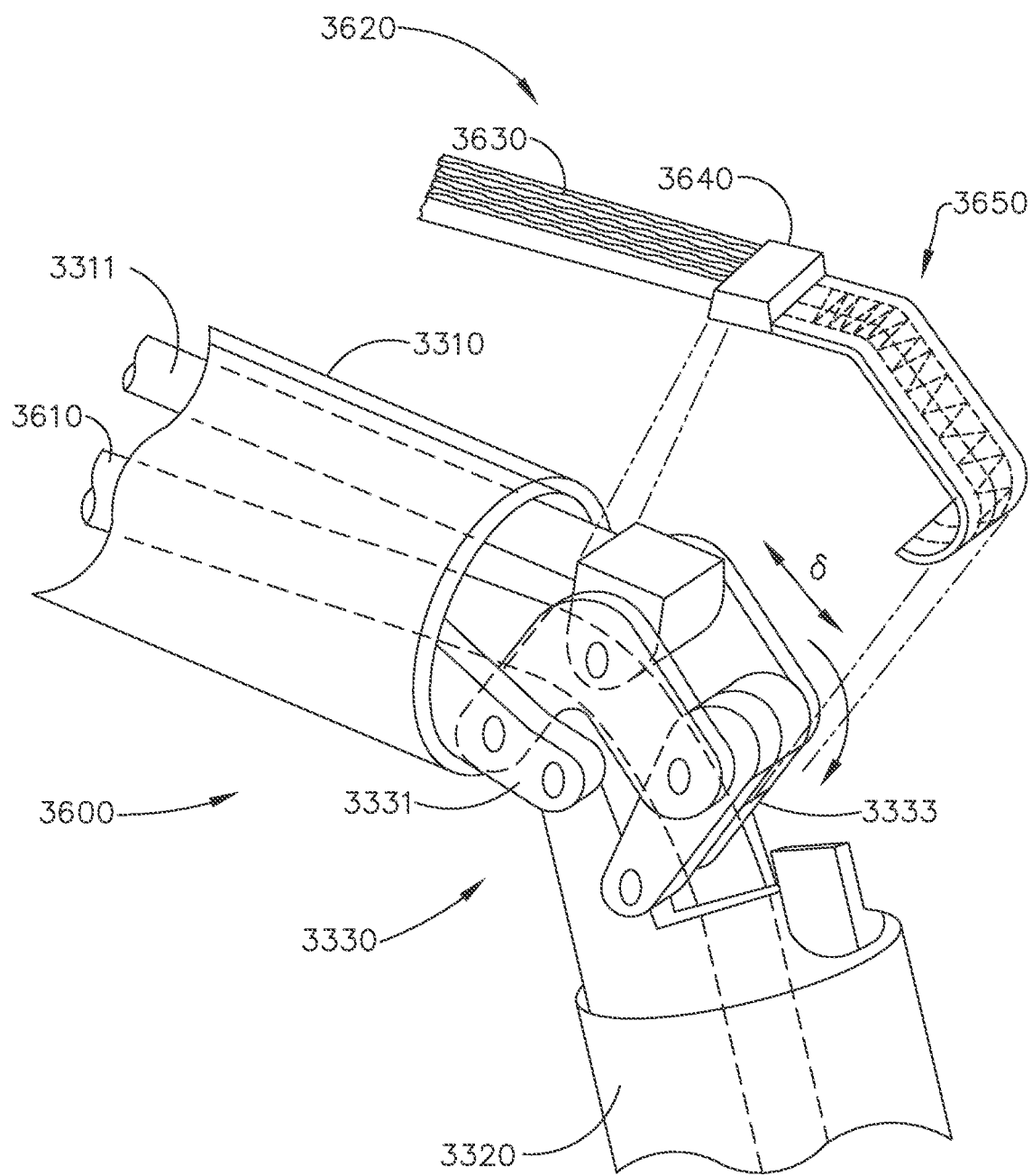
FIG. 46 is a perspective view of a surgical instrument assembly, illustrated with components removed, comprising a shaft, an end effector attached to the shaft by way of an articulation joint, and a sensing system comprising a stretchable sensing fabric and a flex circuit.
Figure 47:
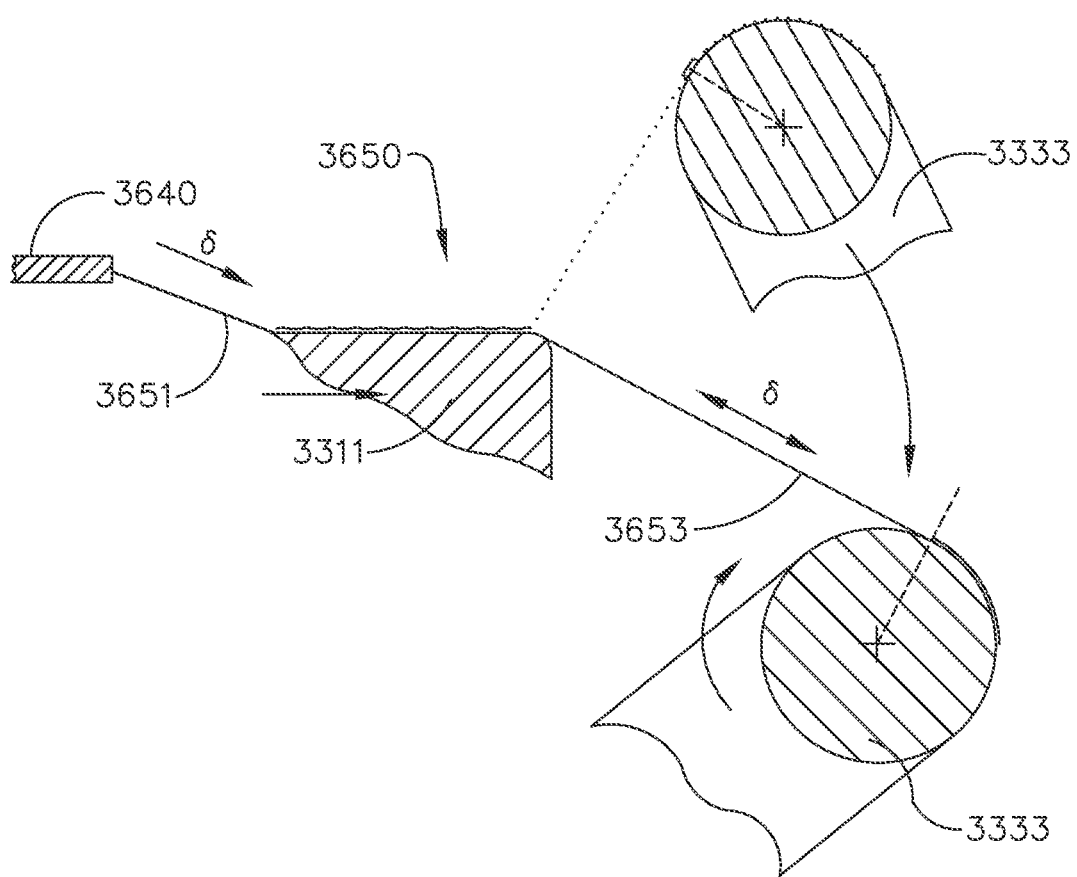
FIG. 47 is a cross-sectional view of components of the surgical instrument assembly of FIG. 46.

FIGS. 46 and 47 depict a surgical instrument assembly 3600 comprising the shaft 3310, end effector 3320, and articulation joint 3330 of FIGS. 38-40 and a sensing system 3620 configured to detect a parameter of the articulation actuator 3311. The surgical instrument assembly 3600 further comprises a firing actuator 3610 comprising a flexible member configured to extend through the articulation joint 3330 and into the end effector 3320 to actuate a function of the end effector 3320 such as closing the end effector 3320 and/or performing a staple firing stroke, for example.

The sensing system 3620 comprises a flex circuit 3630, a non-stretchable printed circuit board 3640 coupled to the flex circuit 3630, and a stretchable sensing fabric 3650 coupled to the printed circuit board 3640. The flex circuit 3630 extends through the shaft 3310 and can be connected to a surgical control interface such as a handle and/or a surgical robot, for example. The printed circuit board 3640 is attached to the articulation actuator 3311 and moves with the articulation actuator 3311. In certain instances, the printed circuit board 3640 is attached to a fixed location such as the shaft 3310, for example. The stretchable sensing fabric 3650 comprises electrical circuits which are connected to electrical contacts on the printed circuit board 3640 and, likewise, the flex circuit 3630 comprises electrical circuits which are connected to another set of contacts on the printed circuit board 3640. As a result, signals can be transmitted between the sensing fabric 3650, the printed circuit board 3640, the flex circuit 3630, and the surgical control interface.

The stretchable sensing fabric 3650 is configured to stretch as the end effector 3320 is articulated by the articulation actuator 3311. More specifically, a distal end of the stretchable fabric 3650 is attached the second articulation link 3333 such that as the end effector 3320 is articulated, the stretchable sensing fabric 3650 stretches. As the stretchable sensing fabric 3650 changes shape when it stretches, the conductive fibers within the stretchable sensing fabric 3650 also change shape and generate a change in resistance, for example. This change in resistance of the conductive fibers within the stretchable sensing fabric 3650 can be detected by a control circuit to determine a parameter, such as the orientation and/or position, of the articulation actuator 3311, articulation joint 3320, and/or end effector 3320. In various instances, the control circuit is in the printed circuit board 3640 and/or the surgical control interface.

In at least one instance, the stretchable sensing fabric 3650 is used to determine the exact position of the articulation actuator based on pre-determined known stretch characteristics of the stretchable sensing fabric 3650. In at least one instance, the stretchable sensing fabric 3650 is used to determine the degree of articulation of the end effector 3320 relative to the shaft 3310. In at least one instance, the stretchable sensing fabric 3650 is used to determine the speed and/or acceleration of the articulation actuator 3311. In at least one instance, the stretchable sensing fabric 3650 is used to directly measure one or more rotational characteristics of the articulation link 3333 such as, rotational velocity and/or rotational displacement, for example.

FIG. 47 depicts the sensing system 3620 where the non-stretchable printed circuit board 3640 is fixed relative to the shaft 3310. The stretchable sensing fabric 3650 comprises a first stretchable portion 3651 and a second stretchable portion 3653. In at least one instance, a portion of the stretchable sensing fabric 3650 is fixed to the articulation actuator 3311 in between the first stretchable portion 3651 and the second stretchable portion 3653. In such an instance, multiple regions of stretching can be sensed and can each be used to determine one or more parameters of the surgical instrument assembly 3600. As can be seen in FIG. 47, multiple positions of the second articulation link 3333 are illustrated showing different stretch lengths of the second stretchable portion 3653 when in each position. These different lengths can comprise different corresponding resistance profiles of conductive fibers within the stretchable sensing fabric 3650. These different corresponding resistance profiles can be assessed by a control circuit as described herein. The control circuit can then determine one or more parameters such as the degree of rotation, and/or end effector position, for example, based on the resistance profile detected.

Figure 48:
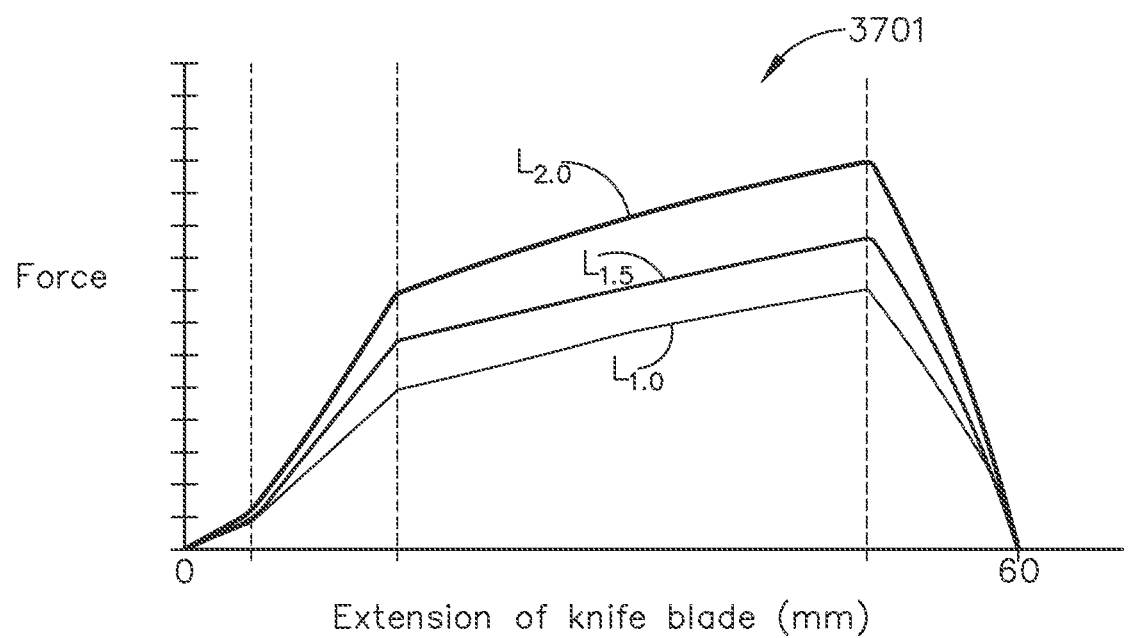
FIG. 48 is a graph illustrating three different possible load profiles defining a range of acceptable load profiles of an actuation member of a surgical instrument assembly.
Figure 49:
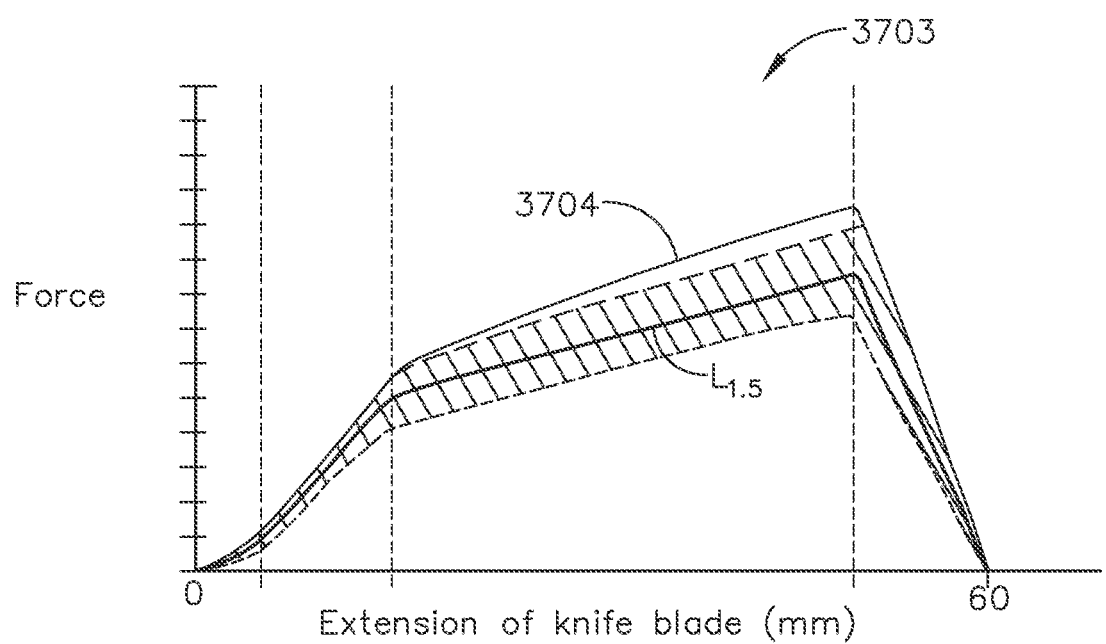
FIG. 49 is a graph illustrating an actual load profile of an actuation member compared to the range of acceptable load profiles defined in the graph of FIG. 48.

FIGS. 48 and 49 depict graphs 3701, 3703 in connection with a control circuit for use with a surgical instrument assembly configured to determine a load profile and adjust an operational control program of the surgical instrument assembly based on the determined load profile. The graph 3701 illustrates multiple different load profiles within a tissue cutting knife that, in at least one instance, define an acceptable range of loads for the tissue cutting knife. By way of another example, the acceptable range of load profiles is illustrated in the graph 3703 relative to an actual load profile 3704 detected by the control circuit using any suitable sensing system such as those disclosed herein. As can be seen in the example of FIG. 49, the actual load profile 3704 detected is above the range of acceptable load profiles. The control circuit can then take action accordingly. In at least one instance, the control circuit is configured to automatically adjust a control program of the surgical instrument assembly to reduce the load profile such as slow down a drive member and/or pause the actuation of the drive member, for example. In certain instances, the control circuit is configured to reduce the maximum current available to the electric motor to reduce the load profile. In certain instances, the control system can modify the time, or pause, between operational steps when a discrepancy is detected. In at least one instance, the control system can increase the pause between clamping the end effector and performing a staple firing stroke, for example. In at least one instance, the control circuit is configured to alert a user that the load profile is outside of the acceptable range and request input from a user how to proceed. In at least one instance, the control circuit is configured to lock out the staple firing drive system upon detecting a load profile outside the range of acceptable load profiles. In such instances, other drive systems can be operated to retract the staple firing drive, open the end effector, and/or straighten the end effector, for example.

In at least one instance, the control circuit is configured to determine a tissue thickness within an end effector and define the range of acceptable load profiles based on the determined tissue thickness. If a measured load profile is outside the defined range of acceptable load profiles, a user may be alerted that an irregularity has occurred during an actuation stroke. For example, a foreign object, such as a surgical clip, for example, may be present within the end effector causing the load profile to exceed the defined range of acceptable load profiles based on the determined tissue thickness.

In at least one instance, load profiles are monitored over time and adjustments can be made and/or recommended, for example, by a control circuit based on multiple actuations of the surgical instrument assembly. The control circuit may determine a steadily increasing load profile during each subsequent actuation of the surgical instrument assembly and may alert a user of the increasing load profiles. In at least one such instance, multiple load profiles must be measured and evaluated prior to action being taken by a control circuit.

In at least one instance, the force required to drive an end effector function with a worn component may increase over time. In such an instance, a user may be directed to swap out the surgical instrument assembly for a different one based on the detected wear. In at least one instance, the control circuit is configured to adjust a motor control program to compensate for the worn component to use up any remaining life of the worn component. For example, once a certain threshold of wear is detected, a control circuit can use a pre-determined use profile to determine that the surgical instrument assembly may be actuated a maximum of five more times before locking the surgical instrument assembly, for example, out and/or taking another action.

Further to the above, the load profiles of a surgical stapling assembly can be measured and monitored over time, i.e., throughout the life of the surgical stapling assembly. In various instances, a surgical stapling attachment assembly is configured to use replaceable staple cartridges and, after each firing of a replaceable staple cartridge, a load profile can be logged into the memory of the surgical instrument control system. In at least instance, adjustments to the operational characteristics of the surgical stapling attachment assembly can be made for each subsequent replaceable staple cartridge installed within the surgical stapling attachment assembly. In at least one instance, a control circuit can determine batch-specific load characteristics of a batch of staple cartridges. In such an instance, a batch-specific control program can be created and implemented by the control circuit based on the load profiles measured when using staple cartridges from the batch of staple cartridges. In at least one instance, a control circuit is configured to utilize manufacturing data communicated to the control circuit by the staple cartridge itself using an RFID chip, for example. In such an instance, the control circuit can log each event with matching manufacturing data in a grouping of firings to determine a suitable control program for staple cartridges with matching manufacturing data. Matching manufacturing data may include, for example, the same serial number, similar serial numbers, and/or serial numbers within a range of serial numbers, for example.

In various instances, a surgical instrument comprises a shaft, an end effector, and one or more drive systems configured to actuate the shaft and/or the end effector. The end effector comprises a first jaw and a second jaw which is rotatable relative to the first jaw between an open, unclamped position and a closed, clamped position. One of the drive systems comprises a jaw closure system configured to close the second jaw. The surgical instrument can further comprise an articulation joint rotatably connecting the end effector to the shaft and an articulation drive system configured to articulate the end effector relative to the shaft. The surgical instrument can also comprise a tissue cutting knife which is movable distally during a firing stroke and a knife drive system configured to drive the tissue cutting knife distally and retract the tissue cutting knife proximally. The surgical instrument further comprises a housing, such as a handle, for example, which rotatably supports the shaft such that the shaft is rotatable about a longitudinal axis relative to the housing. The surgical instrument can further comprise a drive system configured to rotate said shaft in clockwise and counter-clockwise directions about the longitudinal axis.

Each of the drive systems of the surgical instrument discussed above are driven by an electric motor. In various instances, each of the drive systems comprises its own electric motor which are separately and independently controlled by a controller, or control circuit. In other instances, at least two or more of the drive systems are driven by a single electric motor which is controlled by the controller. In such instances, the surgical instrument comprises a shifter, or transmission, which allows the electric motor to separately and independently drive different drive systems. In any event, the controller is responsive to user inputs, sensor inputs from within the surgical instrument, and/or sensor inputs external to the surgical instrument. In various instances, the controller comprises a control system including a processor and a memory device in the housing, a processor and a memory device in the shaft, and/or a wiring harness connecting and/or communicating with the various components of the control system, including the sensors, for example. In at least one instance, the control system comprises a flex circuit extending within the shaft that is in communication with a control system processor, such as a microprocessor, for example. The flex circuit can comprise a flexible substrate that is flexible enough to extend between the shaft and the end effector and accommodate the articulation of the end effector, discussed above, and electrical traces defined on and/or contained within the flexible substrate.

In at least one instance, further to the above, the flex circuit comprises a plurality of polyimide layers and metallic circuits positioned intermediate the polyimide layers. In at least one instance, the metallic circuits comprise copper frames while, in some instances, the metallic circuits are comprises of conductive ink, for example. Certain circuits within the flex circuit are wider, thicker, and/or have a higher conductivity than others and may be more suitable for conducting electrical power loads, whereas certain circuits that are narrower, thinner, and/or have a lower conductivity may be more suitable for conducting data communication signals, for example. In various instances, the power loads can create magnetic and/or electrical fields which can interfere with the data communication signals and, as a result, the power circuits can be separated and/or segregated from the communication circuits. In at least one instance, the power circuits are arranged in a power backbone within the flex circuit while the communication circuits are arranged in a communication backbone within the flex circuit. In various instances, the power backbone comprises a first segment within the flex circuit while the communication backbone comprises a second segment within the flex circuit. In at least one instance, the second, or communication segment, can be further sub-segmented. Whether or not a segment could be referred to as a sub-segment, they can be referred to as a segment and will be for the sake of convenience herein.

Figures 51, 52:
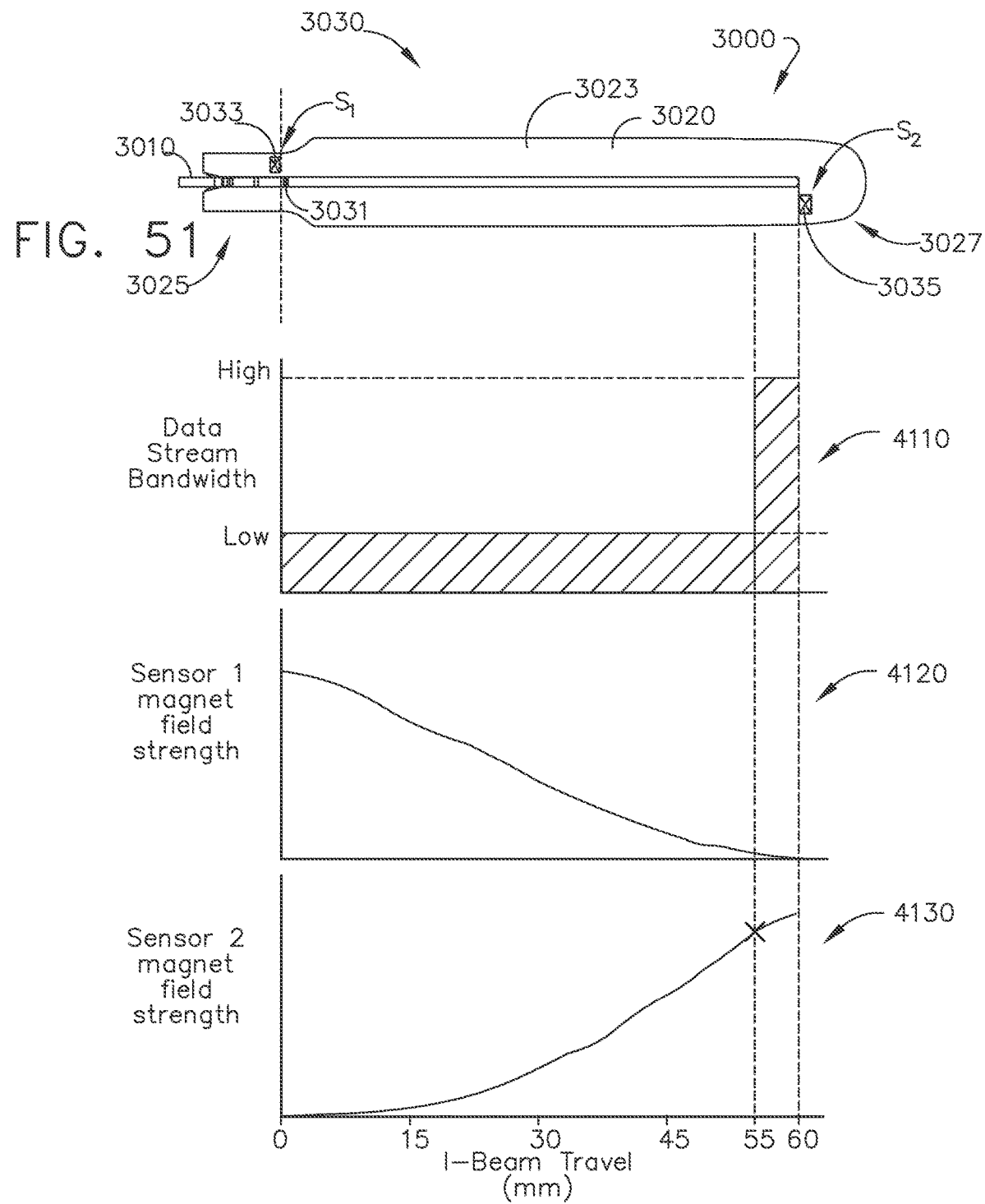
FIG. 51 is a plan view of the surgical instrument assembly of FIGS. 28-30.
FIG. 52 comprises multiple graphs depicting sensor readings and data stream bandwidth of the sensing system of the surgical instrument assembly of FIG. 51 relative to a firing stroke.

In various instances, further to the above, a flex circuit comprises a plurality of segments which are in communication with the controller. In at least one instance, the segments comprise sensor segments. For instance, a flex circuit can comprise a first segment including a first sensor, a second segment including a second sensor, and a third segment including a third sensor. The first sensor is configured to detect, at a first location, the status of a component of the surgical instrument, the second sensor is configured to detect, at a second location, the status of a component of the surgical instrument, and the third sensor is configured to detect, at a third location, the status of a component of the surgical instrument. That said, a flex circuit can comprise any suitable number of sensors and sensor circuit segments. In various instances, each sensor circuit segment is configured to evaluate the status of a different component while, in other instances, two or more sensor circuit segments can be used to evaluate the same component. Referring to FIGS. 51 and 52, a surgical instrument assembly 3000 comprises a staple cartridge 3020 and a firing member 3010 that is moved from a proximal end 3025 of the staple cartridge 3020 to a distal end 3027 of the staple cartridge 3020 during a firing stroke. In various instances, the firing member 3010 comprises one or more ramped surfaces configured to eject staples from the staple cartridge 3020 while, in some instances, the firing member 3010 comprises a tissue cutting edge. In any event, a magnet 3031 is mounted to the firing member 3010 which is tracked by a sensing system 3030 including a proximal sensor 3033 positioned at the proximal end 3025 of the staple cartridge and a distal sensor 3035 positioned at the distal end 3027. The magnet 3031 comprises any suitable magnetic element including one or more magnetic poles and can be comprised of iron and/or nickel, for example. The sensors 3033 and 3035 comprise Hall Effect sensors, for example, but could comprise any suitable type of sensor. Referring to graph 4120 in FIG. 52, the proximal sensor 3033 generates a magnetic field which is distorted or affected by the magnet 3031 when the firing member 3010 is in its proximal position. As the firing member 3010 is advanced distally during its firing stroke, the magnet 3031 moves away from the proximal sensor 3033 and, as a result, the effect that the magnet 3031 has on the magnetic field produced by the proximal sensor 3033 diminishes. This change in the magnetic field is detected by the controller which the controller interprets as the firing stroke being initiated. Similarly, referring to graph 4130 in FIG. 52, the magnet 3031 begins to distort and effect a magnetic field produced by the distal sensor 3035 as the firing member 3010 is moved distally during the firing stroke which is also detected by the controller which interprets this distortion as the firing stroke being completed.

The proximal sensor 3033 is part of a proximal sensor flex circuit segment and the distal sensor 3035 is part of a distal sensor flex circuit segment. The proximal sensor segment and the distal sensor segment are in communication with a control circuit defined on the flex circuit. In various instances, the control circuit comprises a microchip mounted to the flex circuit, for example. The proximal sensor 3033 is configured to provide or transmit data to the control circuit via the proximal sensor segment and the distal sensor 3035 is configured to provide or transmit data to the control circuit via the distal sensor circuit. Further to the above, in various instances, the proximal sensor 3033 produces and detects a magnetic field. The presence of the magnet 3031 distorts the magnetic field and the proximal sensor 3033 produces an analog signal, the voltage of which is proportional in magnitude with the detected magnetic field. The distal sensor 3035 works the same way. In such instances, as a result, the control circuit receives constant analog data streams from the proximal sensor 3033 and the distal sensor 3035. In various instances, the microchip of the control circuit can be configured to intermittently sample the data streams provided by the sensors 3033 and 3035. Alternatively, the proximal sensor 3033 and/or the distal sensor 3035 can comprise a digital Hall Effect sensor. In either event, the controller microchip can comprise an input dedicated to each sensor segment. In various instances, the control circuit can comprise a multiplexer, or MUX, that is configured to receive a plurality of data streams and merge the data streams into a signal output signal, for example. In any event, the control circuit utilizes the data received from the sensors to alter the operation of the surgical instrument, as described in greater detail below.

As discussed above, the surgical instrument comprises a proximal sensor circuit for detecting the movement of the firing member 3010 at the beginning of the staple firing stroke and a distal sensor circuit for detecting the movement of the firing member 3010 at the end of the staple firing stroke. In at least one embodiment, the control circuit actively monitors the proximal sensor circuit and distal sensor circuit throughout the staple firing stroke. Similarly, in at least one embodiment, the control circuit actively monitors the proximal sensor circuit and the distal sensor circuit throughout the retraction stroke of the firing member 3010. Thus, the control circuit requires an overall, or total, data bandwidth which can accommodate a first data bandwidth consumed by the proximal sensor segment and a second data bandwidth consumed by the distal sensor segment. Moreover, in such instances, the control circuit requires a power source sufficient to power the proximal sensor segment and the distal sensor segment at the same time. In various instances, however, it may be desirable for a larger portion of the total available bandwidth and/or power to be dedicated to one sensor segment than another at a given time. For instance, the control circuit can be configured to devote a larger data bandwidth and power to the proximal sensor segment than the distal sensor segment at the beginning of the staple firing stroke and, then, devote a larger data bandwidth and power to the distal sensor segment than the proximal sensor segment at the end of the staple firing stroke. In such instances, the control circuit can focus its sensing capacity to where the firing member 3010 is located. Such an arrangement can be highly suited for actively monitoring the initial acceleration of the firing member 3010 and the deceleration of the firing member 3010 at the end of the staple firing stroke. Stated another way, devoting an equal share of data bandwidth to the distal sensor segment at the initiation of the staple firing stroke is not an efficient use of the data bandwidth of the control circuit as the distal sensor segment does not monitor the firing member 3010 at the beginning of the staple firing stroke or the distal sensor segment is not as accurate as the proximal sensor segment in such instances. Similarly, devoting an equal share of data bandwidth to the proximal sensor segment at the end of the staple firing stroke is not an efficient use of the data bandwidth of the control circuit as the proximal sensor segment does not monitor the firing member 3010 at the end of the staple firing stroke or the proximal sensor segment is not as accurate as the distal sensor segment in such instances.

In various embodiments, the control circuit can be configured to selectively power and de-power the sensor segments of the flex circuit. In at least one such embodiment, the control circuit can apply a sufficient voltage to the proximal sensor segment to power the proximal Hall Effect sensor 3033 at the outset of the staple firing stroke such that the proximal sensor 3033 can sufficiently emit and detect its magnetic field, as discussed above, and, at the same time, not apply a sufficient voltage to the distal sensor segment to sufficiently power the distal Hall Effect sensor 3035. In such instances, the data bandwidth devoted to the distal sensor segment can be minimize or eliminated such that the control circuit can focus its bandwidth of the proximal sensor segment. Stated another way, the control circuit can place the distal sensor segment in a sleep mode at the beginning of the staple firing stroke. As the firing member 3010 is advanced distally, however, the control circuit can wake up the distal sensor segment by applying a sufficient voltage to the distal sensor segment and dedicate a sufficient portion of its data bandwidth to the distal sensor segment. Moreover, the control circuit can then place the proximal sensor segment in a sleep mode while the control circuit focuses its data bandwidth on the distal sensor segment. Such an arrangement can allow the control circuit to accurately brake, or slow down, the firing member 3010 at the proper time and/or stroke length, for example.

The teachings of the above-discussed examples could be used in any suitable systems in the surgical instrument. For instance, such an arrangement could be used in connection with articulation systems comprising a first sensor for detecting the articulation of the end effector in a first direction and a second sensor for detecting the articulation of the end effector in a second direction. Also, for instance, such an arrangement could be used in connection with the closure drive system. Moreover, such arrangements could be adapted for use with rotatable drive members.

In various embodiments, further to the above, the control circuit can be configured to intermittently ask the sensor segments to provide data. For instance, the sensors can be in a sleep mode in which they are not actively supplying voltage signals above a threshold, such as a noise threshold, to the control circuit until the control circuit selectively supplies a ping, or wake, signal to one or more of the sensor segments and, in such instances, the activated sensor segment, or segments, can supply a voltage signal to the control circuit above the noise threshold. In at least one embodiment, each sensor segment comprises a processor and a signal transmitter in communication with the sensor which are activated by an ask signal from the control circuit. In such embodiments, the each sensor segment is configured to provide at least some pre-processing of the data before it is transmitted to the control circuit. In at least one instance, the segment processor is configured to convert an analog signal to a digital signal and then transmit the digital signal to the control circuit. In various instances, the segment processor is configured to modulate the byte size of the data transmitted to the control circuit from the sensor segment. For instance, when the control circuit powers a sensor segment with a voltage magnitude within a first range, the sensor segment supplies data to the control circuit having a first byte size and, when the control circuit powers the sensor segment with a voltage magnitude within a second range that is different than the first range, the sensor segment suppliers data to the control circuit having a second byte size which is different than the first byte size. In at least one instance, the sensor segment processor supplies data with smaller byte sizes when the voltage magnitude is smaller and supplies data with larger byte sizes when the voltage magnitude is larger. In such instances, the sensor segment processor is configured to interpret the receipt of lower voltage magnitudes as an instruction to operate in a low-power/low-bandwidth mode and the receipt of higher voltage magnitudes as an instruction to operate in a high-power/high-bandwidth mode. Any suitable arrangement could be used.

In various embodiments, further to the above, the control circuit is configured to issue instructions to the sensor segments to provide data at a certain bandwidth. In at least one embodiment, the control circuit is configured to compare the total data bandwidth to the data bandwidth that is currently being consumed and issue instructions to the sensor segments to provide their data at bandwidths that will not overload, or exceed, the remaining available bandwidth. As more and/or less available data bandwidth is available, the control circuit can modify its instructions to the sensor segments. In at least one instance, each sensor segment comprises a signal receiver configured to receive a signal from the control circuit that includes data, or a plurality of instructions, for delivering the sensor data to the control circuit at the desired voltage magnitude, bandwidth, and/or byte size, for example. When the sensor segment receives a first set of instructions, the sensor segment delivers the sensor data in a first format and, when the sensor segment receives a second set of instructions, the sensor segment delivers the sensor data in a second format.

In various instances, further to the above, the control circuit can activate a sensor when a drive component has reached a specific position in its motion. For example, the control circuit can activate the distal sensor segment when the firing member 3010 reaches a position which is 5 mm from the end of the staple firing stroke. In at least one such instance, the distal sensor segment does not transmit data to the control circuit until the distal sensor segment is activated when the firing member 3010 reaches the 5 mm remaining position and, at such point, the distal sensor segment transmits data to the control circuit at a high bandwidth. To achieve this, the control circuit monitors the travel of the firing member 3010 during the firing stroke. In at least one instance, the control circuit uses the data from the proximal sensor segment to assess the position of the firing member 3010; however, the firing member 3010 is no longer adjacent the proximal sensor 3033 and the accuracy of the data from the proximal sensor 3033 may not be reliable enough to rely on. As such, the control circuit can comprise one or more sensor systems which can more measure the travel of the firing member 3010 more reliably. For instance, the control circuit can comprise a sensor system which monitors another drive component of the staple firing system such as the output shaft of the electric motor of the staple firing drive and/or a translatable shaft driven by the electric motor, for example. Various other arrangements are described in greater detail below.

In various embodiments, further to the above, a surgical instrument comprises a wiring harness, such as a flex circuit, for example, which comprises one or more integrated sensors that are positioned and arranged to measure the motion of a component locally, i.e., at a location adjacent to the component being monitored. In various instances, as discussed above, the component is rotatable. In at least one such instance, an array of magnetic elements are mounted, attached, and/or integrated to the rotatable component which produce magnetic fields that are detected by an array of coil sensors mounted in the shaft of the surgical instrument. The magnetic elements are arranged in a circular pattern and the coil sensors are arranged in a circular pattern that matches the circular pattern of the magnetic elements such that the magnetic fields produced by the coil sensors are affected by the magnetic fields produced by the magnetic elements. Each of the magnetic elements comprises at least one negative pole and at least one positive pole and the magnetic elements are arranged in an alternating manner such that the positive pole of a first magnetic element faces proximally and the adjacent magnetic elements are arranged such that the their negative poles are facing proximally, and so forth. Alternatively, the rotatable component comprises two magnetic elements mounted to a cylindrical body—a first magnetic element positioned on a first side of the cylindrical body and a second magnetic element positioned on a second, or opposite, side of the cylindrical body, i.e., the two magnetic elements are positioned 180 degrees apart. In this embodiment, the flex circuit comprises a coil sensor which is mounted to sequentially detect the first magnetic element and the second magnetic element in an alternating manner. The positive pole of the first magnetic element generally faces the coil sensor while the negative pole of the second magnetic element generally faces the coil sensor such that the sensing system has a resolution for each half rotation of the cylindrical body. A higher degree of resolution can be achieved with more magnetic elements and/or more coil sensors.

In various embodiments, further to the above, a surgical instrument comprises a wiring harness, such as a flex circuit, for example, which comprises one or more integrated sensors that are positioned and arranged to measure the motion of a component locally, i.e., at a location adjacent to the component being monitored. In various instances, as discussed above, the component is translatable. In at least one such instance, the flex circuit comprises a Hall Effect sensor and the translatable component comprises a magnetic element mounted thereto. During use, the translatable component is moved through a full range of motion between a first position and a second position. The Hall Effect sensor emits a magnetic field that is co-extensive with the full range of motion of the magnetic element such that the Hall Effect sensor can monitor the component throughout its entire range of motion.

In various embodiments, further to the above, the flex circuit comprises a first Hall effect sensor and a second Hall effect sensor and the translatable component comprises a first magnetic element and a second magnetic element. In at least one embodiment, the second Hall Effect sensor is positioned distally, or longitudinally, relative to the first Hall Effect sensor. Similarly, the second magnetic element is positioned distally, or longitudinally, relative to the first magnetic element. In use, the translatable component is moved distally from a proximal, unfired position to a distal, fired position during a firing stroke. During the initial motion of the translatable component, the first magnetic element is detectable by the first Hall Effect sensor but not the second Hall Effect sensor and, moreover, the second magnetic element is not detectable by either the first Hall Effect sensor or the second Hall Effect sensor. As the first magnetic element moves out of the range of the first Hall Effect sensor during the firing stroke, the second magnetic element moves into range of the second Hall Effect sensor. Notably, the first magnetic element does not enter into the range of the second Hall Effect sensor in this embodiment. As such, the entire range of motion of the translatable component can be monitored, collectively, by the first and second Hall Effect sensors. In at least one instance, there is a small amount of overlap during the firing stroke in which the first Hall Effect sensor can detect the first magnetic element and the second Hall Effect sensor can detect the second magnetic element. In other embodiments, there is no such overlap and the monitoring of the first and second Hall Effect sensors is line-to-line. The above-described arrangements would be useful to a low stroke actuation like an energy device or grasper/dissector (0.250" total stroke, for example) where the resolution of the stroke is highly correlated to a change in tissue clamp load for a small increment in stroke location change. The jaw actuator of a 5 mm grasper/dissector is typically between 0.1"-0.3" with +−0.05", for example, equating to several pounds difference in jaw tissue compression once closed onto tissue.

Figure 50:
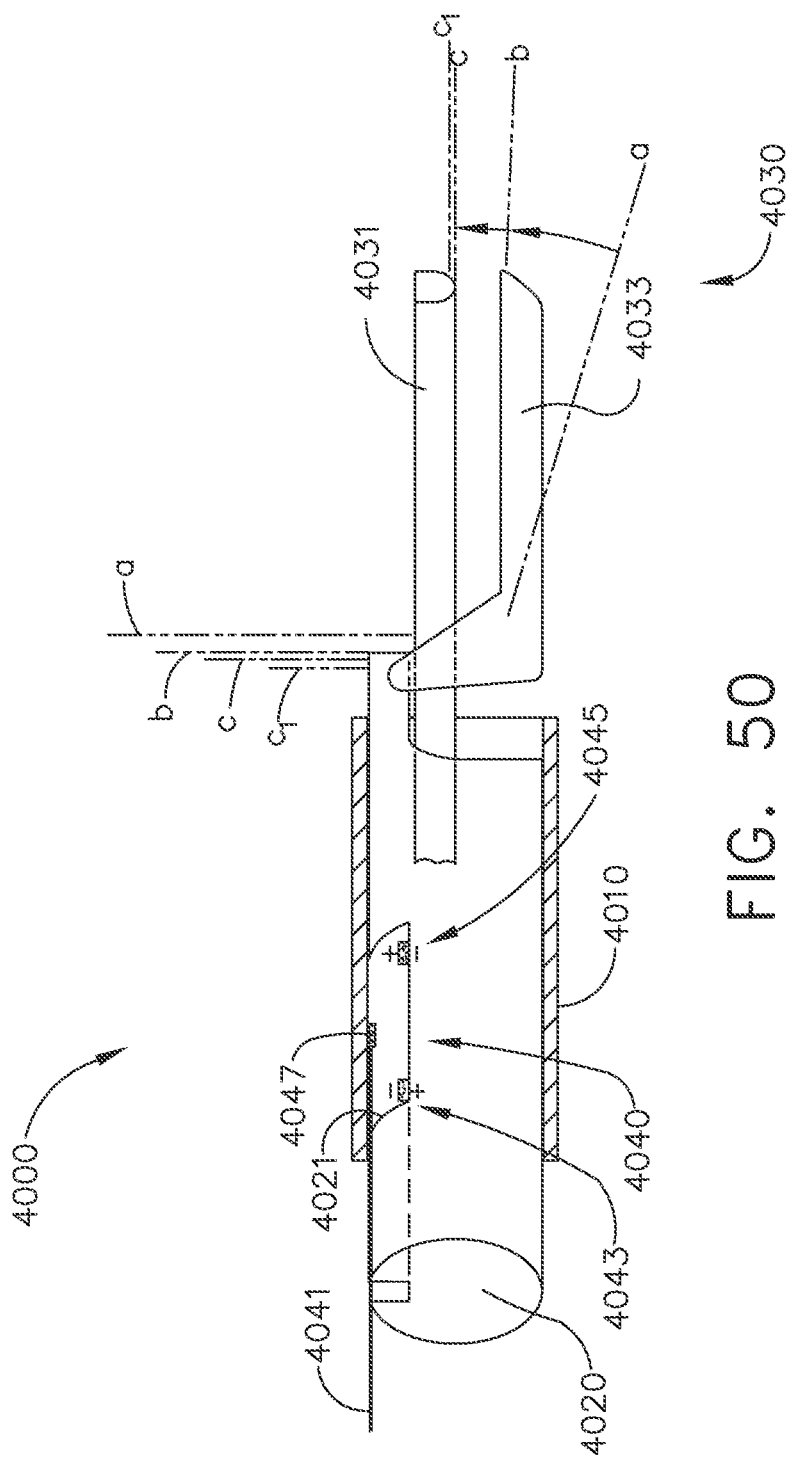
FIG. 50 is a partial cross-sectional view of a surgical instrument assembly, illustrated with components removed, comprising a sensing system configured to measure a parameter of the surgical instrument assembly.

A surgical instrument 4000 comprising a clamping jaw described above is illustrated in FIG. 50. The surgical instrument 4000 comprises a shaft 4010 and an end effector 4030. The end effector 4030 comprises a non-translating blade 4031 configured to apply vibratory energy to the tissue of a patient and, in addition, a clamp jaw 4033 rotatable between an open position and a closed position by a closure driver 4020. The clamp jaw 4033 is rotatably pinned to the shaft 4010 such that the clamp jaw 4033 rotates about a fixed axis and the closure driver 4020 is pinned to the clamp jaw 4033 such that, when the closure driver 4020 is pulled proximally, the closure driver 4020 rotates the clamp jaw 4033 toward the stationary jaw 4031. Correspondingly, the closure driver 4020 is moved distally to drive the clamp jaw 4033 toward its open position. The surgical instrument 4000 further comprises a sensing system 4040 configured to detect the movement of the closure driver 4020 and, thus, the movement of the clamp jaw 4033. The sensing system 4040 comprises a first, or proximal, magnetic element 4043 mounted to the closure driver 4020, a second, or distal, magnetic element 4045 mounted to the closure driver 4020, and a sensor 4047 mounted to the shaft 4010 configured to detect the motion of the magnetic elements 4043 and 4045. Notably, the first magnetic element 4043 comprises a negative pole which generally faces the sensor 4047 and the second magnetic element 4045 comprises a positive pole which generally faces the sensor 4047.

Further to the above, the sensing system 4040 comprises a controller in communication with the sensor 4047 configured to interpret the output of the sensor 4047 to assess the position of the closure driver 4020. Owing to the opposite polarities of the first magnetic element 4043 and the second magnetic element 4045, the motion of the closure driver 4020 has a high degree of resolution. In various instances, the sensor 4047 and the controller co-operate to detect the arrival and departure of the magnetic elements 4043 and 4045 within its magnetic field and, with this data, determine the orientation of the clamp jaw 4033. For a first given value of the sensor 4047 reading, the sensing system 4040 can determine that the clamp jaw 4033 is in a fully-open position (a). For a second given value of the sensor 4047 reading, the sensing system 4040 can determine that the clamp jaw 4033 is in a partially-closed position (b). For a third given value of the sensor 4047 reading, the sensing system 4040 can determine that the clamp jaw 4033 is in a closed position (c) in which the clamp jaw 4033 applies a low pressure to the tissue captured between the jaws 4031 and 4033, and for a fourth given value of the sensor 4047 reading, the sensing system 4040 can determine that the clamp jaw 4033 is applying a high pressure to the tissue in position (cp.

In various embodiments, a sensing system of a surgical instrument comprises a plurality of capacitive plates, such as a first capacitive plate and a second capacitive plate, for example. As a translatable component passes over the capacitive plates, the sensing system is able to detect capacitance changes in the capacitive plates in various instances, the first and second capacitive plates are arranged in parallel. In certain instances, the translatable component passes over the first capacitive plate and the second capacitive plate. With this information the control circuit is able to assess the position, speed, and/or direction of the translatable component.

In various embodiments, a sensing system of a surgical instrument comprises one or more optical sensors that are used to track the motion of a component. In at least one embodiment, the flex circuit comprises an optical sensor and the component comprises a light emitting diode, or other light source. When the component is advanced through its firing stroke, the intensity of light emitted from the LED changes as the LED approaches the optical sensor and/or as the LED moves away from the optical sensor. With the data from the optical sensor, the control circuit of the surgical instrument can determine the position, speed, and/or direction of the movable component. In various other embodiments, both the LED and the optical sensor can be mounted to flex circuit in the surgical instrument. In such embodiments, the movable components comprises through holes defined therein which, when aligned with the LED, allow the light emitted by the LED to be detected by the optical sensor. In at least one instance, the control circuit counts the pulses of light to assess the position, speed, and/or direction of the movable component. The control circuit is also able to assess partial pulses of light owing to partial alignment of an aperture with the LED and the optical sensor. In at least one instance, a partial obscurement of the light may be calculated to further refine the detection of the position of the movable member.

In various instances, robotic surgical systems are configured to be used with many different surgical instrument attachments. In such instances, the different surgical instrument attachments can each comprise sensing systems comprising sensors and corresponding triggers and actuators configured to be sensed by the sensing systems. In at least one instance, triggers of a first surgical attachment may interfere with sensor readings of a second surgical attachment. For example, the first surgical attachment and the second surgical attachment may each comprise a sensing system including a Hall Effect sensor and/or a magnetic system which can effect or interfere with one another. When the surgical instrument attachments come in proximity to each other to an extent where the magnet of the first surgical instrument attachments interferes with the Hall Effect sensor of the second surgical instrument attachment, for example, the control system can utilize an interference resolution system to properly operate the surgical instrument attachments, as described below.

Further to the above, a control circuit is provided to determine when Hall Effect sensor readings of the attached surgical instrument attachment are caused and/or affected by a magnet or magnetic source external to the intended trigger of the attached surgical instrument attachment. In at least one instance, a range of Hall Effect sensor values can be stored in a memory and correspond to expected values of the attached surgical instrument attachment. Should the control circuit see any values outside the specified range, the control circuit would then conclude that the sensing system within the attached surgical instrument attachment is being interfered with. In at least one instance, if signals are being received by the control circuit that do not correspond to an expected signal based on a monitored parameter of a motor driving an actuator of the attached surgical instrument attachment, the control circuit would then conclude that the sensing system within the attached surgical instrument attachment is being interfered with. Also, for example, if the Hall Effect sensor signal is fluctuating and a motor encoder monitoring movement of the motor is detecting no motor movement, then the control circuit would conclude that the sensing system of the attached surgical instrument attachment is being interfered with.

In at least one instance, sensors are provided within the shaft of a modular attachment to specifically sense external interference. For example, a Hall Effect sensor may be provided within the shaft of the attached surgical instrument attachment to sense external magnets that may be positioned in surgical instruments in close proximity to the attached surgical instrument attachment. A control circuit can monitor the Hall Effect sensor to determine if a nearby surgical instrument attachment comprising a magnet is in close proximity to the attached surgical instrument attachment.

In at least one instance, the control circuit is configured to take action within the surgical system if outside interference is detected. In at least one instance, the control circuit is configured to disable the sensing system local to the attached surgical instrument attachment so that any interference with the sensing system does not affect the operation of the attached surgical instrument attachment. In at least one instance, the control circuit is configured to ignore the interference based on its magnitude. For example, the interference may be below a certain threshold that may not affect the local sensing system. In such an instance, the local sensing system is used and the control circuit continues to monitor for possible increases in interference. In at least one instance, if the interference is determined to be a constant magnitude, the expected range of the sensors in the sensing system can be adjusted to compensate for the constant magnitude interference thereby allowing the local sensing system to continue to be used. In at least one instance, a constant magnitude of interference can be subtractively eliminated such that the constant magnitude of interference does not affect the local sensing system.

In at least one instance, a plurality of sensors are configured to be used to detect outside interference. In such an instance, the location of the interference can be determined by triangulating the interference signals. In such an instance, the interference can be identified and removed by a user and/or the surgical robot.

In at least one instance, multiple sensing systems within the attached surgical instrument attachment can be configured to trigger and sensor each other. Such local interference can be predictable and utilized as an asset in sensing one or more parameters of one or more actuators within the attached surgical instrument attachment. For example, a surgical stapling attachment comprises an actuator configured to clamp an end effector as well as eject staples from the end effector. In such an instance, one sensing system comprising a magnet and a Hall Effect sensor is positioned within the closure stroke and a second sensing system comprising a magnet and a Hall Effect sensor is positioned within the firing stroke. In such a system, the Hall Effect sensor within the closure stroke may be affected by the magnet of the sensing system. This overlap can be predictable and can provide more accurate detection of a parameter of the actuator during both the closure stroke and the firing stroke.

In at least one instance, sensors of a sensing system local to an attached surgical instrument attachment affected by outside interference can be temporarily switched to another sensing system if the parameter sensed by the sensing system is important for proper operation of the attached surgical instrument attachment. For example, if the Hall Effect sensor of a sensing system is effected by outside interference, a control circuit may switch to a different monitoring sensing system already equipped within the surgical instrument attachment. In at least one such instance, the control system can shift from monitoring a position sensor in the shaft to a motor position sensor.

In at least one instance, outside interference to a local sensing system may not be able to be adjusted or compensated for. In such an instance, action may be taken by a control circuit. In at least one instance, an alert may be sent to the robotic surgical system and/or the user. In at least one instance, the surgical instrument attachment may be locked out such that, until the local sensing system re-assumes an operable state, the surgical instrument attachment is locked out by the control circuit. In at least one instance, the control circuit can place the surgical instrument attachment into a limp mode activating a low-power actuation state, for example. When the control system determines that it is being interfered with, in various instances, the control system can slow the speed of the drive system, reduce the acceleration of the drive system, and/or reduce the maximum current that can be drawn by the electric motor, for example. In certain instances, the control system can modify the time, or pause, between operational steps when a discrepancy is detected. In at least one instance, the control system can increase the pause between clamping the end effector and performing a staple firing stroke, for example.

Figure 53:
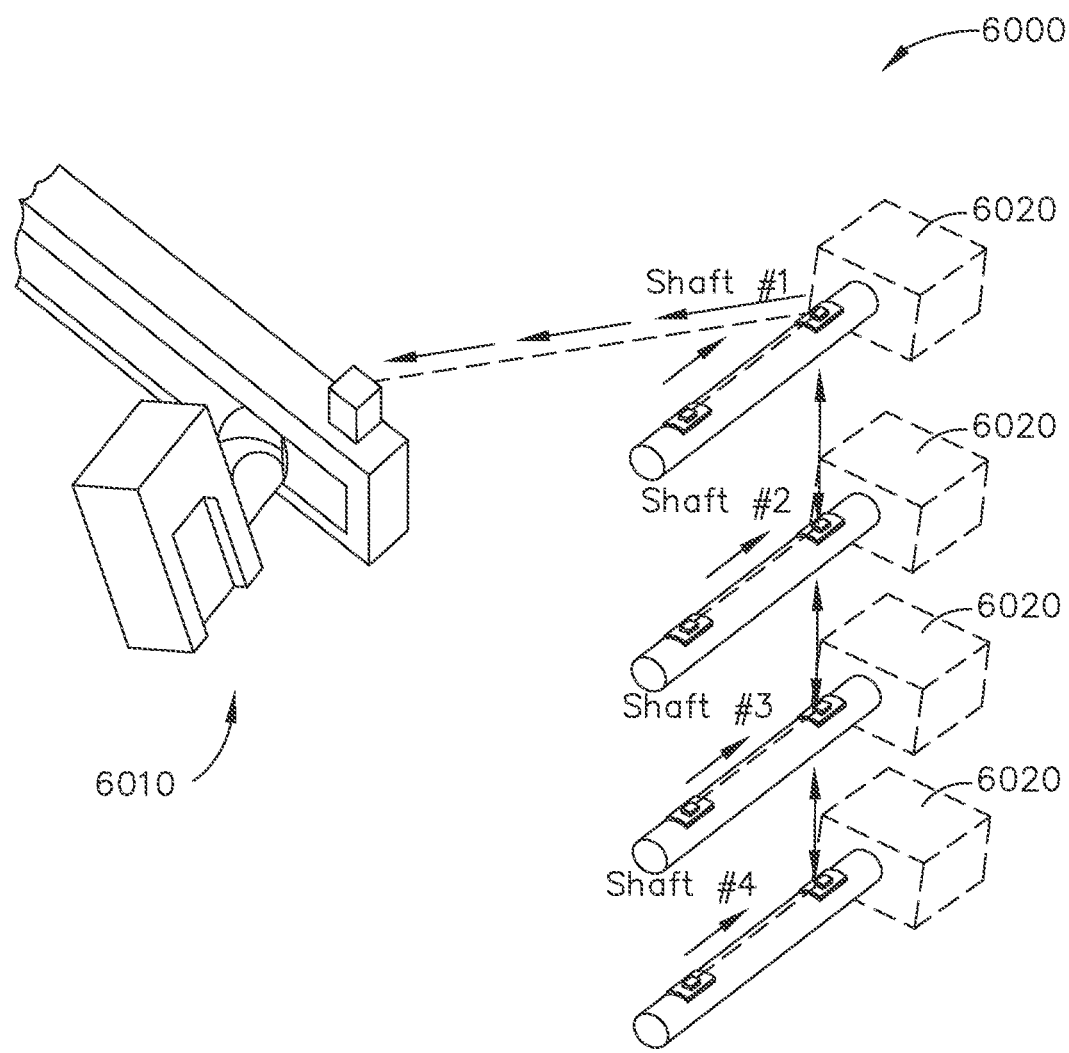
FIG. 53 is a perspective view of a surgical system comprising a surgical instrument attachment interface and a plurality of surgical instrument attachments.

FIG. 53 depicts a surgical instrument system 6000 comprising a robotic surgical interface 6010 and a plurality of surgical instrument attachments 6020 configured to be attached to the robotic surgical interface. The surgical instrument system 6000 comprises a wireless communication network. The surgical instrument attachments 6020 are configured to communicate with each other prior to any of the surgical instrument attachments 6020 being attached to the robotic surgical interface 6010. The surgical instrument attachments 6020 can communicate the status of each attachment 6020, for example, to each other indicating which surgical instrument attachment 6020 is ready to be attached to the robotic surgical interface 6010. Such information may be provided by the attachment itself and its current state and/or may be provided by a hub based on which attachment has already been indicated by the hub to be attached to the robotic surgical interface 6010. In at least one instance, color coded lights can be used on the surgical instrument attachments to indicate various things. For example, the attachments 6020 can communicate each other's status such that the attachments 6020 can identify and direct which attachment 6020 is to be attached to the robotic surgical interface 6010 for a given surgical procedure.

In various instances, the attachments 6020 can communicate with one another to communicate their proximity to one another. In such instances, a first attachment 6020 can communicate its proximity to a second attachment 6020 such that, if the first attachment 6020 detects interference with one or more of its sensors, the second attachment 6020 can understand the source of interference. In at least one such instance, the second attachment 6020 can communicate with the first attachment 6020 and request that the first attachment 6020 depower and/or otherwise modify its systems to reduce or eliminate the magnetic fields being generated by the first attachment 6020. Moreover, the second attachment 6020 can communicate with the robotic surgical system and/or the user to move the first attachment 6020.

In various instances, surgical instrument assemblies are manipulated by a user and/or a surgical robot such that the surgical instrument assemblies are placed into a variety of orientations that may affect the operation of the surgical instrument assembly. For example, access to certain areas of a target site within a patient may be difficult to reach which may result in a surgeon rotating the entire surgical instrument assembly into an upside down configuration. In such instances, certain operational systems of the surgical instrument assembly may be affected by such an orientation inversion. With this in mind, various surgical instrument assembles are configured to account for such effects. In at least one instance, a surgical instrument assembly can comprise an orientation-detection system configured to detect the orientation of a surgical instrument assembly and a control circuit configured to adjust an operational control program of the surgical instrument assembly based on the detected orientation of the surgical instrument assembly.

FIGS. 54 and 55 depict a handheld surgical instrument assembly 5000 and a user 5010 holding the handheld surgical instrument assembly 5000 in two different orientations. The surgical instrument assembly 5000 comprises a handle housing 5020 comprising a grip portion 5030 configured to be held by a user 5010 during use and a shaft assembly 5040 extending distally from the handle housing 5020. The shaft assembly 5040 comprises an end effector configured to treat tissue of a patient. Any suitable end effector can be used such as, for example, a surgical stapling end effector and/or an energy-based surgical end effector. The handle housing 5020 further comprises a trigger 5031 configured to actuate the function of the end effector of the shaft assembly 5040.

The surgical instrument assembly 5000 further comprises an orientation-detection system configured to detect the orientation of the surgical instrument assembly 5000. Such an orientation-detection system may comprise a gyroscopic sensor, for example. In at least one instance, such an orientation-detection system utilizes a camera and/or radar technology to determine the orientation of the surgical instrument assembly. FIG. 54 depicts the surgical instrument assembly 5000 in an upright orientation and the user 5010 holding the handle housing 5020 in a standard configuration where the index finger of the user 5010 is configured to pull the trigger 5031. The orientation-detection system is configured to detect that the surgical instrument assembly 5000 is in the upright orientation and communicate this information to a control circuit. Various embodiments are envisioned which detect the orientation of the handle 5020 relative to gravity. In such instances, the control system can determine that the handle 5020 is in a normal orientation when the grip 5030 is extending vertically downwardly or essentially vertically downwardly and in an upside-down orientation when the grip 5030 is extending vertically upwardly or essentially vertically upwardly. That said, the shaft of the surgical instrument assembly 5000 is rotatable relative to the handle 5020 in various instances and the orientation-detection system can be configured to determine the relative rotation between the shaft and the handle 5020. In such instances, the control system can be configured to alter the control program in some way when the control system determines that the handle 5020 has been rotated upside-down, or essentially upside-down, relative to the shaft.

The control circuit is configured to adjust an operational control program of the surgical instrument assembly 5000 based on the detected upright orientation. In at least one instance, the trigger 5031 comprises an adjustable component configured to vary the force required to squeeze the trigger 5031 to activate a function of the end effector. In at least one instance, a standard force 5050 is required to squeeze the trigger 5031 to activate the function of the end effector when the surgical instrument assembly 5000 is detected to be in the upright orientation. Turning now to FIG. 55, the surgical instrument assembly 5000 is in an inverted orientation. In the inverted orientation, a user 5010 may be holding the grip portion 5030 in an awkward configuration which may make it more difficult to apply enough force 5060 to squeeze the trigger 5031 to activate a function of the end effector. In such an instance, the control circuit is configured to reduce the force required to squeeze the trigger 5031 to activate the function of the end effector. The control circuit is configured to adjust an operational control program of the surgical instrument assembly 5000 based on ergonomics of the surgical instrument assembly 5000 during operation and/or based on varied finger and/or wrist strength during use of the surgical instrument assembly 5000. In at least one instance, an inverted orientation may reduce operational capabilities of a drive system because of the weight of the drive system, for example. In such an instance, an adjustment can be made to a motor control program to restore the reduced operational capabilities of the drive train to full operational capacity based on the inverted orientation. In various instances, the control system can reduce the speed of the drive member being actuated, reduce the acceleration, reduce the maximum force, and/or reduce the maximum current that can be drawn by the electric motor driving the drive member, for example, when the control system determines that the handle is in an inverted orientation. In certain instances, the control system can modify the time, or pause, between operational steps when a particular orientation is detected. In at least one instance, the control system can increase the pause between clamping the end effector and performing a staple firing stroke, for example.

In at least one instance, a control circuit is configured to control a force threshold required to activate and deactivate a trigger of a surgical instrument assembly. This can allow a user to activate and/or deactivate the trigger with non-dominate fingers and/or while the hand of the user is in a non-dominate configuration, for example.

In various instances, further to the above, the orientation of surgical stapling end effectors can be detected and a control circuit can adjust an operational control program of the surgical stapling end effector based on the detected orientation. FIGS. 56 and 57 depict an end effector assembly 5100 comprising a shaft 5110 and an end effector 5120 extending distally from the shaft 5110. The end effector 5120 comprises a cartridge jaw 5130 and an anvil jaw 5140 movable relative to the cartridge jaw 5130. While the anvil jaw 5140 is movable in this embodiment, embodiments are also contemplated where the cartridge jaw 5130 is movable in addition to, or in lieu of, the anvil jaw 5140. The end effector assembly 5100 further comprises an orientation-detection system comprising a gyroscope, for example, configured to detect the orientation of the end effector assembly 5100 relative to gravity.

In at least one instance, the position of the anvil jaw 5140 is detectable and can be used to determine the orientation of the end effector assembly 5100. For example, slop can be purposefully incorporated in the anvil closure drive train to ensure that the anvil jaw 5140 falls down into an upright unclamped position (FIG. 57) and falls down into an inverted unclamped position (FIG. 56) which is different than the upright unclamped position. In such an instance, the distance between the anvil jaw 5140 and the cartridge jaw 5130 would be different in both orientations; however, the anvil jaw 5140 and the cartridge jaw 5130 would both be in a fully unclamped configuration. The position of the anvil jaw 5140 can then be detected to determine the orientation of the end effector assembly 5100.

In at least one instance, a motor is used to rotate the end effector assembly 5100 about an end effector axis causing the inversion of the end effector assembly 5100. In such an instance, an encoder may be employed on the motor to determine the orientation of the end effector assembly 5100.

In at least one instance, the anvil jaw 5140 may require a greater force to be applied thereto to be opened when the end effector assembly 5100 is in the upright orientation (FIG. 57) as compared to the force required to open the anvil jaw 5140 when the end effector assembly 5100 is in the inverted orientation (FIG. 56). This may be due to gravity tending to pull the anvil jaw 5140 open relative to the cartridge jaw 5130 when the end effector assembly 5100 is in the inverted orientation. When the end effector assembly 5100 is in the upright orientation, gravity will tend to pull the anvil jaw 5140 closed relative to the cartridge jaw 5130. In any event, a control circuit is configured to detect the orientation of the end effector assembly 5100 and make adjustments to an operational control program based on the force needed to open and/or close the anvil jaw 5140 and/or other parameters disclosed herein.

In at least one instance, the control circuit is configured to automatically adjust the position of the anvil jaw 5140 to compensate for any gravity-based position variance of the anvil jaw 5140 as the end effector assembly 5100 is moved between various orientations. For example, if the anvil jaw 5140 comprises different positions relative to the cartridge jaw 5130 when the end effector assembly 5100 is in different orientations, the control circuit is configured to move the anvil jaw 5140 into a pre-defined unclamped position that matches the unclamped position regardless of the end effector orientation. In such an instance, the control circuit is configured to eliminate differences in the unclamped configuration of the anvil jaw 5140 as a result of the orientation of the end effector assembly 5100. In at least one instance, the control circuit is configured to increase force applied to the anvil jaw 5140 when the end effector assembly 5100 is in the upright orientation at least because the anvil jaw 5140 may require more force to be opened due to gravity working against opening of the anvil jaw 5140. In at least one instance, the control circuit is configured to decrease force applied to the anvil jaw 5140 when the end effector assembly 5100 is in the inverted orientation at least because the anvil jaw 5140 may require less force to be opened due to gravity assisting opening of the anvil jaw 5140.

FIGS. 58-61 depict a surgical instrument assembly 5200 comprising an attachment interface 5210, a shaft assembly 5240 attachable to and detachable from the attachment interface 5210 by way of a shaft attachment adapter 5220, and a sensing system 5230 configured to detect the orientation of the shaft assembly 5240 relative to the attachment interface 5210. The attachment interface 5210 may comprise any suitable attachment interface such as, for example, a surgical robot and/or a handheld surgical housing. The attachment interface 5210 comprises electrical contacts 5211 configured to electrically couple contacts 5221 of the shaft attachment adapter 5220 with the attachment interface 5210.

The shaft assembly 5240 comprises a shaft 5250 and an electrical attachment mechanism 5260 positioned on a proximal end of the shaft assembly 5240. The electrical attachment mechanism 5260 comprises electrical contacts 5261 and electrical leads 5263 extending distally from the electrical contacts 5261. The shaft assembly 5240 comprises at least one electrical system downstream of the electrical attachment mechanism 5260 with which the electrical contacts 5261 are coupled. The shaft assembly 5240 is configured to be physically and electrically coupled with the shaft attachment adapter 5220 by the electrical attachment mechanism 5260 and the sensing system 5230 comprises a slip ring assembly which places the shaft assembly 5240 in communication with the attachment adapter 5220.

The sensing system 5230 is configured to determine the orientation of the shaft assembly 5240 relative to the attachment interface 5210. The sensing system 5230 comprises an outer slip ring 5231, an intermediate slip ring 5233, and an inner slip ring 5235. The contacts 5261 are configured to be electrically coupled with the attachment interface 5210 through the slip rings 5231, 5233, 5235. The slip rings 5231, 5233, 5235 each comprise a discontinuity therein. The outer slip ring 5231 comprises an outer discontinuity 5232, the intermediate ring 5233 comprises an intermediate discontinuity 5234, and the inner slip ring 5235 comprises an inner discontinuity 5236. The discontinuities 5232, 5234, 5236 are used to determine the orientation of the end shaft assembly 5240 as the shaft assembly 5240 is rotated relative to the shaft attachment adapter 5220. When the shaft assembly 5240 is rotated, the contacts 5261 pass over the discontinuities 5232, 5234, 5236.

In at least one instance, the discontinuities 5232, 5234, 5236 comprise high resistance regions that are detectable within the electrical circuit. As the contacts 5261 pass over the discontinuities 5232, 5234, 5236, high resistance can be detected. A control circuit is configured to keep track of how many times and in what order the contacts 5261 pass over the high resistance regions as the shaft assembly 5240 is rotated relative to the shaft attachment adapter 5230. The control circuit is configured to determine what orientation the shaft assembly 5140 is in relative to the shaft attachment adapter 5220 based on the number of times the contacts 5261 pass over the discontinuities 5232, 5234, 5236.

FIG. 59 depicts the shaft assembly 5240 in an upright orientation. As the shaft assembly 5240 is rotated counterclockwise into the orientation illustrated in FIG. 60, a control circuit can determine that the contacts 5261 passed over the outer discontinuity 5232 based on a high resistance detection, for example, within a circuit including the outer slip ring 5231. Because the outer discontinuity 5232 was passed over first, as opposed to the other discontinuities 5234 and 5236, the control circuit can determine which direction the shaft assembly 5240 was rotated. As can be seen in FIG. 60, the shaft assembly 5240 has been rotated counterclockwise into an inverted orientation from the orientation illustrated in FIG. 59. Rotating into this position will cause the intermediate discontinuity 5234 to be passed over. As a result, the control circuit can determine that the shaft assembly 5240 is inverted based on the fact that the outer discontinuity 5232 was first detected and then the intermediate discontinuity 5234 was detected.

In at least one instance, slip rings of surgical instrument assemblies comprise high conductivity regions as well as low conductivity regions. In such an instance, the control circuit is configured to determine when the shaft assembly has rotated to and settled on a low conductivity region. This may be disadvantageous when trying to preserve the electrical communication between the attachment interface and any electric system within the shaft assembly. In such an instance, the control circuit is configured to adjust an operational control program which controls the rotation of the shaft assembly relative to the attachment interface to which the shaft assembly is attached. In at least one instance, the operational control program is adjusted so that the shaft assembly is rotated out of the low conductive regions and immediately into the nearest high conductivity region. In at least one instance, a user is alerted of the low conductivity relationship between the shaft assembly and the attachment interface. In such an instance, the user can adjust the shaft assembly manually and/or ignore the alert regarding the detected low conductivity relationship.

In at least one instance, a control circuit is configured to log conductivity issues of different components and the areas in which there are conductivity problems. In at least one instance, a component can be locked out after a certain threshold of low conductivity regions has been detected. In such an instance, if the component is ever re-attached within a surgical instrument system, the control circuit can alert a user of the situation and/or lock out the component from being used.

In at least one instance, such an orientation-detection system can be used with an energy-based surgical device. In such an instance, a control circuit is configured to limit generator power delivered through the components when a low conductivity relationship is present. In at least one instance, the electrical circuits are used for sensing systems. In such instances, the control circuit is configured to ignore signals transmitted when a low conductivity relationship is present.

Figure 62:
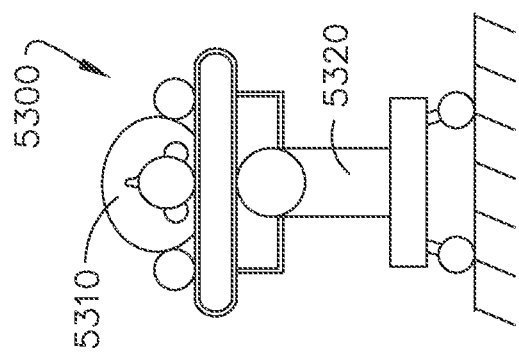
FIG. 62 is an elevational view of an operating table and patient, wherein the operating table an patient are oriented in a first orientation.
Figure 63:
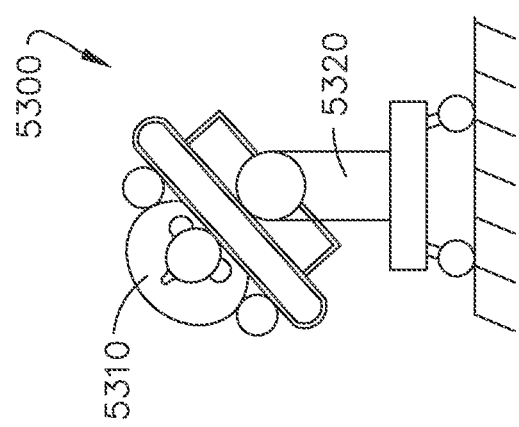
FIG. 63 is an elevational view of the operating table and patient of FIG. 62, wherein the operating table an patient are oriented in a second orientation.
Figure 64:
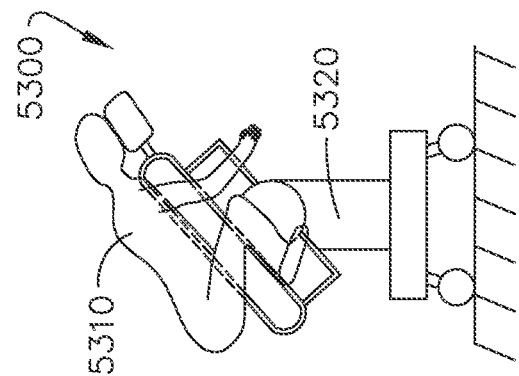
FIG. 64 is an elevational view of the operating table and patient of FIG. 62, wherein the operating table an patient are oriented in a third orientation.

In various instances, a control circuit is provided to adjust an operational control program of a surgical instrument assembly and/or robot, for example, based on a detected orientation of a patient. FIGS. 62-64 depict a surgical instrument system 5300 comprising a patient 5310 and an operating table 5320 on which the patient 5310 is positioned for surgery. The surgical instrument system 5300 further comprises an orientation-detection system such as a gyroscopic sensor, for example, configured to detect the orientation of the patient. A control circuit is provided to adjust operational control parameters of surgical instrument assemblies and systems used during surgery based on the detected orientation of the patient. In at least one instance, adjustments are made such that positional limits are placed on where robotic arms can move relative to the patient based on the patient's detected orientation. For example, if the patient is in the orientation depicted in FIG. 62, the control circuit may limit movement of robotic arms such that the robotic arms do not move below the patient where the robotic arms may not be useful and/or harm the patient.

In various instances, a surgical hub is used within a surgical environment. The surgical hub is configured to communicate with one or more modules within the surgical environment. The modules may comprise shaft assemblies, end effectors, surgical instrument handles, surgical robots, operating tables, and/or robotic control interfaces, for example. The surgical hub may be connected to a cloud-based system. The surgical hub is configured to communicate with the modules to determine various characteristics of the modules. The surgical hub is also configured to control operational capabilities of each module.

Figure 65:
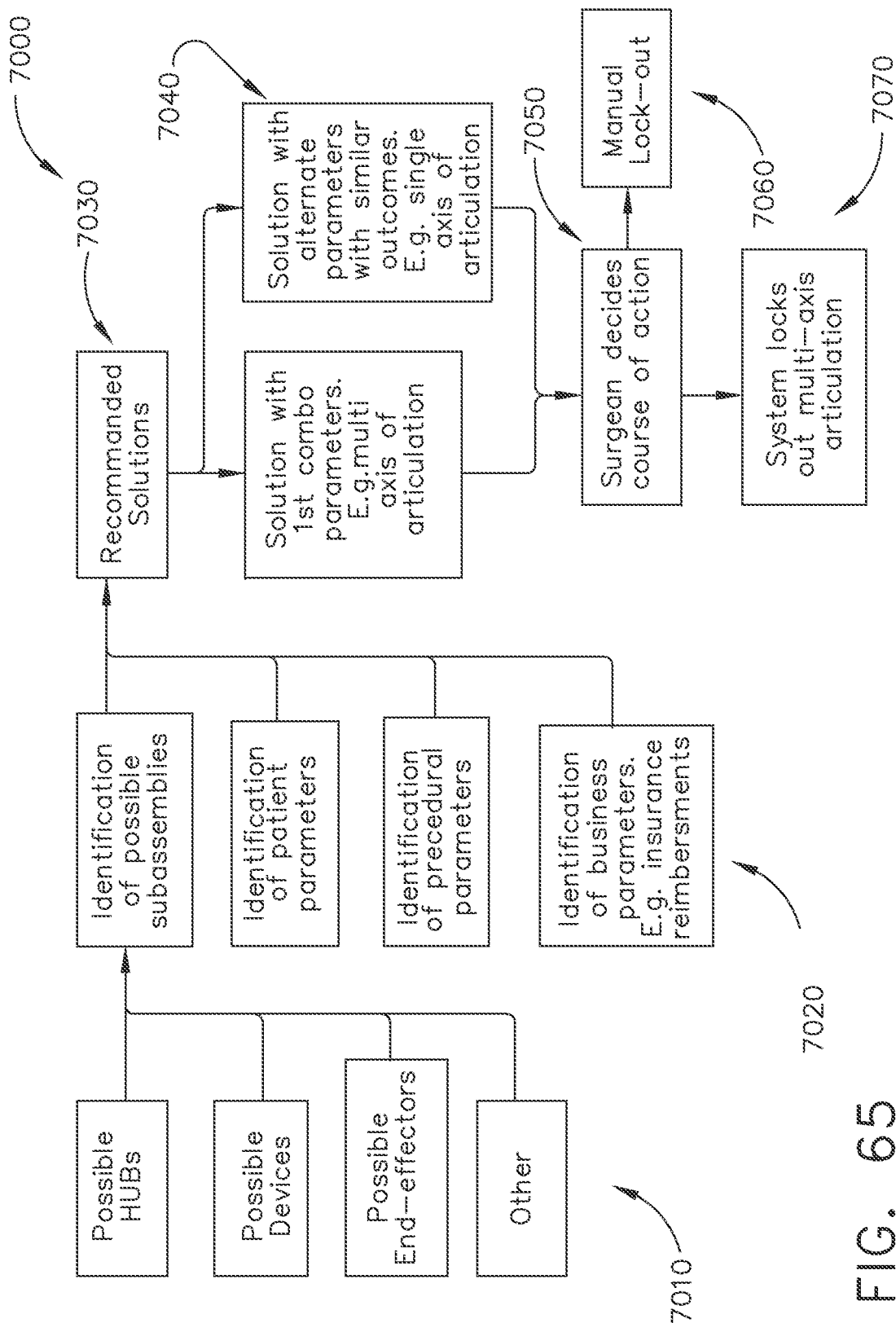
FIG. 65 is a flow chart depicting a surgical instrument control circuit.

FIG. 65 is a flow chart 7000 depicting a surgical instrument control circuit for use in an environment with modular surgical instrument components and/or a surgical hub. The control circuit is configured to receive a plurality of hardware inputs 7010 comprising information about modular surgical instrument components and/or the surgical hub. The inputs may comprise capability information of each module, for example. The control circuit is also configured to identify various parameters 7020 of the surgical environment. The various parameters 7020 comprise identification of possible component assembly combinations, identification of patient data corresponding to the intended surgery, for example, identification of procedural parameters, and identification of business parameters. In at least one instance, the control circuit is further configured to consider what surgeon is executing the surgery, what operating room the surgery is taking place, and/or what hospital the surgery is taking. All such inputs and parameters can affect how the modules and the surgical hub operate.

The control circuit is further configured to determine recommended solutions 7030 based on all of the inputs received by the control circuit. The recommended solutions 7030 may comprise optimal operational control programs for motors within various modules and/or sensing control programs configured optimize sensing capabilities of sensing systems within the modules. In at least one instance, the control circuit is configured to provide optional solutions 7040 to a user. The optional solutions 7040 comprise a first solution that comprises a control program that utilizes a multi-axis articulation system of a module. The optional solutions 7040 also comprises a second solution that comprises a control program that limits the multi-axis articulation system of the module to single-axis. In at least one instance, a user is configured to choose 7050 the desired solution. In at least one instance, a manual lockout 7060 is provided. In at least one instance, if the user chooses the optional solution 7040 utilizing single-axis articulation, then the control circuit is configured to lockout multi-axis articulation of the module.

In various instances, a control circuit is configured to identify all sub systems and/or components within a surgical hub environment. In at least one instance, modules configured to be used in the surgical hub environment each comprise means or wireless communicating with the surgical hub. In at least one instance, the control circuit is configured to identify each module within the surgical hub environment. In at least one instance, the control circuit is configured to define an operational control program for each module identified within the surgical hub environment.

In various instances, a control circuit is configured to identify all sub-systems within a surgical hub environment and automatically evaluate each identified sub-system. The evaluation may include running initialization programs to operate through all drive systems and/or sensing systems onboard each sub-system. In at least one instance, the control circuit is configured to connect each sub-system wirelessly to every other sub-system such that the sub-systems are able to communicate with each other. In at least one instance, the control circuit is configured to connect each sub-system to a surgical hub.

In at least one instance, a control circuit is configured actuate through each drive system of a combination of connected sub-systems. This actuation can be used to determine the capabilities of the combination of the connected sub-systems. In at least one instance, the control circuit is configured to adjust an operational control program based on feedback received during the initial actuation of the combination of connected sub-systems. In at least one instance, the control circuit is configured to compare the received feedback with information collected during previous uses of each sub-system. In such an instance, the control circuit can determine what portion of any operational variance is due to the combination of the connected sub-systems or is due to each sub-system itself. For example, a shaft assembly and an end effector assembly may be attached to each other forming a modular instrument assembly. The modular instrument assembly may then be attached to a handheld motorized attachment interface. The handheld motorized attachment interface may then automatically run through an initialization actuation phase to determine the available functions of the modular instrument assembly.

In various instances, a control circuit is configured to identify each module within a surgical hub environment and, based on the one or more identified modules, determine all possible combinations and/or sub-combinations of the identified modules. This may be determined by permissible pre-determined combinations. In at least one instance, a user can be displayed the various options of combinations available between all of the identified modules. In at least one instance, the control circuit is configured to recommend one or more module combinations based on the permissible pre-determined combinations and/or based on other inputs such as, for example, patient data and/or surgeon expertise level.

In various instances, a surgical instrument system comprises a remote server configured to aggregate different combinations of parts, tolerances, assembly modifications, and/or performance statistics from modules in the field. In at least one instance, a control circuit is configured to determine operational control parameters for any specific combination of modules. In at least one instance, the control circuit is configured to communicate the determined operational control parameters to all other modules. In at least one instance, the control circuit is configured to communicate the determined operational control parameters to other similar combinations of modules in the field. In at least one instance, the aggregation comprises a constantly evolving algorithm and, as more data and/or information is collected further defining the possible combinations, the control circuit can continuously iterate the possible combinations.

In at least one instance, the iteration process may comprise providing one possible solution to a first module system and a second possible solution to a second module system with similar variances and then use the outcomes of the first module system and the second module system to further refine the control parameters for the general population of modules. If an issue is identified with a specific combination is identified, the control circuit may notify a user of the issue. In at least one instance, the control circuit is configured to lockout the specific combination of modules when an issue with a specific combination of modules is detected. In at least one instance, a user may override the locked out combination and, with the understanding of what the identified issue is, the control circuit can unlock the module combination device. In such an instance, the control circuit is configured to more closely monitor usage data than would be monitored during normal use to allow for post-use diagnostics.

In at least one instance, calibration parameters are stored within each module onboard a local memory, for example. In at least one instance, other adjustment factors may be uploaded to the module itself such that the next time the module is connected to another module and/or the surgical hub, the other modules and/or the surgical hub can recognize the change in calibration parameters of the module. In various instances, the surgical hub is configured to utilize identification data received from each module such as, for example, serial numbers to look up viable control algorithms and/or operational parameters, for example for the specific module. In at least one embodiment, adjustment factors from two or more attached components are uploaded to the module and/or surgical hub. In such embodiments, the performance of the system can be co-operatively altered by two or more sets of adjustment parameter sets.

In at least one instance, a control circuit is configured to adjust a variety of control parameters such as, for example, a pause time between actuating various systems of a module, how long to wait before taking a measurement with an onboard sensing system of the module, minimum and maximum threshold limits related to motor speed and/or energy delivery, for example, stroke length of an actuation system of the module, actuation speeds of actuation systems of the module, initial actuation force of the module, rate of change trigger thresholds, and/or magnitude of rate of change adjustments. In at least one instance, control parameters are adjusted based on whether a cartridge with an adjunct pre-installed on the cartridge is present or a cartridge without an adjunct is present. In at least one instance, control parameters are adjusted based on the size of staples stored within the cartridge module that is installed.

Figure 66:
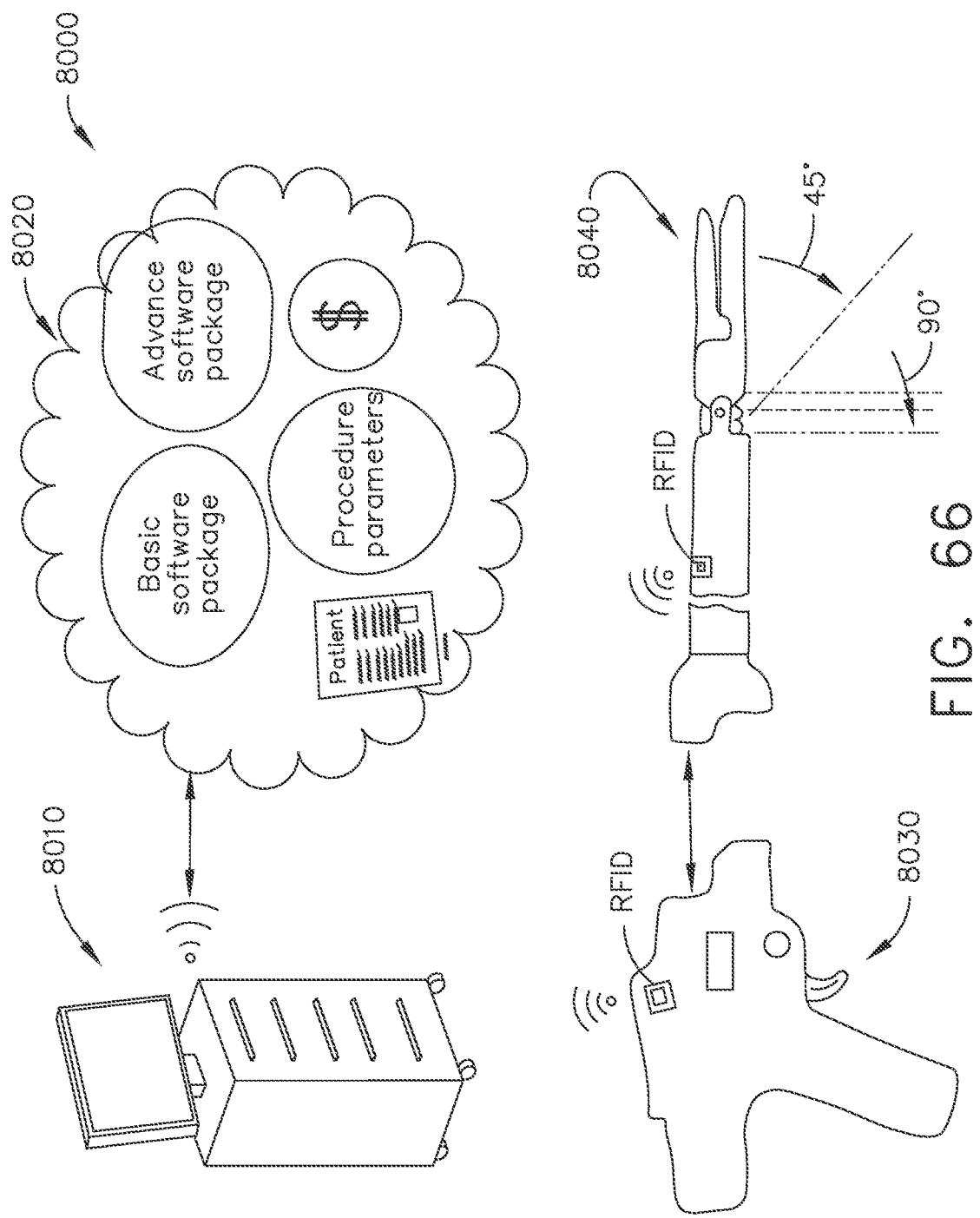
FIG. 66 is a schematic of a surgical instrument system comprising a hub and a plurality of modular instrument assemblies.

FIG. 66 is a schematic of a surgical instrument system 8000 comprising a surgical hub 8010, a data cloud 8020, a handheld actuation module 8030, and a shaft assembly module 8040. Each module 8030, 8040 comprises an RFID communication device configured to allow intercommunication between the modules 8030, 8040 and the surgical hub 8010. The data cloud 8020 is configured to store software program data, situational awareness data, and/or any suitable hub data therein. The surgical hub 8010 is configured to access the data cloud 8020 to determine if various modules being used require a reduced functionality for any given set of data in the data cloud 8020. In at least one instance, the shaft assembly module 8040 comprises a smart battery and/or a smart display.

In at least one instance, the operational capabilities of a module include a degree of end effector articulation of an end effector assembly, energy output levels of an energy-based surgical device, and/or speed of staple firing of a surgical stapling shaft assembly, for example. End effector articulation, for example, may be reduced to a range of 45 degrees left and 45 degrees right from a full articulation range of an end effector assembly which may be 90 degrees left and 90 degrees right, for example. Energy output levels, for example, may be reduced to lower power levels than what an energy-based surgical device is capable of delivering to a patient, for example. Speed of staple firing of a surgical stapling shaft assembly may be reduced to half speed, for example.

In various instances, a surgical hub is configured to identify a module within the surgical environment. In at least one instance, the surgical hub is configured to determine the capabilities of the module by interpreting a signal received from the module which may include data corresponding to the capabilities of the module. The surgical hub is configured to limit the capabilities of the module based on a pre-defined control program. The pre-defined control program may be defined by a level of software package purchased for the module. For example, there may exist three different levels of software. The levels may comprise, for example, beginner, intermediate, and/or advanced. If the beginner level of software is purchased, the capabilities of the module may be reduced to a beginner configuration. Such a configuration may include slowing the firing speed and/or reducing range of articulation, for example. If the intermediate level of software is purchased, the capabilities of the module may be increased from the beginner configuration to an intermediate configuration where the module is not able to run in at a full capabilities configuration but, rather, the intermediate configuration. Such a configuration may include providing the full range of articulation but maintaining the reduced firing speed. If the advanced level of software is purchased, the capabilities of the module may be at a maximum capability configuration where every feature is unlocked and able to be used and/or the module is able to run at the full capabilities configuration.

Such software level upgrades may be employed in a training environment where it may be safer to limit certain surgeons to a more beginner level of software. The surgical hub may track the surgeons while using the beginner level of software and determine when the surgeons are ready to advance to the next level. The surgical hub may alert a surgeon of an available upgrade in software level and/or automatically upgrade the module for that particular surgeon. Different surgeons may be differentiated by using login information within the surgical hub such that one more advanced surgeon may be able to use a module at a more advanced software level while the more advanced surgeon is logged in to the surgical hub and another more beginner surgeon may be limited to using that same module at a more beginner software level while the beginner surgeon is logged in to the surgical hub.

In at least one instance, the surgical hub is configured to enable features and/or full capabilities of a module on-the-fly. For example, an override feature may be provided such that a surgeon is able to override a system restricting the surgeon to certain capabilities.

In at least one instance, the surgical hub is configured to determine the appropriate level of shaft capabilities based on patient data accessible by the surgical hub from the cloud-based system. For example, a certain patient may not need high energy levels based on the type of tissue expected to be operated on. In such an instance, the surgical hub is configured to limit the energy delivery levels of an energy-based surgical instrument module for that patient's surgery. In at least one instance, available functionality of an energy-based surgical instrument module is defined and/or limited based on available power within a surgical suite. For example, a previous generation generator may be the only source of power for the energy-based surgical instrument module that may not be able to deliver enough power to maximize the potential of the energy-based surgical instrument module. In such an instance, the energy-based surgical instrument module is limited to a low-power configuration. In at least one instance, available power within the surgical suite may be limited and a surgical instrument generator, itself, may be placed into a low-power operational mode based on the availability of power within the surgical suite.

In at least one instance, capabilities of module configured to be enabled and/or limited may include sensing systems. If a surgeon is unfamiliar with how a more advanced and/or precise sensing system works within a particular module, for example, that sensing system may be entirely disabled for that surgeon. In at least one instance, the sensing system is placed into a training mode that allows a surgeon to learn how the sensing system works before the sensing system operates at a full capabilities level. In at least one instance, the sensing system is operated at a reduced state to simply the module for the surgeon.

In at least one instance, the surgical hub is configured to send a test, or initialization, signal to each module to determine each module's range of capabilities and limits. This may also be referred to as a module-interrogation stage, for example. In at least one instance, the surgical hub is also configured to determine any irregularities and/or worn systems, for example, within each module during the test program. In at least one instance, an initialization signal is sent to each module to be used during a surgery prior to the surgery commencing. In at least one instance, the initialization signal is sent to each module just before the module is used during the surgery. In at least one instance, the surgical hub is configured to alert a user if any of the modules need replaced based on detected irregularities, for example. Irregularities may be detected by onboard sensing systems of each module. During an initialization stage, an onboard motor, for example, is configured to actuate through all systems and test all actuation systems and/or sensing systems onboard a module. In modules without a motor, such initialization may occur once the module is attached to a motorized actuation system. In such an instance, the module may be locked out from regular use during the initialization stage.

In at least one instance, a motorized actuation module, such as a handheld attachment interface to which various shaft assemblies and/or end effectors may be attached, is used to limit capabilities of the various shaft assemblies and/or end effectors attached to the motorized actuation module. For example, a shaft assembly to be attached to the motorized actuation module may not comprise a communication means to communicate with the hub. In such an instance, a control program of the motorized actuation module is defined to limit and/or define the available functionality of the shaft assembly.

In at least one instance, module functionality may be defined based on how many times the module has been used. Such data can be kept within the module itself locally. In at least one instance, the surgical hub is configured to track how many times a particular module has been used. In at least one instance, module functionality may be defined by the age of the module. In at least one instance, module functionality may be defined by the age of a power source. In at least one instance, module functionality may be defined by events logged during previous uses of the module. In at least one instance, the events logged may include problematic uses where one or more systems within the module failed during use, for example. For example, during a first use, an articulation drive system of a surgical stapling end effector module may break. The surgical hub is configured to log this event. A surgeon may reattach the surgical stapling end effector module knowing that the articulation system is broken. The surgical hub may limit and/or lockout the use of the articulation drive system and permit the surgeon to use the clamping, stapling, and/or cutting functions only.

In various instances, modules and a surgical hub may comprise a level of intercommunication that is controllable based on cost and/or needs, for example. In at least one instance, various modules comprise capable communication array systems configured to communicate with the surgical hub and/or other modules with capable communication array systems. In at least one instance, the level of intercommunication between modules and/or the surgical hub may be reduced based on the purchased software. To unlock full intercommunication, an advanced communication software may have to be purchased.

A first tier intercommunication level could provide basic communication between each module and the hub. For example, with the first tier intercommunication level, each module may be able to transmit information to the surgical hub; however, with the first tier intercommunication level, the modules may not be able to communicate with each other nor would the surgical hub be able to send upgrade signals, for example, to the modules. A second tier intercommunication level could, in addition to the capabilities of the first tier intercommunication level, provide the surgical hub with the ability to send update signals to updateable modules. A third tier intercommunication level could provide full intercommunication between all capable modules and the surgical hub unlocking full access to software updates, module intercommunication, and/or logging device usage statistics, for example.

In at least one instance, upgrading system software of various modules can be advantageous as control programs are used multiple times after an initial roll out of a local module. The surgical hub can be configured to update operational algorithms of a local module based on usage of the module in multiple different hospitals, for example. All of the usage statistics of the uses of the module in the multiple different hospitals can be logged and used to update the operational algorithms of the module. Updating the software of the local module regularly can update the operational algorithm of the local module providing a safer and/or more effective operational algorithm for the local module.

In at least one instance, multiple different software programs exist within the surgical hub. A first software program is configured to contain all of the information corresponding to full functionality of a module such as a shaft assembly, for example. A second software program such as, an add on, for example, may be available which contains advanced modes such as, for example, a power limiting mode, a sleep mode, an increased core kernel processing mode which may allow a module to take more precise measurements, take more measurements, react faster, and/or operate faster and/or more efficiently, for example. In at least one instance, the different software programs are selectable by a user. In at least one instance, the cost paid for a module corresponds to which software program is available for that module. In at least one instance, software programs are readily updateable for a module. In at least one instance, the surgical hub is configured to recommend a software program based on situational awareness data within the hub.

Many of the surgical instrument systems described herein are motivated by an electric motor; however, the surgical instrument systems described herein can be motivated in any suitable manner. In various instances, the surgical instrument systems described herein can be motivated by a manually-operated trigger, for example. In certain instances, the motors disclosed herein may comprise a portion or portions of a robotically controlled system. Any of the systems disclosed herein can be used with a handled surgical instrument. Moreover, any of the systems disclosed herein can be utilized with a robotic surgical instrument system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail and is incorporated by reference herein in its entirety.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Various embodiments described herein are described in the context of linear end effectors and/or linear fastener cartridges. Such embodiments, and the teachings thereof, can be applied to non-linear end effectors and/or non-linear fastener cartridges, such as, for example, circular and/or contoured end effectors. For example, various end effectors, including non-linear end effectors, are disclosed in U.S. patent application Ser. No. 13/036,647, filed Feb. 28, 2011, entitled SURGICAL STAPLING INSTRUMENT, now U.S. Patent Application Publication No. 2011/0226837, now U.S. Pat. No. 8,561,870, which is hereby incorporated by reference in its entirety. Additionally, U.S. patent application Ser. No. 12/893,461, filed Sep. 29, 2012, entitled STAPLE CARTRIDGE, now U.S. Patent Application Publication No. 2012/0074198, is hereby incorporated by reference in its entirety. U.S. Patent Application Ser. No. 12/031,873, filed Feb. 15, 2008, entitled END EFFECTORS FOR A SURGICAL CUTTING AND STAPLING INSTRUMENT, now U.S. Pat. No. 7,980,443, is also hereby incorporated by reference in its entirety. U.S. Pat. No. 8,393,514, entitled SELECTIVELY ORIENTABLE IMPLANTABLE FASTENER CARTRIDGE, which issued on Mar. 12, 2013, is also hereby incorporated by reference in its entirety.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP).

The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

As discussed above, the surgical instruments disclosed herein may comprise control systems. Each of the control systems can comprise a circuit board having one or more processors and/or memory devices. Among other things, the control systems are configured to store sensor data, for example. They are also configured to store data which identifies the type of staple cartridge attached to a stapling instrument, for example. More specifically, the type of staple cartridge can be identified when attached to the stapling instrument by the sensors and the sensor data can be stored in the control system. This information can be obtained by the control system to assess whether or not the staple cartridge is suitable for use.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118, 241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein. The disclosures of International Patent Publication No. WO 2017/083125, entitled STAPLER WITH COMPOSITE CARDAN AND SCREW DRIVE, published May 18, 2017, International Patent Publication No. WO 2017/083126, entitled STAPLE PUSHER WITH LOST MOTION BETWEEN RAMPS, published May 18, 2017, International Patent Publication No. WO 2015/153642, entitled SURGICAL INSTRUMENT WITH SHIFTABLE TRANSMISSION, published Oct. 8, 2015, U.S. Patent Application Publication No. 2017/0265954, filed Mar. 17, 2017, entitled STAPLER WITH CABLE-DRIVEN ADVANCEABLE CLAMPING ELEMENT AND DUAL DISTAL PULLEYS, U.S. Patent Application Publication No. 2017/0265865, filed Feb. 15, 2017, entitled STAPLER WITH CABLE-DRIVEN ADVANCEABLE CLAMPING ELEMENT AND DISTAL PULLEY, and U.S. Patent Publication No. 2017/0290586, entitled STAPLING CARTRIDGE, filed on Mar. 29, 2017, are incorporated herein by reference in their entireties.

Example Set 1

Example 1—A surgical instrument system, comprising a surgical instrument assembly, comprising a shaft, an end effector attached to the shaft, and at least one drive component positioned with the shaft. The surgical instrument system further comprises a surgical control circuit comprising a motor control program configured to run a motor configured to drive at least one drive component positioned within the shaft. The surgical control circuit is configured to receive a first measurement of a parameter of the motor, and receive a second measurement of a parameter of at least one drive component, wherein the second measurement is sensed locally within the shaft. The surgical control circuit is further configured to compare the first measurement and the second measurement, determine an actual relationship of the first measurement and the second measurement based on the comparison, compare the actual relationship to an expected relationship, and adjust the motor control program based on the comparison of the actual relationship and the expected relationship to align the actual relationship with the expected relationship.

Example 2—The surgical instrument system of Example 1, wherein the parameter of the motor comprises a parameter of an output shaft attached to the motor.

Example 3—The surgical instrument system of Examples 1 or 2, wherein the expected relationship is learned by the surgical control circuit through the surgical instrument assembly.

Example 4—The surgical instrument system of Examples 1, 2, or 3, wherein the second measurement is provided by a linear motion-detecting sensor.

Example 5—The surgical instrument system of Examples 1, 2, 3, or 4, wherein the first measurement is provided by a rotary motion-detecting sensor.

Example 6—The surgical instrument system of Examples 1, 2, 3, 4, or 5, wherein the parameter of the motor comprises dynamic braking of the motor during an intermediate phase of a firing stroke.

Example 7—The surgical instrument system of Examples 1, 2, 3, 4, 5, or 6, wherein the parameter of the motor comprises dynamic acceleration of the motor during an initial phase of a firing stroke.

Example 8—The surgical instrument system of Examples 1, 2, 3, 4, 5, 6, or 7, wherein the adjustment of the motor control program comprises recalibrating the motor control program based on the actual relationship.

Example 9—A surgical instrument system, comprising a surgical instrument assembly, comprising a shaft, an end effector attached to the shaft, wherein the end effector comprises a first jaw movable relative to the second jaw, and a closure member configured to move the first jaw relative to the second jaw. The surgical instrument system further comprises a surgical control circuit comprising a motor control program configured to run a motor configured to actuate the closure member. The surgical control circuit is configured to determine when the motor rotates a first amount corresponding to a first expected displacement of the closure member with a motor encoder, determine an actual displacement of the closure member with a sensor positioned within the shaft, compare the actual displacement of the closure member and the first expected displacement of the closure member, determine an additional target displacement corresponding to a second expected displacement of the closure member; and recalibrate the motor control program to rotate the motor sufficient to drive the closure member the second expected displacement.

Example 10—A surgical instrument assembly, comprising a shaft, an end effector attached to the shaft, a firing member configured to move through the end effector during a firing stroke, and a stretchable optical waveguide attached to the shaft and the firing member, wherein the stretchable optical waveguide is configured to stretch as the firing member is moved through the firing stroke. The surgical instrument assembly further comprises a light sensor configured to sense a change in light presence within the stretchable optical waveguide during the firing stroke, and a control circuit configured to monitor signals received from the light sensor to determine at least one parameter of the firing member during the firing stroke.

Example 11—The surgical instrument assembly of Example 10, further comprising an articulation joint attaching the end effector to the shaft, wherein the stretchable optical waveguide is attached to the shaft proximal to the articulation joint.

Example 12—The surgical instrument assembly of Examples 10 or 11, wherein the stretchable optical waveguide comprises one or more vertical-cavity surface-emitting lasers and one or more photo diodes.

Example 13—The surgical instrument assembly of Example 12, wherein the photo diode is configured to measure a loss of light in the stretchable optical waveguide as the waveguide is stretched during the firing stroke.

Example 14—A surgical instrument assembly, comprising a shaft, an end effector attached to the shaft, and a firing member configured to move through the end effector during a firing stroke, wherein the firing member comprises a plurality of windows defined in the firing member. The surgical instrument assembly further comprises a light source, and a light sensor configured to detect the light source, wherein the plurality of windows are configured to pass between the light source and the light sensor as the firing member moves through the firing stroke. The surgical instrument assembly further comprises a control circuit configured to monitor signals received from the light sensor to determine at least one parameter of the firing member during the firing stroke.

Example 15—The surgical instrument assembly of Example 14, wherein the plurality of windows comprise a pattern corresponding to linear distance traveled by the firing member.

Example 16—A surgical instrument assembly, comprising a shaft, an end effector attached to the shaft, a firing member configured to move through the end effector during a firing stroke, and a sensing circuit comprising a stretchable resistive cable attached to the shaft and the firing member, wherein the stretchable resistive cable is configured to stretch as the firing member is moved through the firing stroke. The surgical instrument assembly further comprises a control circuit configured to monitor the resistance of the sensing circuit to determine at least one parameter of the firing member during the firing stroke.

Example 17—A surgical instrument system, comprising a surgical instrument assembly that comprises a shaft, an end effector attached to the shaft, and a firing member configured to move through the end effector during a firing stroke, wherein the firing member comprises a magnet. The surgical instrument system further comprises a first Hall effect sensor positioned at a beginning of the firing stroke, and a second Hall effect sensor positioned at an end of the firing stroke. The surgical instrument system further comprises a surgical control circuit, comprising a motor, and a control circuit comprising a motor control program. The control circuit is configured to monitor the rotation of the motor, compare the rotation of the motor to signals received from the first Hall effect sensor and the second Hall effect sensor, determine if the firing member has moved an expected distance based on the comparison of the rotation of the motor and the signals received from the first Hall effect sensor and the second Hall effect sensor, and recalibrate the motor control program if the firing member has not moved the expected distance. The surgical instrument system further comprises a sensing circuit comprising a stretchable resistive cable attached to the shaft and the firing member, wherein the stretchable resistive cable is configured to stretch as the firing member is moved through the firing stroke. The surgical instrument system further comprises a control circuit configured to monitor the resistance of the sensing circuit to determine at least one parameter of the firing member during the firing stroke.

Example 18—A surgical instrument, comprising a shaft, an end effector attached to the shaft, and a firing system comprising an electric motor and a firing member configured to move through the end effector during a firing stroke. The surgical instrument further comprises a stretchable optical waveguide attached to the shaft and the firing member, wherein the stretchable optical waveguide is configured to stretch as the firing member is moved through the firing stroke. The surgical instrument further comprises a light sensor configured to sense a change in light presence within the stretchable optical waveguide during the firing stroke, an encoder configured to evaluate the rotation of the electric motor, and a control circuit. The control circuit is configured to monitor signals received from the light sensor and the encoder to determine distortions in the firing member that cause the motion of the firing member to depart from an expected motion.

Example 19—The surgical instrument of Example 18, further comprising an articulation joint attaching the end effector to the shaft, wherein the stretchable optical waveguide is attached to the shaft proximal to the articulation joint, wherein the firing member extends through the articulation joint, and wherein the distortions in the firing member arise from the articulation of the end effector.

Example 20—A surgical instrument, comprising a shaft, an end effector attached to the shaft, a firing member configured to move through the end effector during a firing stroke, wherein the firing member comprises a plurality of windows defined in the firing member. The surgical instrument further comprises an electric motor configured to drive the firing member, a light source, and a light sensor configured to detect the light source, wherein the plurality of windows are configured to pass between the light source and the light sensor as the firing member moves through the firing stroke. The surgical instrument further comprises an encoder configured to evaluate the rotation of the electric motor, and a control circuit configured to monitor signals received from the light sensor and the encoder to determine distortions in the firing member that cause the motion of the firing member to depart from an expected motion.

Example 21—The surgical instrument of Example 20, further comprising an articulation joint attaching the end effector to the shaft, wherein the firing member extends through the articulation joint, and wherein the distortions in the firing member arise from the articulation of the end effector.

Example 22—A surgical instrument, comprising a shaft, an end effector attached to the shaft, and a firing member configured to move through the end effector during a firing stroke, wherein the firing member comprises a first band and a second band. The surgical instrument further comprises a sensing circuit comprising a first stretchable resistive cable attached to the shaft and the first band and a second stretchable resistive cable attached to the shaft and the second band, wherein the first stretchable resistive cable and the second stretchable resistive cable are configured to stretch as the firing member is moved through the firing stroke. The surgical instrument further comprises a control circuit configured to monitor the resistance of the sensing circuit to determine at least one parameter of the firing member during the firing stroke.

Example 23—The surgical instrument of Example 22, further comprising an articulation joint attaching the end effector to the shaft, wherein the firing member extends through the articulation joint, and wherein distortions in the firing member arise from the articulation of the end effector that are detectable by the control circuit.

Example Set 2

Example 1—A surgical instrument assembly, comprising a shaft, an articulation joint, and an end effector attached to the shaft by way of the articulation joint, wherein the end effector is configured to be articulated about the articulation joint. The surgical instrument assembly further comprises a flex circuit extending through the shaft and connected to the end effector, wherein the flex circuit comprises an articulation section aligned with the articulation joint. The articulation section comprises a predefined bend profile configured to stretch across the articulation joint predictably as the end effector is articulated about the articulation joint.

Example 2—The surgical instrument assembly of Example 1, wherein the articulation section comprises elastic connection members configured to bias the articulation section into the predefined bend profile.

Example 3—A surgical instrument assembly, comprising a shaft, an articulation joint, an end effector attached to the shaft by way of the articulation joint, and a flex circuit extending through the shaft. The flex circuit comprises a non-flexible zone, and a flexible zone extending across the articulation joint.

Example 4—The surgical instrument assembly of Example 3, wherein the flex circuit further comprises conductible flexible inks and conductible metallic traces.

Example 5—A surgical instrument assembly, comprising a shaft, an articulation joint, an end effector attached to the shaft by way of the articulation joint, and a flex circuit extending through the shaft. The flex circuit comprises a flexible section configured to be stretched in a predetermined direction. The flexible section comprises a relaxed state, a stretched state, and a plurality of elastic connection members attached to the flex circuit within the flexible section. The plurality of elastic connection members are configured to bias the flexible section into the relaxed state and permit the stretching of the flexible section in the predetermined direction.

Example 6—The surgical instrument assembly of Example 5, wherein the elastic connection members are oriented along the predetermined direction.

Example 7—A surgical instrument assembly, comprising a shaft, an end effector attached to the shaft, and a flex circuit extending through the shaft. The flex circuit comprises a flex circuit profile plane, and a pre-curved section where the flex circuit is bent such that the flex circuit profile plane is aligned in a single plane throughout the pre-curved section.

Example 8—The surgical instrument assembly of Example 7, further comprising an articulation joint, wherein the pre-curved section extends across the articulation joint, and wherein the pre-curved section is positioned off-center with respect to a central shaft axis defined by the shaft.

Example 9—A surgical instrument assembly, comprising a shaft, an end effector attached to the shaft, and a flex circuit extending through the shaft. The flex circuit comprises a flex circuit profile plane, and a pre-bent section where the flex circuit is bent such that the flex circuit profile plane is not aligned in a single plane throughout the pre-bent section.

Example 10—The surgical instrument assembly of Example 9, further comprising an articulation joint, wherein the pre-bent section extends across the articulation joint, and wherein the pre-bent section is positioned off-center with respect to a central shaft axis defined by the shaft.

Example 11—A surgical instrument assembly, comprising a shaft, an end effector, and a wiring harness extending through the shaft. The wiring harness comprises at least one first zone comprising a non-stretchable portion, and a second zone comprising a stretchable portion interconnecting the at least one first zone.

Example 12—The surgical instrument assembly of Example 11, wherein the first zone comprises a bendable portion.

Example 13—The surgical instrument assembly of Examples 11 or 12, wherein the stretchable portion comprises conductive ink.

Example 14—The surgical instrument assembly of Examples 11, 12, or 13, wherein the stretchable zone comprises metallic traces.

Example 15—The surgical instrument assembly of Examples 11, 12, 13, or 14, further comprising drive components positioned within the shaft, wherein the wiring harness is attached to at least one of the drive components in at least one location of the at least one of the drive components.

Example 16—The surgical instrument assembly of Example 15, wherein the at least one location comprises an index location, and wherein the index location defines a reference for at least one sensor of the wiring harness.

Example 17—The surgical instrument assembly of Example 16, wherein the at least one sensor is configured to monitor a parameter of the at least one of the drive components.

Example 18—A surgical instrument, comprising a shaft defining a longitudinal axis, an end effector, and an articulation joint, wherein the end effector is rotatably attached to the shaft about the articulation joint. The surgical instrument further comprises an articulation driver mounted to the end effector, wherein the articulation driver is translatable longitudinally to rotate the end effector about the articulation joint. The surgical instrument further comprises a wiring harness. The wiring harness comprises a shaft portion extending within the shaft, an end effector portion extending within the end effector, and an anchor portion mounted to the articulation driver. The wiring harness further comprises a first flexible bend extending between the shaft portion and the anchor portion, and a second flexible bend extending between the anchor portion and the end effector portion.

Example 19—The surgical instrument of Example 18, wherein the wiring harness comprises a first biasing member configured to return the first flexible bend to an unflexed state.

Example 20—The surgical instrument of Example 19, wherein the wiring harness comprises a second biasing member configured to return the second flexible band to an unflexed state.

Example 21—The surgical instrument of Examples 18, 19, or 20, wherein the wiring harness comprises a flex circuit comprised of polyimide layers.

Example 22—The surgical instrument of Example 21, wherein the wiring harness further comprises metallic electrical traces on the polyimide layers.

Example 23—The surgical instrument of Example 22, wherein the metallic electrical traces are comprised of metallic ink.

Example 24—The surgical instrument of Examples 18, 19, 20, 21, 22, or, 23, wherein the wiring harness further comprises silicone regions configured to permit the wiring harness to stretch.

Example 25—The surgical instrument of Example 24, wherein the metallic electrical traces extend over the silicone regions.

Example 26—The surgical instrument of Example 25, wherein the metallic electrical traces follow arcuate paths across the silicone regions.

Example 27—The surgical instrument of Examples 22, 23, 24, 25, or 26, wherein the metallic electrical traces are comprised of conductive ink.

Example 28—The surgical instrument of Examples 21, 22, 23, 24, 25, 26, or 27, wherein the wiring harness further comprises an aperture defined in the flex circuit and a printed circuit board positioned in the aperture, and wherein the printed circuit board is in communication with electrical traces in the flex circuit.

Example 29—A surgical instrument, comprising a shaft defining a longitudinal axis, an end effector, and an articulation joint, wherein the end effector is rotatably attached to the shaft about the articulation joint. The surgical instrument further comprises a flex circuit. The flex circuit comprises a shaft portion extending within the shaft, and an end effector portion extending within the end effector.

Example 30—The surgical instrument of Example 29, wherein the flex circuit is comprised of polyimide layers.

Example 31—The surgical instrument of Example 30, wherein the flex circuit further comprises metallic electrical traces on the polyimide layers.

Example 32—The surgical instrument of Example 31, wherein the metallic electrical traces are comprised of metallic ink.

Example 33—The surgical instrument of Examples 29, 30, 31, or 32, wherein the flex circuit further comprises silicone regions configured to permit the wiring harness to stretch.

Example 34—The surgical instrument of Example 33, wherein the metallic electrical traces extend over the silicone regions.

Example 35—The surgical instrument of Examples 33 or 34, wherein the metallic electrical traces follow arcuate paths across the silicone regions.

Example 36—The surgical instrument of Examples 31, 32, 33, 34, 35, or 36, wherein the metallic electrical traces are comprised of conductive ink.

Example 37—The surgical instrument of Examples 29, 30, 31, 32, 33, 34, 35, or 36, wherein the flex circuit further comprises an aperture defined therein and a printed circuit board positioned in the aperture, and wherein the printed circuit board is in communication with electrical traces in the flex circuit.

Example 38—The surgical instrument of Example 37, wherein the printed circuit board is comprised of fiberglass.

Example 39—The surgical instrument of Examples 29, 30, 31, 32, 33, 34, 35, 36, 37, or 38, wherein the flex circuit further comprises an aperture defined therein and a microchip positioned in the aperture, and wherein the microchip is in communication with electrical traces in the flex circuit.

Example Set 3

Example 1—A surgical instrument assembly, comprising a shaft, and an end effector extending from the shaft. The end effector comprises a first jaw, a second jaw movable relative to the first jaw, and an anvil. The end effector further comprises a staple cartridge channel, a staple cartridge positioned within the staple cartridge channel, and a plurality of pressure sensors positioned between the staple cartridge and the staple cartridge channel configured to detect clamping pressure within the end effector.

Example 2—The surgical instrument assembly of Example 1, wherein the end effector comprises a first side and a second side defined by a firing stroke path, and wherein the plurality of pressure sensors are positioned on both the first side and the second side.

Example 3—The surgical instrument assembly of Examples 1 or 2, wherein the plurality of pressure sensors are distributed longitudinally along a firing stroke path.

Example 4—The surgical instrument assembly of Examples 1, 2, or 3, further comprising a flex circuit coupled to the plurality of pressure sensors.

Example 5—A surgical instrument assembly, comprising a shaft, and a drive member movable within the shaft, wherein the drive member comprises a discontinuity portion. The surgical instrument assembly further comprises a flex circuit positioned within shaft and coupled to a surgical control circuit. The flex circuit comprises an integrated strain gauge mounted on the drive member within the discontinuity portion, wherein the surgical control circuit is configured to determine a load experienced by the drive member by way of the strain gauge.

Example 6—The surgical instrument assembly of Example 5, wherein the discontinuity portion comprises a necked-down portion.

Example 7—The surgical instrument assembly of Examples 5 or 6, wherein the drive member comprises a channel spine comprising a channel positioned on a distal end of the drive member, wherein the channel is configured to receive a staple cartridge therein.

Example 8—The surgical instrument assembly of Examples 5, 6, or 7, wherein the drive member comprises a first drive member, wherein the surgical instrument assembly further comprises a second drive member movable within the shaft, wherein the integrated strain gauge comprises a first integrated strain gauge, and wherein the flex circuit further comprises a second integrated strain gauge mounted on the second drive member.

Example 9—The surgical instrument assembly of Examples 5, 6, 7, or 8, wherein the flex circuit comprises a flexible portion and a non-flexible portion.

Example 10—The surgical instrument assembly of Examples 5, 6, 7, 8, or 9, wherein the drive member further comprises a primary body portion, and wherein the discontinuity portion is configured to experience more strain than the primary body portion.

Example 11—A surgical instrument system, comprising: a batch of staple cartridges, wherein each staple cartridge of the batch of staple cartridges comprises a predetermined load profile range. The surgical instrument system further comprises a surgical instrument assembly, wherein a staple cartridge of the batch of staple cartridges is configured to be installed into the surgical instrument assembly. The surgical instrument system further comprises a control circuit. The control circuit is configured to detect the predetermined load profile range of the installed staple cartridge, execute a motor control program to fire the installed staple cartridge with the surgical instrument assembly, and monitor an actual load profile of the installed staple cartridge when the installed staple cartridge is fired. The control circuit is further configured to compare the predetermined load profile range and the actual load profile, output the result of the comparison of the predetermined load profile range and the actual load profile, and modify the motor control program such that each subsequent staple cartridge of the batch of staple cartridges installed into the surgical instrument assembly is fired within the predetermined load profile range.

Example 12—A surgical instrument assembly, comprising a shaft, an end effector attached to the shaft, and a sub-component system configured to experience strain within the surgical instrument assembly. The surgical instrument assembly further comprises a woven conductive fabric attached to the sub-component system. The woven conductive fabric comprises a primary body portion, and a plurality of conductive fibers extending through the primary body portion. The surgical instrument assembly further comprises a control circuit configured to monitor the resistance of the woven conductive fabric and determine the load on the sub-component based on the resistance of the woven conductive fabric.

Example 13—The surgical instrument assembly of Example 12, wherein the plurality of conductive fibers are woven.

Example 14—The surgical instrument assembly of Examples 12 or 13, wherein the plurality of conductive fibers are wired in parallel.

Example 15—The surgical instrument assembly of Examples 12 or 13, wherein the plurality of conductive fibers are wired in series.

Example 16—The surgical instrument assembly of Examples 12, 13, 14, or 15, wherein the woven conductive fabric is attached to a grounded location within the shaft.

Example 17—The surgical instrument assembly of Examples 12, 13, 14, 15, or 16, wherein the woven conductive fabric comprises a first woven conductive fabric, wherein the first woven conductive fabric is configured to measure load applied to the sub-component system in a first plane, wherein the surgical instrument assembly further comprises a second woven conductive fabric configured to measure load applied to the sub-component system in a second plane.

Example 18—The surgical instrument assembly of Example 12, wherein the resistance of the woven conductive fabric is configured to correspond to displacement of the sub-component system.

Example 19—A surgical instrument assembly, comprising a shaft, an articulation joint, and an end effector attached to the shaft by way of the articulation joint. The surgical instrument assembly further comprises a firing member comprising a plurality of bands attached to each other, and a plurality of conductive fabrics, wherein each the band comprises the conductive fabric attached thereto. The surgical instrument assembly further comprises a control circuit configured to monitor the resistance of each conductive fabric to measure a parameter of each band.

Example 20—The surgical instrument assembly of Example 19, wherein each conductive fabric comprises a plurality of conductive fibers.

Example 21—The surgical instrument assembly of Example 19, wherein each conductive fabric comprises a single conductive fiber.

Example 22—The surgical instrument assembly of Examples 19, 20, or 21, wherein each band comprises an electrical contact positioned on a proximal end thereof.

Example 23—The surgical instrument assembly of Examples 19, 20, 21, 22, or 23, wherein the plurality of conductive fabrics comprises a plurality of conductive textiles.

Example 24—The surgical instrument assembly of Examples 19, 20, 21, 22, 23, or 24, wherein the plurality of conductive fabrics comprises a plurality of metalized conductive fabrics.

Example 25—A surgical instrument assembly, comprising a shaft, an end effector attached to the shaft, and an actuation member movable within the shaft, wherein the actuation member comprises a partially opaque portion. The surgical instrument assembly further comprises a sensing system configured to detect a load on the actuation member. The sensing system comprises a light source directed toward the partially opaque portion of the actuation member, and a sensor configured to detect resultant light diffraction caused by the partially opaque portion of the actuation member. The resultant light diffraction comprises a range of diffraction patterns corresponding to the load on the actuation member.

Example 26—A surgical instrument assembly, comprising a shaft comprising a first distal end, an articulation joint comprising a distal-most articulation link, and an end effector attached to the shaft by way of the articulation joint, wherein the end effector is coupled to the distal-most articulation link. The surgical instrument assembly further comprises an articulation drive member configured to articulate the end effector about the articulation joint, wherein the articulation drive member is movable relative to the shaft, and wherein the articulation drive member comprises a second distal end. The surgical instrument assembly further comprises a Hall effect sensor attached to the second distal end of the articulation joint, a magnet attached to the distal-most articulation link, wherein the distal-most articulation link is actuatable to a fully-articulated position. The surgical instrument assembly further comprises a surgical control circuit configured to monitor the position of the magnet by way of the Hall effect sensor, and advance the articulation drive member to move the distal-most articulation link to the fully-articulated position based on the position of the magnet.

Example 27—A surgical instrument assembly, comprising a shaft comprising a first distal end, an articulation joint comprising a distal-most articulation link, and an end effector attached to the shaft by way of the articulation joint, wherein the end effector is coupled to the distal-most articulation link. The surgical instrument assembly further comprises an articulation drive member configured to articulate the end effector about the articulation joint, wherein the articulation drive member is movable relative to the shaft, and wherein the articulation drive member comprises a second distal end. The surgical instrument assembly further comprises a Hall effect sensor attached to the second distal end of the articulation joint, a magnet attached to the distal-most articulation link, wherein the distal-most articulation link is actuatable to a fully-articulated position. The surgical instrument assembly further comprises a surgical control circuit configured to monitor a dynamic parameter of the magnet by way of the Hall effect sensor, and advance the articulation drive member to move the distal-most articulation link to the fully-articulated position based on the monitored dynamic parameter of the magnet.

Example 28—A surgical instrument, comprising a shaft comprising a frame, wherein the frame comprises a discontinuity portion. The surgical instrument further comprises a drive member movable within the shaft, and a flex circuit positioned within shaft and coupled to a control circuit. The flex circuit comprises an integrated strain gauge mounted on the frame within the discontinuity portion, wherein the control circuit is configured to determine a load experienced by the shaft by way of the strain gauge.

Example 29—The surgical instrument of Example 28, wherein the discontinuity portion comprises a notch, wherein the notch comprises a depth, wherein the integrated strain gauge comprises a thickness, and wherein the thickness does not exceed the depth.

Example 30—The surgical instrument of Examples 28 or 29, wherein the flex circuit comprises a longitudinal portion and the integrated strain gauge comprises a tab extending laterally from the longitudinal portion.

Example 31—The surgical instrument of Example 30, wherein the longitudinal portion is flexible and the tab is rigid.

Example 32—The surgical instrument of Examples 30 or 31, wherein the longitudinal portion is not mounted to the frame.

Example 33—The surgical instrument of Examples 30, 31, or 32, wherein the tab is mounted to the frame by at least one adhesive.

Example 34—The surgical instrument of Examples 28, 29, 30, 31, 32, or 33, wherein the discontinuity comprises a necked-down portion comprising a smaller cross-section than a distal frame portion positioned distally with respect to the necked-down portion and a proximal frame portion positioned proximally with respect to the necked-down portion.

Example 35—The surgical instrument of Examples 28, 29, 30, 31, 32, 33, or 34, wherein the discontinuity comprises a fin extending outwardly therefrom, and wherein the integrated strain gauge is mounted to the fin, Example 36—A surgical instrument, comprising a shaft comprising a frame, a drive member movable within the shaft, and a flex circuit positioned within shaft and coupled to a control circuit. The flex circuit comprises connector portions and flexible portions, wherein the connector portions connect the flexible portions, wherein the flexible portions comprise integrated strain gauges mounted to the frame, and wherein the connector portions comprise signal circuits in communication with the integrated strain gauges.

Example 37—The surgical instrument of Example 36, wherein the connector portions of the flex circuit comprises a plurality of attached layers, and wherein the flexible portions comprise less layers than the connector portions.

Example 38—A surgical instrument, comprising a shaft, a sub-component system configured to experience strain within the surgical instrument assembly, and a woven conductive fabric attached to the sub-component system. The woven conductive fabric comprises a body portion, and a plurality of conductive fibers extending through the body portion. The surgical instrument further comprises a control circuit configured to monitor the resistance of the woven conductive fabric and determine the load on the sub-component based on the resistance of the woven conductive fabric.

Example 39—The surgical instrument of Example 38, wherein the plurality of conductive fibers comprises a first portion in which the conductive fibers are oriented in a first direction and a second portion in which the conductive fibers are oriented in a second direction which is different than the first direction.

Example 40—The surgical instrument of Example 39, wherein the first direction is orthogonal to the second direction.

Example 41—The surgical instrument of Examples 38, 39, or 40, wherein the plurality of conductive fibers comprises a first portion attached to a first region of the sub-component system and a second portion attached to a second region of the sub-component system which is different than the first region.

Example 42—The surgical instrument of Example 41, wherein the first region is stiffer than the second region, wherein the first portion is used to measure a force in the sub-component system, and wherein the second portion is used to measure a strain in the subcomponent system.

Example 43—The surgical instrument of Examples 38, 39, 40, 41, or 42, wherein the plurality of conductive fibers comprises a first portion attached to a first sub-component of the sub-component system and a second portion attached to a second sub-component of the sub-component system which is different than the first sub-component.

Example 44—The surgical instrument of Example 43, wherein the first sub-component comprises a first layer of a firing member and the second sub-component comprises a second layer of the firing member.

Example Set 4

Example 1—A surgical instrument assembly, comprising a frame, an actuation member configured to be actuated through an actuation stroke within the frame, and a flex circuit extending through the frame. The flex circuit is configured to be commutatively coupled with a surgical control circuit, and wherein the flex circuit comprises an integrated sensor configured to detect a parameter of the actuation member.

Example 2—The surgical instrument assembly of Example 1, wherein the integrated sensor comprises a Hall effect sensor, and wherein the actuation member comprises a magnet positioned on the actuation member.

Example 3—The surgical instrument assembly of Examples 1 or 2, wherein the parameter comprises displacement of the actuation member.

Example 4—The surgical instrument assembly of Examples 1, 2, or 3, wherein the parameter comprises velocity of the actuation member.

Example 5—The surgical instrument assembly of Examples 1, 2, 3, or 4, wherein the parameter comprises acceleration of the actuation member.

Example 6—The surgical instrument assembly of Examples 1, 2, 3, 4, or 5, wherein the actuation member comprises a firing member.

Example 7—The surgical instrument assembly of Examples 1, 2, 3, 4, 5, or 6, wherein the actuation member comprises a closure member.

Example 8—The surgical instrument assembly of Examples 1, 2, 3, 4, 5, 6, or 7, wherein the actuation member comprises an articulation member.

Example 9—The surgical instrument assembly of Examples 1, 3, 4, 5, 6, 7, or 8, wherein the integrated sensor comprises a Hall effect sensor, wherein the actuation member comprises a plurality of magnets positioned on the actuation member, wherein a first magnet of the plurality of magnets is oriented in an inverted polar relationship to a second magnet of the plurality of magnets, wherein the Hall effect sensor is configured to sense both magnets simultaneously.

Example 10—The surgical instrument assembly of Examples 1, 2, 3, 4, 5, 6, 7, 8, or 9, wherein the actuation member comprises a rotary drive member.

Example 11—The surgical instrument assembly of Examples 1, 2, 3, 4, 5, 6, 7, 8, 9, or 10, wherein the actuation member comprises a rotary drive member, wherein the rotary drive member comprises alternating magnets positioned on the rotary drive member, and wherein the surgical instrument assembly further comprises a coil configured to alter a magnetic field.

Example 12—The surgical instrument assembly of Examples 1, 2, 3, 4, 5, 6, 7, 8, 9, 10, or 11, wherein the actuation member comprises a closure member, wherein the integrated sensor comprises a Hall effect sensor, wherein the closure member comprises a first magnet arranged at a first polarity relative to the Hall effect sensor and a second magnet arranged at a second polarity relative to the Hall effect sensor.

Example 13—The surgical instrument assembly of Examples 1, 2, 3, 4, 5, 6, 7, 8, 9, 10, 11, or 12, further comprising an end effector, comprising a first jaw, and a second jaw movable relative to the first jaw to clamp tissue. The actuation member comprises a closure member configured to move the second jaw relative to the first jaw, and wherein the parameter comprises displacement of the closure member to determine the position of the second jaw relative to the first jaw.

Example 14—The surgical instrument assembly of Examples 1, 2, 3, 4, 5, 6, 7, 8, 9, 10, 11, 12, or 13, wherein the actuation member comprises a plurality of magnets positioned on the actuation member, wherein the integrated sensor comprises a Hall effect sensor, and wherein the Hall effect sensor is configured to sense the plurality of magnets during the actuation stroke.

Example 15—The surgical instrument assembly of Example 14, wherein the plurality of magnets comprise a beginning-of-stroke magnet and an end-of-stroke magnet each arranged at a polarity relative to the Hall effect sensor that is opposite to a polarity at which all of the other magnets of the plurality of magnets are arranged.

Example 16—The surgical instrument assembly of Examples 1, 2, 3, 4, 5, 6, 7, 8, 9, 10, 11, 12, 13, 14, or 15, wherein the integrated sensor comprises a capacitive sensor.

Example 17—The surgical instrument assembly of Examples 1, 2, 3, 4, 5, 6, 7, 8, 9, 10, 11, 12, 13, 14, 15, or 16, wherein the integrated sensor comprises an optical sensor.

Example 18—A surgical instrument, comprising a housing, a shaft extending from the housing, an end effector extending from the shaft, a drive system, and a flexible circuit assembly extending within the shaft. The flexible circuit assembly comprises a power transmission backbone and a signal communication backbone, and wherein the signal communication backbone is separated from the power transmission backbone.

Example 19—The surgical instrument of Example 18, wherein the communication backbone comprises communication circuits in communication with a multiplexer.

Example 20—The surgical instrument of Examples 18 or 19, wherein the flexible circuit assembly comprises a first region, and a second region, wherein the first region and the second region are different. The flexible circuit assembly further comprises a first circuit in communication with the first region, a second circuit in communication with the second region, and a voltage control circuit configured to limit the voltage to the first region while providing a different voltage to the second region.

Example 21—The surgical instrument of Example 20, wherein the first region comprises a first sensor in communication with the first circuit, and wherein the second region comprises a second sensor in communication with the second circuit.

Example 22—The surgical instrument of Example 21, wherein the first sensor is configured to detect a first component of the drive system and the second sensor is configured to detect a second component of the drive system.

Example 23—The surgical instrument of Examples 20, 21, or 22, wherein the voltage provided to the first region is 6 volts and the voltage provided to the second region is 12 volts.

Example 24—The surgical instrument of Examples 18, 19, 20, 21, 22, or 23, wherein the flexible circuit assembly comprises a first region, and a second region, wherein the first region and the second region are different. The flexible circuit assembly further comprises a first circuit in communication with the first region, a second circuit in communication with the second region, and a controller configured to limit the quantity of data transmitted via the first circuit during a first operating mode and to increase the quantity of data transmitted via the first circuit during a second operating mode.

Example 25—The surgical instrument of Examples 20, 21, 22, 23, or 24, wherein the first region comprises a first sensor in communication with the first circuit, and wherein the second region comprises a second sensor in communication with the second circuit.

Example 26—The surgical instrument of Example 25, wherein the first sensor is configured to detect a first component of the drive system and the second sensor is configured to detect a second component of the drive system.

Example 27—A surgical instrument, comprising a housing, a shaft extending from the housing, and an end effector extending from the shaft. The surgical instrument further comprising a drive system; and a flexible circuit assembly extending within the shaft. The flexible circuit assembly comprises a first region comprising a first sensor circuit, wherein the first sensor circuit is configured to generate a first ping signal in response to a first event. The flexible circuit assembly further comprises a second region comprising a second sensor circuit, wherein the first region and the second region are different, wherein the second sensor circuit is configured to generate a second ping signal in response to a second event. The flexible circuit assembly further comprises a controller in communication with the first sensor circuit and the second sensor circuit. The controller holds the first sensor circuit in a first low power mode until it receives the first ping signal, wherein the controller places the first sensor circuit in a first high power mode once it receives the first ping signal. The controller holds the second sensor circuit in a second low power mode until it receives the second ping signal, and wherein the controller places the second sensor circuit in a second high power mode once it receives the second ping signal.

Example 28—A surgical instrument, comprising a housing, a shaft extending from the housing, an end effector extending from the shaft, a drive system; and a flexible circuit assembly extending within the shaft. The flexible circuit assembly comprises a first region comprising a first sensor circuit including a first sensor, and a second region comprising a second sensor circuit including a second sensor, wherein the first region and the second region are different. The flexible circuit assembly further comprises a controller in communication with the first sensor circuit and the second sensor circuit. The first sensor circuit is in a first low power mode until it receives a first ping signal from the controller, wherein the first sensor circuit enters into a first high power mode when it receives the first ping signal. The second sensor circuit is in a second low power mode until it receives a second ping signal from the controller, and wherein the second sensor circuit enters into a second high power mode when it receives the second ping signal.

Example 29—A surgical instrument, comprising a housing, a shaft extending from the housing, an end effector extending from the shaft, a drive system, and a flexible circuit assembly extending within the shaft. The flexible circuit assembly comprises a first region comprising a first sensor circuit, wherein the first sensor circuit is configured to generate a first ping signal in response to a first event. The flexible circuit assembly further comprises a second region comprising a second sensor circuit, wherein the first region and the second region are different, wherein the second sensor circuit is configured to generate a second ping signal in response to a second event. The flexible circuit assembly further comprises a controller in communication with the first sensor circuit and the second sensor circuit. The controller holds the first sensor circuit in a first low data bandwidth mode until it receives the first ping signal, wherein the controller places the first sensor circuit in a first high data bandwidth mode once it receives the first ping signal. The controller holds the second sensor circuit in a second low data bandwidth mode until it receives the second ping signal, and wherein the controller places the second sensor circuit in a second high data bandwidth mode once it receives the second ping signal.

Example 30—A surgical instrument, comprising a housing, a shaft extending from the housing, an end effector extending from the shaft, a drive system, and a flexible circuit assembly extending within the shaft. The flexible circuit assembly comprises a first region comprising a first sensor circuit including a first sensor, a second region comprising a second sensor circuit including a second sensor, wherein the first region and the second region are different. The flexible circuit assembly further comprises a controller in communication with the first sensor circuit and the second sensor circuit. The first sensor circuit is in a first low data bandwidth mode until it receives a first ping signal from the controller, wherein the first sensor circuit enters into a first high data bandwidth mode when it receives the first ping signal. The second sensor circuit is in a second low data bandwidth mode until it receives a second ping signal from the controller, wherein the second sensor circuit enters into a second high data bandwidth mode when it receives the second ping signal.

Example 31—The surgical instrument of Example 30, wherein the drive system comprises a drive member, wherein the first sensor and the second sensor are configured to detect the position of the drive member, wherein the second sensor circuit enters into the second high data bandwidth mode when the first sensor circuit detects the movement of the drive member.

Example 32—The surgical instrument of Examples 30 or 31, wherein the controller places the second sensor circuit in the second high data bandwidth mode if the controller determines that the total system data bandwidth sufficiently exceeds the data bandwidth consumed by the first sensor circuit.

Example 33—The surgical instrument of Examples 30, 31, or 32, wherein the controller increases the sampling rate of the second sensor when the second sensor circuit is in the second high data bandwidth mode.

Example 34—The surgical instrument of Examples 30, 31, 32, or 33, wherein the controller holds the second sensor circuit in the second low data bandwidth mode if the total system data bandwidth does not sufficiently exceed the data bandwidth consumed by the first sensor circuit.

Example 35—The surgical instrument of Examples 30, 31, 32, 33, or 34, wherein the controller throttles the second sensor circuit into the second low data bandwidth mode if the total system data bandwidth does not sufficiently exceed the data bandwidth consumed by the first sensor circuit.

Example 36—The surgical instrument of Examples 30, 31, 32, 33, 34, or 35, wherein the controller reduces the sampling rate of the second sensor to throttle the second sensor circuit into the second low data bandwidth mode.

Example 37—The surgical instrument of Examples 30, 31, 32, 33, 34, or 35, wherein the controller reduces the bit size of the data transmitted by the second sensor to throttle the second sensor circuit into the second low data bandwidth mode.

Example 38—A surgical instrument drive system, comprising an electric motor, a rotary drive shaft driveable by the electric motor, and a drive member driveable by the rotary drive shaft. The surgical instrument drive system further comprises an array of magnetic elements mounted to the rotary drive shaft, an array of sensing coils configured to detect the presence of the array of magnetic elements, and a controller in communication with the array of sensing coils. The controller is configured to assess the position of the drive member by data from the array of sensing coils.

Example 39—The surgical instrument drive system of Example 38, wherein the array of magnetic elements comprises a first magnetic element positioned on a first side of the rotary drive shaft and a second magnetic element positioned on a second side of the rotary drive shaft which is opposite the first side.

Example 40—The surgical instrument drive system of Example 39, wherein the first magnetic element comprises a negative pole facing the array of sensing coils and the second magnetic element comprises a positive pole facing the array of sensing coils.

Example 41—A surgical instrument, comprising a drive system that comprises a drive member movable between a first position and a second position during a drive stroke, and a magnetic member mounted to the drive member. The surgical instrument further comprises a Hall effect sensor configured to detect the magnetic element throughout the entire range of the drive stroke, and a controller in communication with the Hall effect sensor.

Example 42—The surgical instrument of Example 41, further comprising a shaft and a wiring harness extending through the shaft, wherein the Hall effect sensor is integrated into the wiring harness.

Example 43—A surgical instrument, comprising a drive system that comprises a drive member movable between a first position, a second position, and a third position during a drive stroke. The drive system further comprises a magnetic member mounted to the drive member. The surgical instrument further comprises a first Hall effect sensor configured to detect the magnetic element between the first position and the second position but not beyond the second position, a second Hall effect sensor configured to detect the magnetic element between the second position and the third position but not before the second position, and a controller in communication with the first Hall effect sensor and the second Hall effect sensor.

Example 44—The surgical instrument of Example 43, further comprising a shaft and a wiring harness extending through the shaft, wherein the first Hall effect sensor and the second Hall effect sensor are integrated into the wiring harness.

Example 45—A surgical instrument, comprising a drive system that comprises a drive member movable between a first position and a second position during a drive stroke, and a longitudinal array of magnetic members mounted to the drive member. The surgical instrument further comprises a Hall effect sensor configured to detect the array of magnetic elements, and a controller in communication with the Hall effect sensor.

Example 46—The surgical instrument of Example 45, wherein the array of magnetic members comprises a first magnetic member and a second magnetic member, wherein the first magnetic member is positioned distally with respect to the second magnetic member, and wherein the first magnetic member comprises a first polarity profile and the second magnetic member comprises a second polarity profile that is different than the first polarity profile.

Example 47—The surgical instrument of Example 45, wherein the array of magnetic members comprises a plurality of distal magnetic members and a proximal-most magnetic member, wherein each the distal magnetic member comprises a first polarity profile, and wherein the distal-most magnetic member comprises a second polarity profile which is different than the first polarity profile.

Example 48—The surgical instrument of Examples 45, 46, or 47, wherein the drive system comprises an electric motor in communication with the controller, and wherein the controller is configured to slow the electric motor when the Hall effect sensor detects the presence of the distal-most magnetic element.

Example 49—The surgical instrument of Examples 45, 46, 47, or 48, further comprising a shaft and a wiring harness extending through the shaft, wherein the Hall effect sensor is integrated into the wiring harness.

Example 50—A surgical instrument, comprising a shaft, and a drive system comprising a drive member movable between a first position and a second position during a drive stroke, and a wiring harness extending in the shaft. The wiring harness comprises a first capacitive plate, a second capacitive plate, and a gap defined between the first capacitive plate and the capacitive plate. The drive member is movable between the first capacitive plate and the second capacitive plate during the drive stroke. The surgical instrument further comprises a controller in communication with the first capacitive plate and the second capacitive plate, wherein the controller is configured to track the position of the drive member via the first capacitive plate and the second capacitive plate.

Example 51—A surgical instrument, comprising a shaft, and a drive system comprising a drive member movable between a first position and a second position during a drive stroke, and a wiring harness extending in the shaft. The wiring harness comprises a first capacitive plate, and a second capacitive plate, wherein the second capacitive plate is positioned distally with respect to the first capacitive plate. The surgical instrument further comprises a controller in communication with the first capacitive plate and the second capacitive plate, wherein the controller is configured to track the position of the drive member via the first capacitive plate and the second capacitive plate.

Example 52—A surgical instrument, comprising a shaft, and a drive system comprising a drive member movable between a first position and a second position during a drive stroke, wherein the drive member comprises a light emitting diode configured to emit light. The surgical instrument further comprises a wiring harness extending in the shaft comprising an optical sensor, wherein the optical sensor is configured to detect the intensity of the light. The surgical instrument further comprises a controller in communication with the optical sensor, wherein the controller is configured to track the position of the drive member by data from the optical sensor.

Example 53—A surgical instrument, comprising a shaft, and a drive system comprising a drive member movable between a first position and a second position during a drive stroke, wherein the drive member comprises a longitudinal array of light emitting diodes configured to emit light. The surgical instrument further comprises a screen comprising an aperture extending therethrough, wherein the longitudinal array of light emitting diodes is positioned on a first side of the screen. The surgical instrument further comprises a wiring harness extending in the shaft comprising an optical sensor positioned on a second side of the screen, wherein the optical sensor is aligned with the aperture and is configured to detect the intensity of light emitted through the aperture. The surgical instrument further comprises a controller in communication with the optical sensor, wherein the controller is configured to track the position of the drive member by data from the optical sensor.

Example Set 5

Example 1—A surgical instrument assembly, comprising a shaft, an end effector attached to the shaft, and a sensing system positioned within the shaft. The sensing system is configured to detect a parameter of the surgical instrument assembly, and detect a presence of outside interference that affects the parameter detection of the surgical instrument assembly.

Example 2—The surgical instrument assembly of Example 1, wherein the sensing system comprises a plurality of Hall effect sensors and a magnet configured to be sensed by the plurality of Hall effect sensors, and wherein the plurality of Hall effect sensors comprises a range of expected output values corresponding to the parameter.

Example 3—The surgical instrument assembly of Example 1, wherein the sensing system comprises a plurality of Hall effect sensors and a plurality of magnets configured to be sensed by the plurality of Hall effect sensors, and wherein the plurality of Hall effect sensors comprises a range of expected output values corresponding to the parameter.

Example 4—A surgical instrument system, comprising a surgical instrument assembly that comprises a shaft, an end effector attached to the shaft, and a sensing system positioned within the shaft. The sensing system is configured to detect a parameter of the surgical instrument assembly, and detect a presence of outside interference that affects the parameter detection of the surgical instrument assembly. The surgical instrument system further comprises a control circuit configured to receive a signal from the sensing system, determine if the received signal has been altered by outside interference, and adjust the control program if the signal has been determined to have been altered by outside interference.

Example 5—A surgical instrument system, comprising a surgical instrument assembly that comprises a motor, an actuation member configured to be actuated by the motor, and a shaft. The surgical instrument assembly further comprises an end effector attached to the shaft, a first sensing system positioned within the shaft configured to monitor a parameter of the actuation member, and a second sensing system configured monitor a parameter of the motor. The surgical instrument system further comprises a control circuit comprising a motor control program configured to run the motor. The control circuit is configured to compare the monitored parameter of the actuation member and the monitored parameter of the motor, and adjust the motor control program if the comparison of the monitored parameter of the actuation member and the monitored parameter of the motor does not comprise an expected relationship.

Example 6—A surgical instrument system, comprising a surgical instrument control interface comprising a first wireless communication module, and a first surgical instrument assembly configured to be attached to the surgical instrument control interface, wherein the first surgical instrument assembly comprises a second wireless communication module. The surgical instrument system further comprises a second surgical instrument assembly configured to be attached to the surgical instrument control interface, wherein the second surgical instrument assembly comprises a third wireless communication module. The surgical instrument system further comprises a control circuit. The control circuit is configured to receive wireless communication signals from the second wireless communication module and the third wireless communication module prior to either of the first surgical instrument assembly or the second surgical instrument assembly being attached to the surgical instrument control interface. The control circuit is further configured to alert a user of the identification of the first surgical instrument assembly and the second surgical instrument assembly based on the received wireless communication signals.

Example 7—A surgical instrument system, comprising a surgical instrument control interface comprising an interface field detection sensor, and a first surgical instrument assembly configured to be attached to the surgical instrument control interface, wherein the first surgical instrument assembly comprises a first wireless communication module and a first field detection sensor. The surgical instrument system further comprising a second surgical instrument assembly configured to be attached to the surgical instrument control interface, wherein the second surgical instrument assembly comprises a second wireless communication module and a second field detection sensor. The surgical instrument system further comprises a controller. The controller is configured to receive wireless communication signals from the first wireless communication module containing data from the first field detection sensor and communication signals from the second wireless communication module containing data from the second field detection sensor. The controller is further configured to alert a user of the existence of field interference with the surgical instrument system based on the received wireless communication signals.

Example 8—The surgical instrument system of Example 7, wherein the controller is configured to assess whether the field interference is being generated by a source external to the surgical instrument system.

Example 9—The surgical instrument system of Examples 7 or 8, wherein the controller is configured to assess when the field interference is constant and, when constant, discount the constant field interference while operating the surgical instrument system.

Example 10—The surgical instrument system of Examples 7, 8, or 9, wherein the controller is configured to assess when the field interference is stationary and, when stationary, discount the stationary field interference while operating the surgical instrument system.

Example 11—The surgical instrument system of Examples 7, 8, 9, or 10, wherein the controller is configured to assess when the field interference is not constant and stationary and warn the user of the surgical instrument system that one or more systems of the surgical instrument system may not function properly.

Example 12—The surgical instrument system of Example 11, wherein the controller is further configured to place the surgical instrument system in a limp mode by limiting the operation of one or more systems.

Example 13—The surgical instrument system of Examples 11, or 12, wherein the controller is further configured to place the surgical instrument system in a limp mode by limiting the speed of one or more systems.

Example 14—The surgical instrument system of Examples 11, 12, or 13, wherein the controller is further configured to place the surgical instrument system in a limp mode by limiting the torque of one or more systems.

Example 15—The surgical instrument system of Examples 11, 12, 13, or 14, wherein the controller is further configured to place the surgical instrument system in a limp mode by limiting the power of one or more systems.

Example 16—The surgical instrument system of Examples 11, 12, 13, 14, or 15, wherein the controller is further configured to place the surgical instrument system in a limp mode by preventing the operation of one or more the systems.

Example 17—The surgical instrument system of Examples 11, 12, 13, 14, 15, or 16, wherein the controller is further configured to place the surgical instrument system in a limp mode by limiting the direction of one or more systems.

Example 18—The surgical instrument system of Examples 7, 8, 9, 10, 11, 12, 13, 14, 15, 16, or 17, wherein the controller is configured to assess whether the field interference is being generated by a source internal to the surgical instrument system.

Example 19—The surgical instrument system of Examples 7, 8, 9, 10, 11, 12, 13, 14, 15, 16, 17, or 18, wherein the controller is configured to determine the origin of the field interference and reduce the field interference below a threshold.

Example 20—A surgical instrument system, comprising a first Hall effect sensor, a second Hall effect sensor, and a controller. The controller is configured to receive signals from the first Hall effect sensor and the second Hall effect sensor, determine the presence of field interference with at least one of the first Hall effect sensor and the second Hall effect sensor, and alert a user of the existence of field interference with the surgical instrument system based on the signals.

Example 21—The surgical instrument system of Example 20, wherein the controller is configured to assess whether the field interference is being generated by a source external to the surgical instrument system.

Example 22—The surgical instrument system of Examples 20 or 21, wherein the controller is configured to assess when the field interference is constant and, when constant, discount the constant field interference while operating the surgical instrument system.

Example 23—The surgical instrument system of Examples 20, 21, or 22, wherein the controller is configured to assess when the field interference is stationary and, when stationary, discount the stationary field interference while operating the surgical instrument system.

Example 24—The surgical instrument system of Examples 20, 21, 22, or 23, wherein the controller is configured to assess when the field interference is not constant and stationary and warn the user of the surgical instrument system that one or more systems of the surgical instrument system may not function properly.

Example 25—The surgical instrument system of Example 24, wherein the controller is further configured to place the surgical instrument system in a limp mode by limiting the operation of one or more systems.

Example 26—The surgical instrument system of Examples 24 or 25, wherein the controller is further configured to place the surgical instrument system in a limp mode by limiting the speed of one or more systems.

Example 27—The surgical instrument system of Examples 24, 25, or 26, wherein the controller is further configured to place the surgical instrument system in a limp mode by limiting the torque of one or more systems.

Example 28—The surgical instrument system of Examples 24, 25, 26, or 27, wherein the controller is further configured to place the surgical instrument system in a limp mode by limiting the power of one or more systems.

Example 29—The surgical instrument system of Examples 24, 25, 26, 27, or 28, wherein the controller is further configured to place the surgical instrument system in a limp mode by preventing the operation of one or more systems.

Example 30—The surgical instrument system of Examples 24, 25, 26, 27, 28, or 29, wherein the controller is further configured to place the surgical instrument system in a limp mode by limiting the direction of one or more systems.

Example 31—The surgical instrument system of Examples 20, 21, 22, 23, 24, 25, 26, 27, 28, 29, or 30, wherein the controller is configured to assess whether the field interference is being generated by a source internal to the surgical instrument system.

Example 32—The surgical instrument system of Examples 20, 21, 22, 23, 24, 25, 26, 27, 28, 29, 30, or 31, wherein the controller is configured to determine the origin of the field interference and reduce the field interference below a threshold.

Example 33—The surgical instrument system of Examples 20, 21, 22, 23, 24, 25, 26, 27, 28, 29, 30, 31, or 32, further comprising a drive system including a drive member, wherein the first Hall effect sensor is configured to detect the position of the drive member.

Example 34—The surgical instrument system of Example 33, wherein the second Hall effect sensor is configured to detect the position of the drive member.

Example 35—The surgical instrument system of Example 33, wherein the second Hall effect sensor is dedicated to sensing the field interference and not the position of the drive member.

Example 36—The surgical instrument system of Examples 20, 21, 22, 23, 24, 25, 26, 27, 28, 29, 30, 31 or, 32, wherein the first Hall effect sensor and the second Hall effect sensor are dedicated to detecting the field interference and not the position of a drive member.

Example Set 6

Example 1—A surgical instrument assembly, comprising a shaft, an end effector attached to the shaft, and an actuation member positioned within the shaft. The surgical instrument assembly further comprises a motor configured to actuate the actuation member, an orientation detection system configured to determine the orientation of the shaft relative to the motor, and a control circuit configured to adjust the actuation of the motor based on the determined orientation of the shaft relative to the motor.

Example 2—A surgical instrument assembly, comprising a shaft, an end effector attached to the shaft, and an actuation member positioned within the shaft. The surgical instrument assembly further comprises a motor configured to actuate the actuation member; an orientation detection system configured to determine the orientation of the end effector relative to the motor, and a control circuit configured to adjust the actuation of the motor based on the determined orientation of the end effector relative to the motor.

Example 3—A surgical instrument system, comprising a housing interface comprising a motor, and a shaft assembly attachable to the housing interface. The shaft assembly comprises a shaft, an end effector attached to the shaft, an actuation member positioned within the shaft, and an orientation detection system configured to determine the orientation of the shaft relative to the housing interface. The surgical instrument system further comprises a control circuit comprising a motor control program configured to run the motor, wherein the control circuit is configured to adjust the motor control program based on the determined orientation of the shaft relative to the housing interface.

Example 4—The surgical instrument system of Example 3, wherein the control circuit is configured to adjust a rate of actuation of the actuation member.

Example 5—The surgical instrument system of Examples 3 or 4, wherein the control circuit is configured to adjust a stroke length of the actuation member.

Example 6—A surgical instrument system, comprising a handle comprising a motor and a trigger configured to actuate the motor, and a shaft assembly attachable to the handle. The shaft assembly comprises a shaft, an end effector attached to the shaft, and an actuation member positioned within the shaft. The surgical instrument system further comprises an orientation detection system configured to determine the orientation of the handle, and a control circuit configured to adjust a force required to actuate the trigger based on the determined orientation of the handle.

Example 7—The surgical instrument system of Example 6, wherein the control circuit is configured to reduce the force required to actuate the trigger when the handle is determined to be inverted.

Example 8—A surgical instrument system, comprising a housing. The housing comprises an attachment interface comprising a plurality of slip ring contacts, wherein each slip ring contact comprises an interrupted conductor path. The housing further comprises a motor. The surgical instrument system further comprises a shaft assembly attachable to the attachment interface, wherein the shaft assembly is configured to be rotated about a longitudinal shaft axis relative to the attachment interface. The shaft assembly comprises a proximal attachment portion comprising electrical contacts configured to engage the slip ring contacts when the shaft assembly is attached to the attachment interface. The shaft assembly further comprises a shaft, an end effector attached to the shaft; and an actuation member positioned within the shaft. The surgical instrument system further comprises a control circuit. The control circuit is configured to monitor the position of the electrical contacts relative to the slip ring contacts, and determine the orientation of the shaft assembly based on the monitored position of the electrical contacts relative to the slip ring contacts.

Example 9—A surgical instrument system, comprising a surgical instrument assembly that comprises a shaft, and an end effector attached to the shaft. The end effector comprises a first jaw, and a second jaw movable relative to the first jaw. The surgical instrument system further comprises a control circuit. The control circuit is configured to determine the orientation of the end effector relative to gravity, and adjust control motions applied to the end effector based on the determined orientation of the end effector relative to gravity.

Example 10—A surgical instrument system configured for use on a patient, wherein the surgical instrument system comprises a surgical instrument assembly. The surgical instrument assembly comprises a shaft, and an end effector attached to the shaft. The surgical instrument system further comprises a control circuit. The control circuit is configured to determine the orientation of the patient, and adjust a control program of the surgical instrument assembly based on the determined orientation of the patient.

Example 11—A surgical instrument system configured for treating a patient, wherein the surgical instrument system comprises a surgical instrument. The surgical instrument comprises a shaft, and an end effector extending from the shaft. The surgical instrument system further comprises a control circuit. The control circuit is configured to determine the orientation of the patient, determine the orientation of the surgical instrument, and adjust a control program of the surgical instrument assembly based on the determined orientation of the patient and the determined orientation of the surgical instrument.

Example 12—A surgical instrument system, comprising a surgical instrument. The surgical instrument comprises a handle, a shaft defining a longitudinal axis, and a rotation joint rotatably connecting the shaft to the handle, wherein the shaft is rotatable relative to the handle about the longitudinal axis. The surgical instrument further comprises an end effector extending from the shaft. The end effector comprises a first jaw, and a second jaw movable relative to the first jaw. The surgical instrument system further comprises a control circuit configured to determine the orientation of the end effector relative to gravity, and adjust control motions applied to the end effector based on the determined orientation of the end effector relative to gravity.

Example 13—A surgical instrument system, comprising a surgical instrument. The surgical instrument comprises a shaft defining a longitudinal axis, and an end effector extending from the shaft. The end effector comprises a first jaw, a second jaw movable relative to the first jaw about a closure joint, and an articulation joint, wherein the first jaw and the second jaw are articulatable laterally relative to the longitudinal axis. The surgical instrument further comprises a rotation joint rotatably connecting the end effector to the shaft, wherein the end effector is rotatable relative to the shaft about the longitudinal axis. The surgical instrument system further comprises a control circuit. The control circuit is configured to determine the orientation of the end effector relative to gravity, and adjust control motions applied to the end effector based on the determined orientation of the end effector relative to gravity.

Example 14—A surgical instrument system, comprising a handle comprising a motor and a trigger configured to actuate the motor, and a shaft extending from the handle. The shaft comprises a shaft, an end effector attached to the shaft, and an actuation member. The surgical instrument system further comprises an orientation detection system configured to determine the orientation of the handle relative to gravity, and a control circuit configured to adjust a force required to actuate the trigger based on the determined orientation of the handle.

Example 15—The surgical instrument system of Example 14, wherein the control circuit is configured to reduce the force required to actuate the trigger when the handle is determined to be inverted relative to gravity.

Example 16—The surgical instrument system of Example 14, wherein the control circuit is configured to increase the force required to actuate the trigger when the handle is determined to be inverted relative to gravity.

Example 17—A surgical instrument system, comprising a handle comprising a motor and a trigger configured to actuate the motor, and a shaft. The shaft comprises a shaft defining a longitudinal axis, an end effector attached to the shaft, and an actuation member. The surgical instrument system further comprises a rotation joint rotatably connecting the shaft to the handle such that the shaft is rotatable relative to the handle about the longitudinal axis, an orientation detection system configured to determine the orientation of the handle relative to the shaft, and a control circuit configured to adjust a force required to actuate the trigger based on the determined orientation of the handle.

Example 18—The surgical instrument system of Example 17, wherein the control circuit is configured to reduce the force required to actuate the trigger when the handle is determined to be inverted relative to the shaft.

Example 19—The surgical instrument system of Example 17, wherein the control circuit is configured to increase the force required to actuate the trigger when the handle is determined to be inverted relative to the shaft.

Example Set 7

Example 1—A surgical instrument system, comprising a surgical instrument assembly. The surgical instrument assembly comprises a shaft, and an end effector attached to the shaft. The surgical instrument system further comprises a control circuit configured to limit operation of the surgical instrument assembly to a limited-capabilities state based on a predefined software configuration.

Example 2—The surgical instrument system of Example 1, wherein the control circuit is configured to receive an input from a user to unlock a full-capabilities state of the surgical instrument assembly.

Example 3—The surgical instrument system of Examples 1 or 2, wherein the limited-capabilities state comprises limiting an actuation-member sensing system to a reduced functional state.

Example 4—A surgical instrument system, comprising a surgical instrument assembly that comprises a shaft, and an end effector attached to the shaft. The surgical instrument system further comprises a control circuit. The control circuit is configured to determine a limited-capabilities operating mode, and recommend the limited-capabilities operating mode to a user of the surgical instrument assembly.

Example 5—A surgical instrument system, comprising a surgical instrument assembly. The surgical instrument assembly comprises a shaft, an end effector attached to the shaft, and an electro-mechanical system. The surgical instrument system that comprises a control circuit configured to limit a functional range of the electro-mechanical system based on a level of available power to the surgical instrument assembly.

Example 6—A surgical instrument system, comprising a surgical communications hub and a surgical instrument. The surgical instrument comprises a controller, a first set of firmware, and a communications system. The communications system is configured to communicate with the surgical communications hub, wherein the first set of firmware is suitable for the surgical instrument to perform a first surgical technique. The controller is selectively operable by the user of the surgical instrument system to upload a second set of firmware from the surgical communications hub that makes the surgical instrument suitable to perform a second surgical technique which is different than the first surgical technique.

Example 7—The surgical instrument system of Example 6, wherein the surgical instrument comprises a shaft, an end effector, an articulation joint rotatably connecting the end effector to the shaft, and an articulation drive system. The articulation drive system comprises an articulation motor in communication with the controller. The controller is configured to move the end effector through a first articulation range when the controller is using the first set of firmware. The controller is configured to move the end effector through a second articulation range when the controller is using the second set of firmware. The first articulation range is less than the second articulation range.

Example 8—The surgical instrument system of Example 6, wherein the surgical instrument comprises a shaft, an end effector, an articulation joint rotatably connecting the end effector to the shaft, and an articulation drive system. The articulation drive system comprises an articulation motor in communication with the controller. The controller is configured to move the end effector through a first articulation range when the controller is using the first set of firmware. The controller is configured to move the end effector through a second articulation range when the controller is using the second set of firmware. The first articulation range is greater than the second articulation range.

Example 9—The surgical instrument system of Example 6, wherein the surgical instrument comprises a shaft, an end effector, and a first articulation joint defining a first articulation axis. The surgical instrument further comprises a second articulation joint defining a second articulation axis, a first articulation drive system comprising a first articulation motor in communication with the controller, and a second articulation drive system comprising a second articulation motor in communication with the controller. The controller configured to use the first articulation drive system but not the second articulation drive system when the controller is using the first set of firmware. The controller configured to use the first articulation drive system and the second articulation drive system when the controller is using the second set of firmware.

Example 10—The surgical instrument system of Example 6, wherein the surgical instrument comprises a shaft, an end effector, and a first articulation joint defining a first articulation axis. The surgical instrument further comprises a second articulation joint defining a second articulation axis, a first articulation drive system comprising a first articulation motor in communication with the controller, and a second articulation drive system comprising a second articulation motor in communication with the controller. The controller is configured to use the first articulation drive system and the second articulation drive system when the controller is using the first set of firmware. The controller is configured to use the first articulation drive system but not the second articulation drive system when the controller is using the second set of firmware.

Example 11—The surgical instrument system of Example 6, wherein the surgical instrument comprises a shaft, and an end effector. The end effector comprises a first jaw and a second jaw, wherein the first jaw is rotatable relative to the second jaw. The surgical instrument further comprises a drive system configured to move the first jaw relative to the second jaw. The drive system is in communication with the controller. The controller is configured to move the first jaw through a first range of motion when using the first set of firmware. The controller is configured to move the first jaw through a second range of motion when using the second set of firmware. The second range of motion is larger than and overlaps the first range of motion.

Example 12—The surgical instrument system of Example 6, wherein the surgical instrument comprises a shaft, and an end effector. The end effector comprises a first jaw and a second jaw, wherein the first jaw is rotatable relative to the second jaw. The surgical instrument further comprises a drive system configured to move the first jaw relative to the second jaw. The drive system is in communication with the controller. The controller is configured to move the first jaw through a first range of motion when using the first set of firmware. The controller is configured to move the first jaw through a second range of motion when using the second set of firmware. The first range of motion is larger than and overlaps the second range of motion.

Example 13—The surgical instrument system of Examples 6, 7, 8, 9, 10, 11, or 12, wherein the surgical instrument comprises a drive system including an electric motor in communication with the controller and a power source. The controller limits the power supplied to the electric motor from the power source to a first power limit when using the first set of firmware. The controller limits the power supplied to the electric motor from the power source to a second power limit when using the second set of firmware. The second power limit is higher than the first power limit.

Example 14—The surgical instrument system of Examples 6, 7, 8, 9, 10, 11, or 12, wherein the surgical instrument comprises a drive system including an electric motor in communication with the controller and a power source. The controller limits the power supplied to the electric motor from the power source to a first power limit when using the first set of firmware. The controller limits the power supplied to the electric motor from the power source to a second power limit when using the second set of firmware. The second power limit is lower than the first power limit.

Example 15—The surgical instrument system of Examples 6, 7, 8, 9, 10, 11, 12, 13, or 14, wherein the surgical instrument comprises an energy delivery system in communication with the controller and a power source. The controller limits the power supplied to the energy delivery system from the power source to a first power limit when using the first set of firmware. The controller limits the power supplied to the energy delivery system from the power source to a second power limit when using the second set of firmware. The second power limit is higher than the first power limit.

Example 16—The surgical instrument system of Examples 6, 7, 8, 9, 10, 11, 12, 13, or 14, wherein the surgical instrument comprises an energy delivery system in communication with the controller and a power source. The controller limits the power supplied to the energy delivery system from the power source to a first power limit when using the first set of firmware. The controller limits the power supplied to the energy delivery system from the power source to a second power limit when using the second set of firmware. The second power limit is lower than the first power limit.

Example 17—The surgical instrument system of Examples 6, 7, 8, 9, 10, 11, 12, 13, 14, 15, or 16 wherein the controller powers the communications system of the surgical instrument to have a first range when using the first set of firmware, wherein the controller powers the communications system of the surgical instrument to have a second range when using the second set of firmware, and wherein the second range is longer than the first range.

Example 18—The surgical instrument system of Examples 6, 7, 8, 9, 10, 11, 12, 13, 14, 15, or 16, wherein the controller powers the communications system of the surgical instrument to have a first range when using the first set of firmware, wherein the controller powers the communications system of the surgical instrument to have a second range when using the second set of firmware, and wherein the second range is shorter than the first range.

Example 19—The surgical instrument system of Examples 6, 7, 8, 9, 10, 11, 12, 13, 14, 15, 16, 17, or 18, wherein the surgical communications hub comprises a payment protocol that requires a payment before delivering the second set of firmware to the surgical instrument.

Example 20—The surgical instrument system of Examples 6, 7, 8, 9, 10, 11, 12, 13, 14, 15, 16, 17, 18, or 19, wherein the controller is configured to at least one of override or limit changes downloaded to the surgical instrument based on the sensed performance of the surgical instrument.

Example Set 8

Example 1—A surgical instrument system, comprising a surgical instrument assembly configured to be attached to an actuation interface. The surgical instrument assembly comprises a shaft, an end effector attached to the shaft, and a memory. The surgical instrument system further comprises a control circuit configured to run the actuation interface. The control circuit is configured to receive calibration parameters from the memory based on the surgical instrument assembly, and update a motor control program based on the received calibration parameters.

Example 2—A surgical instrument system, comprising a surgical instrument assembly configured to be attached to an actuation interface. The surgical instrument assembly comprises a shaft, an end effector attached to the shaft, and a memory. The surgical instrument system further comprises a control circuit configured to run the actuation interface. The control circuit is configured to receive component identifiers from the memory based on the surgical instrument assembly, and determine a motor control program based on the received component identifiers.

Example 3—A surgical instrument system, comprising a surgical instrument assembly configured to be attached to an actuation interface. The surgical instrument assembly comprises a modular shaft comprising a first memory, and a modular end effector. The modular end effector comprises a second memory, wherein the modular end effector is configured to be attached to shaft. The modular end effector further comprises a control circuit configured to run the actuation interface. The control circuit is configured to receive a first component-specific information from the first memory and a second component-specific information from the second memory, and determine a motor control program based on the received first component-specific information and the received second component-specific information.

Example 4—A surgical instrument system, comprising a surgical instrument assembly comprising a plurality of sub-systems, and a control interface. The control interface comprises an attachment portion, wherein the surgical instrument assembly is configured to be attached to the attachment portion. The control interface further comprises one or more motors configured to actuate the plurality of sub-systems. The surgical instrument system further comprises a control circuit. The control circuit is configured to identify each sub-system of the surgical instrument assembly when the surgical instrument assembly is attached to the attachment portion, actuate each sub-system through a test stroke, and optimize one or more control programs according to the test stroke.

Example 5—A surgical instrument system, comprising a surgical instrument assembly comprising a plurality of sub-systems, and a control interface. The control interface comprises an attachment portion, wherein the surgical instrument assembly is configured to be attached to the attachment portion. The control interface further comprises one or more motors configured to actuate the plurality of sub-systems. The surgical instrument system further comprises a control circuit. The control circuit is configured to identify each sub-system of the surgical instrument assembly when the surgical instrument assembly is attached to the attachment portion, actuate each sub-system through a test stroke, and generates one or more control programs according to the test stroke.

Example 6—The surgical instrument system of Example 5, wherein the control circuit is further configured to compare the test stroke to actuations of surgical instrument assemblies previously attached to the control interface, and determine if the control interface is causing variation in actuations and if the surgical instrument assembly is causing variation in actuation.

Example 7—A surgical instrument system, comprising a surgical instrument assembly. The surgical instrument assembly comprises a shaft, an end effector attached to the shaft, a drive system positioned within the shaft, and an onboard memory configured to store identification data corresponding to the drive system. The surgical instrument system further comprises a control circuit. The control circuit is configured to access the identification data stored on the onboard memory, identify the surgical instrument assembly based on the accessed identification data, and determine a motor control program to actuate the surgical instrument assembly based on the identified surgical instrument assembly.

Example 8—A surgical instrument system, comprising a handle. The handle comprises a frame, a first drive system including a first drive motor, and a second drive system including a second drive motor. The handle further comprises a control system in communication with the first drive motor and the second drive motor, and an attachment sensor in communication with the control system. The surgical instrument system further comprises a shaft attachable to the handle. The shaft comprises a connector portion releasably mountable to the frame, a first drive member comprising a first proximal connector that is coupled to the first drive system when the shaft is attached to the handle, and a second drive member comprising a second proximal connector that is coupled to the second drive system when the shaft is attached to the handle. The control system is configured to move the first drive member through a first test stroke when the shaft is attached to the handle to assess at least one of slop, backlash, friction loss, stroke variation, and motor stall in the first drive system and the first drive member. The control system is configured to move the second drive member through a second test stroke when the shaft is attached to the handle to assess at least one of slop, backlash, friction loss, stroke variation, and motor stall in the second drive system and the second drive member.

Example 9—The surgical instrument system of Example 8, wherein the controller is configured to alter the motor control algorithm for controlling the first drive motor based on the controller's assessment of the first drive system and the first drive member, and wherein the controller is configured to alter the motor control algorithm for controlling the second drive motor based on the controller's assessment of the second drive system and the second drive member.

Example 10—A surgical instrument system, comprising a surgical instrument. The surgical instrument comprises an actuation interface comprising an interface memory device, a drive system comprising an electric motor, a motor control program, and a shaft releasably attachable to the actuation interface. The shaft comprises a control circuit configured to access the interface memory device when the shaft is attached to the actuation interface to obtain data regarding the actuation interface. The shaft further comprises a shaft memory device in communication with the control circuit, and a communications circuit in communication with the control circuit. The surgical instrument system further comprises a surgical hub configured to communicate with the control circuit and a remote server. The surgical hub is configured to receive data from the interface memory device and the shaft memory device and transmit the data to the remote server to determine changes to the motor control program that will improve the operation of the surgical instrument. The control circuit is configured to update the motor control program based on the changes.

Example 11—The surgical instrument system of Example 10, wherein the data includes an identification number of the actuation interface and an identification number of the shaft.

Example 12—The surgical instrument system of Examples 10 or 11, wherein the data includes a manufacturing date of the actuation interface and a manufacturing date of the shaft.

Example 13—The surgical instrument system of Examples 10, 11, or 12, wherein the data includes a manufacturing site of the actuation interface and a manufacturing site of the shaft.

Example 14—The surgical instrument system of Examples 10, 11, 12, or 13, wherein the data is used to evaluate the tolerances of the drive system and a drive member of the shaft engaged with the drive system to estimate the stroke variation of the drive member.

Example 15—The surgical instrument system of Example 14, wherein the server is configured to store the tolerance evaluation, stroke variation estimate, and motor control program changes.

Example 16—The surgical instrument system of Examples 10, 11, 12, 13, 14, or 15, wherein the server is configured to transmit the motor control program changes to other actuation interface and shaft pairings that have the same data.

Example 17—The surgical instrument system of Examples 10, 11, 12, 13, 14, 15, or 16, wherein the server is configured to transmit the motor control program changes to other actuation interface and shaft pairings that have the same identification numbers.

Example 18—The surgical instrument system of Examples 10, 11, 12, 13, 14, 15, 16, or 17, wherein the shaft identification number is stored on an RFID tag on the shaft and the actuation interface identification number is stored on an RFID tag on the actuation interface.

Example 19—The surgical instrument system of Examples 10, 11, 12, 13, 14, 15, 16, 17, or 18, wherein at least one of the actuation interface and the shaft comprises a lockout configured to limit the operation of the drive member, and wherein the controller is configured to actuate the lockout if the stroke variation estimate is outside of an acceptable range.

Example 20—The surgical instrument system of Examples 10, 11, 12, 13, 14, 15, 16, 17, 18, or 19, further comprising a lockout override configured to delimit the operation of the drive member.

Example 21—The surgical instrument system of Examples 10, 11, 12, 13, 14, 15, 16, 17, 18, 19, or 20, wherein the controller is configured to monitor the actual stroke of the drive member, assess the actual stroke variation of the drive member, compare the actual stroke variation to the stroke variation estimate, and transmit the actual stroke variation to the surgical hub. The surgical hub is configured to transmit the actual stroke variation to the remote server. The remote server is configured to revise the stroke variation estimate based on the actual stroke variation.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument assembly, comprising:
    a shaft;
    an end effector attached to said shaft; and
    a sensing system positioned within said shaft, wherein said sensing system is configured to:
        detect a parameter of said surgical instrument assembly; and
        detect a presence of outside interference that affects the parameter detection of said surgical instrument assembly.

2. The surgical instrument assembly of claim 1, wherein said sensing system comprises a plurality of Hall effect sensors and a magnet configured to be sensed by said plurality of Hall effect sensors, and wherein said plurality of Hall effect sensors comprises a range of expected output values corresponding to said parameter.

3. The surgical instrument assembly of claim 1, wherein said sensing system comprises a plurality of Hall effect sensors and a plurality of magnets configured to be sensed by said plurality of Hall effect sensors, and wherein said plurality of Hall effect sensors comprises a range of expected output values corresponding to said parameter.

4. The surgical instrument assembly of claim 1, further comprising an actuator and a motor to drive said actuator through a stroke, and wherein said parameter comprises a position of said actuator.

5. A surgical instrument system, comprising:
   a surgical instrument assembly, comprising:
      a shaft;
      an end effector attached to said shaft; and
      a sensing system positioned within said shaft, wherein said sensing system is configured to:
         detect a parameter of said surgical instrument assembly; and
         detect a presence of outside interference that affects the parameter detection of said surgical instrument assembly; and
   a control circuit configured to:
      receive a signal from said sensing system;
      determine if said received signal has been altered by outside interference; and
      adjust a control program based on said signal having been determined to have been altered by outside interference.

6. The surgical instrument system of claim 4, wherein the surgical instrument assembly further comprises an actuator and a motor to drive said actuator through a stroke.

7. The surgical instrument system of claim 6, wherein said parameter comprises a position of said actuator.

8. The surgical instrument system of claim 6, wherein adjusting said control program comprises slowing a speed at which said motor is to drive said actuator.

9. The surgical instrument system of claim 6, wherein adjusting said control program comprises adjusting a length of said stroke.

10. The surgical instrument system of claim 6, wherein adjusting said control program comprises adjusting an amount of current that can be drawn by said motor from a power source.

11. A surgical instrument, comprising:
    an end effector;
    a shaft extending from said end effector, wherein said shaft comprises a sensing system to:
       detect a parameter of said surgical instrument; and
       detect outside interference that affects said detected parameter; and
    a control circuit to perform a function based on said detected outside interference.

12. The surgical instrument of claim 11, wherein said function comprises disabling said sensing system.

13. The surgical instrument of claim 11, wherein said control circuit is further to detect a magnitude of said outside interference.

14. The surgical instrument of claim 13, wherein said control circuit is further to:
    compare the magnitude of said outside interference to a threshold; and
    perform said function based on said comparison.

15. The surgical instrument of claim 13, wherein said control circuit is further to:
    determine if the magnitude of said outside interference is constant; and
    perform said function based on said determination.

16. The surgical instrument of claim 13, wherein said sensing system comprises a first sensing system, wherein said shaft further comprises a second sensing system, and wherein said function comprises switching from utilizing said first sensing system to utilizing said second sensing system.

17. The surgical instrument of claim 13, further comprising an actuator and a motor to drive said actuator through a stroke.

18. The surgical instrument of claim 17, wherein said function comprises slowing a speed at which said motor is to drive said actuator.

19. The surgical instrument of claim 17, wherein said function comprises adjusting a length of said stroke.

20. The surgical instrument of claim 17, wherein said function comprises adjusting an amount of current that can be drawn by said motor from a power source.

* * * * *